US011634733B2

(12) United States Patent
Cartman et al.

(10) Patent No.: US 11,634,733 B2
(45) **Date of Patent: *Apr. 25, 2023**

(54) METHODS, MATERIALS, SYNTHETIC HOSTS AND REAGENTS FOR THE BIOSYNTHESIS OF HYDROCARBONS AND DERIVATIVES THEREOF

(71) Applicant: INV Nylon Chemicals Americas, LLC, Wilmington, DE (US)

(72) Inventors: Stephen Thomas Cartman, Redcar (GB); Jonathan Paul Combe, Redcar (GB); Leonard Keith Pattenden, Redcar (GB); Andrew Shaw, Redcar (GB); Massimiliano Zampini, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/022,878

(22) Filed: Jun. 29, 2018

(65) Prior Publication Data

US 2019/0002926 A1 Jan. 3, 2019

Related U.S. Application Data

(60) Provisional application No. 62/527,595, filed on Jun. 30, 2017.

(51) Int. Cl.

| | |
|---|---|
| ***C12N 9/88*** | (2006.01) |
| ***C12P 5/00*** | (2006.01) |
| ***C12N 15/74*** | (2006.01) |
| ***C12N 9/12*** | (2006.01) |
| ***C12N 9/04*** | (2006.01) |
| ***C12N 9/10*** | (2006.01) |
| ***C12N 9/90*** | (2006.01) |

(52) U.S. Cl.

CPC ............ *C12P 5/007* (2013.01); *C12N 9/0006* (2013.01); *C12N 9/1029* (2013.01); *C12N 9/1205* (2013.01); *C12N 9/1229* (2013.01); *C12N 9/88* (2013.01); *C12N 9/90* (2013.01); *C12N 15/746* (2013.01); *C12Y 207/04002* (2013.01); *C12Y 401/01033* (2013.01); *C12Y 401/03* (2013.01); *C12Y 402/03027* (2013.01); *C12Y 503/03002* (2013.01); *C12Y 101/01034* (2013.01); *C12Y 203/01009* (2013.01); *C12Y 203/0301* (2013.01); *C12Y 207/01036* (2013.01)

(58) Field of Classification Search

CPC .. C12N 9/1229; C12N 9/1029; C12N 15/746; C12N 9/0006; C12Y 402/03027; C12P 5/007

USPC .......... 435/252.3, 167, 146, 320.1, 196, 195

See application file for complete search history.

(56) References Cited

U.S. PATENT DOCUMENTS

| | | | | |
|---|---|---|---|---|
| 4,605,620 | A | 8/1986 | Andersch et al. | 435/148 |
| 5,830,714 | A | 11/1998 | Swaminathan et al. | 435/91.2 |
| 8,703,455 | B2 | 4/2014 | Marliere | 435/167 |
| 8,741,612 | B2 | 6/2014 | Campbell et al. | 435/167 |
| 9,297,026 | B2 | 3/2016 | Koepke et al. | C12P 7/065 |
| 9,422,578 | B2 | 8/2016 | Pearlman et al. | C12P 5/02 |
| 9,422,580 | B2 | 8/2016 | Pearlman et al. | C12P 5/026 |
| 9,777,300 | B2 | 10/2017 | Yeh et al. | C12P 7/6409 |
| 9,862,973 | B2 | 1/2018 | Botes et al. | C12P 5/007 |
| 10,167,487 | B2 | 1/2019 | Conradie | C12P 5/007 |
| 10,538,788 | B2 | 1/2020 | Cartman et al. | 435/232 |
| 10,538,789 | B2 | 1/2020 | Kamionka et al. | C12P 5/007 |
| 2003/0148416 | A1 | 8/2003 | Berry | |
| 2008/0311640 | A1 | 12/2008 | Cox et al. | 435/168 |
| 2009/0117629 | A1 | 5/2009 | Schmidt-Dannert et al. | 435/134 |
| 2011/0053216 | A1 | 3/2011 | Vermass | 435/69.1 |
| 2011/0160501 | A1 | 6/2011 | Martin et al. | 585/14 |
| 2011/0165644 | A1 | 7/2011 | Marliere | 435/167 |
| 2011/0300597 | A1 | 12/2011 | Burk et al. | 435/167 |
| 2012/0015427 | A1 | 1/2012 | Green et al. | 435/257.2 |
| 2012/0021478 | A1 | 1/2012 | Osterhout et al. | 435/167 |
| 2012/0045807 | A1 | 2/2012 | Simpson et al. | 435/148 |
| 2012/0055081 | A1 | 3/2012 | Aravanis | |
| 2012/0122563 | A1 | 5/2012 | Walker et al. | |
| 2012/0164711 | A1* | 6/2012 | Muir et al. | |
| 2012/0225466 | A1 | 9/2012 | Burk et al. | 435/167 |
| 2012/0329119 | A1 | 12/2012 | Burgard et al. | 435/167 |
| 2013/0189753 | A1 | 7/2013 | Pearlman et al. | 435/167 |
| 2013/0210104 | A1 | 8/2013 | Pearlman et al. | 435/167 |
| 2013/0252300 | A1 | 9/2013 | Green et al. | 435/161 |
| 2013/0323820 | A1 | 12/2013 | Chen et al. | 435/252.3 |
| 2013/0330709 | A1 | 12/2013 | Beatty et al. | 435/4 |
| 2014/0065686 | A1 | 3/2014 | Marliere | 435/167 |
| 2014/0141482 | A1 | 5/2014 | Pearlman et al. | 435/167 |
| 2014/0148622 | A1* | 5/2014 | Nair | |

(Continued)

FOREIGN PATENT DOCUMENTS

| | | |
|---|---|---|
| CN | 103602626 | 2/1916 |
| EP | 2336340 | 6/2011 |

(Continued)

OTHER PUBLICATIONS

Davos et al., Proteins: Structure, Function and Genetics, 2000, vol. 41: 98-107.*

(Continued)

*Primary Examiner* — Robert B Mondesi
*Assistant Examiner* — Mohammad Y Meah

(57) ABSTRACT

Genetically engineered hosts and methods for their production and use in synthesizing hydrocarbons are provided.

6 Claims, 3 Drawing Sheets

Specification includes a Sequence Listing.

(56) References Cited

U.S. PATENT DOCUMENTS

| | | | | |
|---|---|---|---|---|
| 2014/0186913 | A1 | 7/2014 | Botes et al. | 435/167 |
| 2014/0206901 | A1 | 7/2014 | Koepke et al. | 562/577 |
| 2014/0234926 | A1* | 8/2014 | Zachary et al. | |
| 2014/0242649 | A1 | 8/2014 | Yeh et al. | 435/134 |
| 2014/0335576 | A1 | 11/2014 | Chotani et al. | 435/131 |
| 2015/0017694 | A1* | 1/2015 | Kurek | |
| 2015/0037860 | A1 | 2/2015 | Botes et al. | 435/167 |
| 2015/0037869 | A1 | 2/2015 | Savile et al. | 435/193 |
| 2015/0079654 | A1* | 3/2015 | Botes | |
| 2015/0140640 | A1 | 5/2015 | Reed | |
| 2015/0191747 | A1 | 7/2015 | Chen et al. | C12P 5/007 |
| 2015/0210987 | A1 | 7/2015 | Nagaraju et al. | C12N 9/0006 |
| 2015/0284742 | A1 | 10/2015 | Furutani et al. | 435/167 |
| 2015/0291981 | A1 | 10/2015 | Marliere et al. | C12P 5/026 |
| 2016/0002672 | A1* | 1/2016 | Zachary et al. | |
| 2016/0017374 | A1 | 1/2016 | Leonard et al. | C12P 5/007 |
| 2016/0130618 | A1 | 5/2016 | Hara et al. | |
| 2017/0051314 | A1 | 2/2017 | Conradie | C12P 5/007 |
| 2017/0106054 | A1 | 4/2017 | Summar et al. | A61K 38/44 |
| 2017/0145441 | A1 | 5/2017 | Conradie | |
| 2018/0094282 | A1 | 4/2018 | Cartman et al. | C12P 5/007 |
| 2018/0127788 | A1 | 5/2018 | Kamionka et al. | C12P 5/007 |
| 2018/0208952 | A1* | 7/2018 | Koepke | |
| 2018/0291401 | A1 | 10/2018 | Conradie | C12P 5/007 |
| 2019/0002927 | A1 | 1/2019 | Foster et al. | C12P 5/007 |
| 2019/0017076 | A1 | 1/2019 | Conradie | C12P 5/007 |
| 2019/0093130 | A1 | 3/2019 | Pearlman et al. | C12P 5/007 |
| 2019/0218577 | A1 | 7/2019 | Cartman et al. | C12P 5/007 |
| 2019/0271009 | A1 | 9/2019 | Conradie | C12P 5/007 |

FOREIGN PATENT DOCUMENTS

| | | | |
|---|---|---|---|
| EP | 2336341 | | 6/2011 |
| EP | 12190039 | | 10/2012 |
| EP | 2857509 | A1 | 4/2015 |
| EP | 2913392 | | 9/2015 |
| KR | 20150006097 | | 1/2015 |
| WO | 2017/029549 | | 2/1917 |
| WO | 2017/029553 | | 2/1917 |
| WO | 2018/064105 | | 4/1918 |
| WO | 2019/006255 | | 1/1919 |
| WO | 2019/006257 | | 1/1919 |
| WO | WO 2006/014837 | | 2/2006 |
| WO | 2009/064910 | | 5/2009 |
| WO | 2009/111513 | | 9/2009 |
| WO | 2009/132220 | | 10/2009 |
| WO | 2009/155382 | | 12/2009 |
| WO | 2010/001078 | | 1/2010 |
| WO | 2010/031062 | | 3/2010 |
| WO | 2010/099201 | | 9/2010 |
| WO | 2010/115838 | | 10/2010 |
| WO | 2011/011689 | | 1/2011 |
| WO | 2011/076261 | | 6/2011 |
| WO | 2011/076689 | | 6/2011 |
| WO | 2011/076691 | | 6/2011 |
| WO | 2011/079314 | | 6/2011 |
| WO | 2011/140171 | | 11/2011 |
| WO | 2012/018624 | | 2/2012 |
| WO | 2012/052427 | | 4/2012 |
| WO | 2012/174439 | | 12/2012 |
| WO | 2013/007786 | | 1/2013 |
| WO | 2013/020118 | | 2/2013 |
| WO | 2013/028519 | | 2/2013 |
| WO | 2013/036812 | | 3/2013 |
| WO | 2013/040383 | | 3/2013 |
| WO | 2013/057194 | | 4/2013 |
| WO | 2013/082542 | | 6/2013 |
| WO | 2013/090915 | | 6/2013 |
| WO | 2013/092567 | | 6/2013 |
| WO | 2013096863 | A1 | 6/2013 |
| WO | 2013/119340 | | 8/2013 |
| WO | 2013/150100 | | 10/2013 |
| WO | 2013/173437 | | 11/2013 |
| WO | 2013/180584 | | 12/2013 |
| WO | 2013/181647 | | 12/2013 |
| WO | 2013/188546 | | 12/2013 |
| WO | 2013/192183 | | 12/2013 |
| WO | 2014/001517 | | 1/2014 |
| WO | 2014/015210 | | 1/2014 |
| WO | 2014/033129 | | 3/2014 |
| WO | 2014/064198 | | 5/2014 |
| WO | 2014/085612 | | 6/2014 |
| WO | 2014/100726 | | 6/2014 |
| WO | 2014/193473 | | 12/2014 |
| WO | 2015/172972 | | 11/2015 |

OTHER PUBLICATIONS

Wristlock et al., Quarterly Reviews of Biophysics, 2003, vol. 36 (3): 307-340.*

Kwiatkowski et al., Biochemistry, 1999, vol. 38: 11643-11650.*

Kisselev L., Structure, 2002, vol. 10: 8-9.*

Kuzuyama et al. Proc Jap. Ser 2012 B 88, pp. 41-52.*

International Search Report and Written Opinion from PCT/US2018/040213 dated Sep. 21, 2018.

Slater, et al., "Multiple beta-ketothiolases mediate poly(beta-hydroxyalkanoate) copolymer synthesis in Ralstonia eutropha", Journal of Bacteriology, vol. 180, No. 8, Apr. 1998, p. 1979-1987.

Kuzuyama, Tomohisa, "Mevalonate and Nonmevalonate Pathways for the Biosynthesis of Isoprene Units", Bioscience Biotechnology Biochemistry, vol. 66, No. 8, 2002, pp. 1619-1627.

Whited et al., "Development of a Gas-Phase Bioprocess for Isoprene-Monomer Production Using Metabolic Pathway Engineering", Peer Review, Technology Update, Industrial Biotechnology, vol. 6, No. 3, 2010, pp. 152-163.

Makkar, et al., "Cupriavidus necatorgen. nov., sp. nov.: a Nonobligate Bacterial Predator of Bacteria in Soil", International Journal of Sysytematic Bacteriology, vol. 37, No. 4, Oct. 1987, p. 323-326.

Byrd, et al., "Bacterial control of Agromyces ramosus in soil", Can. J. Microbiol., vol. 31, 1985, p. 1157-1163.

Sillrnan, et al., "Isolation of nonobligate bacterial predators of bacteria from soil", Can. J. Microbiol., vol. 32, 1986, p. 760-762.

Zeph, et al., "Gram-negative versus gram-positive (actinomycete) nonobligate bacterial predators of bacteria in soil", Appl. Environ. Microbiol., vol. 522, 1986, p. 819-823.

Brigham, et al., "Genetics and Molecular Biology: Whole-Genome Microarray and Gene Deletion Studies Reveal Regulation of the Polyhydroxyalkanoate Production Cycle by the Stringent Response in Ralstonia eutropha H16", Appl. Environ. Microbiol., vol. 78:22, Nov. 2012, p. 8033-8044.

Pitera, et al., "Balancing a heterologous mevalonate pathway for improved isoprenoid production in *Escherichia coli*", Metab Eng., vol. 9(2), Mar. 2007, p. 193-207.

Ishizaki, et ai., "Microbial production of poly-D-3-hydroxybutyrate from CO2", Appl. Microbiol. Biotechnoi., vol. 57(1-2), Oct. 2001, p. 6-12.

Office Communication in U.S. Appl. No. 16/023,055 dated Jun. 25, 2020.

Office Communication in U.S. Appl. No. 16/144,035 dated Aug. 10, 2020.

Tan et al. "Activating Phosphenolpyruvate Carboxylase and Phosphoenolpyruvate Carboxykinase in Combination for Improvement of Succinate Production" Applied and Environmental Microbiolgy 2013 79(16):4838-4844.

Akatsuka et al. "The Serratia marcescens bioH gene encodes an esterase" Gene 2003 302:185-192.

Barta et al. "Structural basis for nucleotide binding and reaction catalysis in mevalonate diphosphate decarboxylase" Biochemistry 2012 51(28):5611-5621.

Becker et al. "Metabolic flux engineering of L-lysine production in Corynebacterium glutamicum—over expression and modification of G6P dehydrogenase" Journal of Biotechnology 2007 132:99-109.

Bischoff, K.M & Rodwell, V.W. "Biosynthesis and characterization of (S)-and (R)-3-hydroxy-3-methylglutaryl coenzyme A" Biochem Med Metab Biol 1992 48(2):149-58.

Boucher et al. "Bacterial origin for the isoprenoid biosynthesis enzyme HMG-CoA reductase of the archaeal orders Thermoplasmatales and Archaeoglobales" Mol. Biol. Evol. 2011 18(7):1378-1388.

(56) References Cited

OTHER PUBLICATIONS

Brigham et al. Advanced Biofuels and Bioproducts, Springer New York, Chapter 39 2013 pp. 1065-1090.
Brodkorb et al. "Linalool dehydratase-isomerase, a bifunctional enzyme in the anaerobic degradation of monoterpenes" J Biol Chem 285(40):30436-30442.
Buckel et al. "Glutaconate CoA-transferase from Acidaminococcus fermentans" Eur J Biochem 1981 118(2):315-321.
Buckel et al. "2-Hydroxyl-CoA Dehydratases, a novel family of moybdeum enzymes" J Inorganic Biochemistry 2003 96(1):53.
Bugg et al. "The emerging role for bacteria in lignin degradation and bio-product formation" Current Opinion in Biotechnology 2011 22:394-400.
Byrd et al. "Bacterial Control of Agromyces ramosus in soil" Can J Microbiol 1985 31:1157-1163.
Chayabutra & Ju "Degradation of n-hexadecane and its metabolites by Pseudomonas aeruginosa under microaerobic and anaerobic denitrifying conditions" Appl Environ Microbiol 2000 66(2):493-498.
Chica et al. "Semi-rational approaches to engineering enzyme activity: combining the benefits of directed evolution and rational design" Current Opinion in Biotechnology 2005 16:378-384.
Chung & Rhee "Overexpression of the (R)-specific enoyl-CoA hydratase gene from Pseudomonas chlororaphis HS21 in Pseudomonas strains for the biosynthesis of polyhydroxyalkanoates of altered monomer composition" Biosci Biotechnol Biochem 2012 76(3):613-616.
Daniel et al. "Biochemistry of coenzyme B12-dependent glycerol and diol dehydratases and organization of the encoding genes" FEMS Microbiology Reviews 1999 22:553-566.
Demain et al. "Manual of Industrial Microbiology and Biotechnology", $2^{nd}$ Edition, Scale-Up of Microbial Process, ASM Press, 1999, 5 pages.
Dhe-Paganon et al. "Mechanism of mevalonate pyrophosphate decarboxylase: evidence for a carbocationic transition state" Biochemistry 1994 33(45):13355-1336.
Eikmanns & Buckel "Crystalline green 5-hydroxyvaleryl-CoA dehydratase from Clostridium aminovalericum" Eur J Biochem 1991 197(3):661-668.
Eriksen et al. "Protein design for pathway engineering" Journal of Structural Biology 2013 185(2):234-242.
Ferrandez et al. "Genetic characterization and expression in heterologous hosts of the 3-(3-hydroxyphenyl)propionate catabolic pathway of *Escherichia coli* K-12" J Bacteriol 1997 179(8):2573-2581.
Forster-Fromme et al. "Biochemical characterization of isovaleryl-CoA dehydrogenase (LiuA) of Pseudomonas aeruginosa and the importance of liu genes fora functional catabolic pathway of methyl-branched compounds" FEMS Microbiol Lett 2008 286(1):78-8.
Fukui et al. "Expression and characterization of (R)-specific enoyl coenzyme a hydratase involved in polyhydroxyalkanoate biosynthesis by Aeromonas caviae" J Bacteriology 1998 180(3):667-673.
Gehret et al. "Terminal alkene formation by the thioesterase of curacin A biosynthesis: structure of a decarboxylating thioesterase" J Biol Chem 2011 186(16):14445-14454.
Genbank Accession No. AAD44196.1, Oct. 15, 1999 1 page.
Genbank Accession No. AAG02436.1, Aug. 29, 2000, 1 page.
Genbank Accession No. AAG05403.1, Jan. 31, 2014 1 page.
Genbank Accession No. AAK99143.1, Jan. 30, 2014, 2 pages.
Genbank Accession No. AAV40818.1, Feb. 4, 2005, 2 pages.
Genbank Accession No. AAV40819.1, Feb. 4, 2005, 1 page.
Genbank Accession No. AAV40820.1, Feb. 4, 2005, 1 page.
Genbank Accession No. ABX19602.1, Dec. 11, 2013, 2 pages.
Genbank Accession No. BAA21816.1, Aug. 19, 1997, 2 pages.
Genbank Accession No. BAA92740.1, Aug. 1, 2007, 2 pages.
Genbank Accession No. BAB56752.1, Oct. 7, 2016, 2 pages.
Genbank Accession No. BAB56754.1, Oct. 7, 2016, 1 page.
Genbank Accession No. BAB58707.1, Oct. 7, 2016, 2 pages.
Genbank Accession No. BAD98243.1, May 10, 2005, 2 pages.
Genbank Accession No. CAA32465.1, Jul. 26, 1995, 1 page.
Genbank Accession No. CAA32466.1, Jul. 26, 1995, 1 page.
Genbank Accession No. CAA42196.1, Oct. 16, 1995, 1 page.
Genbank Accession No. CAA99573.1, Nov. 14, 2006, 2 pages.
UniProtKB/Swiss-Prot. E1XUJ2.1, Sep. 5, 2012, 2 pages.
NCBI Reference Sequence NP 746661, Jun. 27, 2013, 2 pages.
Gogerty & Bobik "Formation of isobutene from 3-hydroxy-3-methylbutyrate by diphosphomevalonate decarboxylase" Appl Environ Microbiol 2010 76(24):8004-8010.
Gu et al. "Polyketide decarboxylative chain termination preceded by o-sulfonation in curacin a biosynthesis" Am J Chem Soc 2009 131(44):16033-1603.
Guan et al. "Cytochrome P450-dependent desaturation of lauric acid: isoform selectivity and mechanism of formation of 11-dodecenoic acid" Chem Biol Interact 1998 110(1-2):103-12.
Gupta et al. "Phylogenomics and signature proteins for the alpha Protobacteria and its main groups" BMC Microbiol. 2007 7:106:1-2.
He & Spain "A novel 2-aminomuconate deaminase in the nitrobenzene degradation pathway of Pseudomonas pseudoalcaligenes JS45" J Bacteriol 1998 180(9):2502-2506.
Hermann, T. "Industrial production of amino acids by coryneform bacteria" Journal of Biotechnology 2003 104:155-172.
Ishizaki et al. "Microbial production of poly-D-3-hydroxybutyrate from CO2" Appl Microbiol Biotechnol 2001 57(1-2):6-12.
Jang et al. "Bio-based production of C2-C6 platform chemicals" Biotechnol Bioeng 2012 109(10)::2437-2459.
Jaremko et al. "The initial metabolic conversion of levulinic acid in Cupriavidus necator" Journal of Biotechnology 2011 155:293-298.
Jin et al. "The selective addition of water to C═C bonds; enzymes are the best chemists" Chem Commun. 2011 47:2502-2510.
Kasai et al. "Uncovering the protocatechuate 2,3-cleavage pathway genes" J Bacteriol 2009 191(21):6758-6768.
Kelada et al. "Delta-aminolevulinic acid dehydratase genotype and lead toxicity: a HuGE review" Am. J. Epidemiology 2001 154(1):1-1.
Kim et al. "An allylic ketyl radical intermediate in clostridial amino-acid fermentation" Nature 2008 452(7184):239-24.
Kim et al. :Dehydration of (R)-2-hydroxyacyl-CoA to enoyl-CoA in the fermentation of α-amino acids by anaerobic bacteria FEMS Microbiol Rev 2004 28(4):445-468.
Kim, "On the enzymatic mechanism of 2-hydroxyisocaproyl-CoA dehydratase from Clostridium difficile" 2004 Ph.D. dissertation, Phillipps-Universitat, Marburg, 200.
Kizer et al. "Application of functional genomics to pathway optimization for increased isoprenoid production" Applied and Environmental Microbiology 2008 74(10):3229-3241.
Kneen et al. "Characterization of a thiamin diphosphate-dependent phenylpyruvate decarboxylase from *Saccharomyces cerevisiae*" FEBS J. 2011 278:1842-1853.
Kopke et al. "2,3-butanediol production by acetogenic bacteria, an alternative route to chemical synthesis, using industrial waste gas" Applied and Environmental Microbiology 2011 77(15):5467-5475.
Kuzma et al. "Bacteria produce the volatile hydrocarbon isoprene" Curr Microbiol 1995 30(2):97-103.
Kuzuyuma et al. "Mevalonate and Nonmevalonate Pathways for the Biosynthesis of Isoprene Units" Biosci. Biotechnol. Biochem. 2002 66(8):1619-1627.
Lan et al. "ATP drives direct photosynthetic production of 1-butanol in cyanobacteria" PNAS 2012 109(16):6018-6023.
Lee et al. "Conversion of β-Methylbutyrinc Acid to α-Hydroxy-β-Methylbutyrin Acid by Galactomyces reessii" Applied and Environmental Microbiology 1997 63(11):4191-4195.
Lee et al. "Synthesis of pure meso-2,3-butanediol from crude glycerol using an engineered metabolic pathway in *Escherichia coli*" Applied Biochemistry and Biotechnology 2012 166(7):1801-1813.
Li et al. "Cupriavidus necator JMP134 rapidly reduces furfural with a Zn-dependent alcohol dehydrogenase" Biodegradation 2011 22(6):1215-122.
Lim et al. "Amplification of the NADPH-related genes zwf and gnd for the oddball biosynthesis of PHB in an *E. coli* transformant harboring a cloned phbCAB operon" Journal of Bioscience and Bioengineering 2002 93(6):543-54.

(56) References Cited

OTHER PUBLICATIONS

Lin et al. "The BioC O-methyltransferase catalyzes methyl esterification of malonyl-acyl carrier protein, an essential step in biotin synthesis" Journal of Biological Chemistry 2012 287(440::37010-37020.
Lin et al. "Biotin synthesis begins by hijacking the fatty acid synthetic pathway" Nature Chem Biol 2010 6:682-68.
Liu et al. "Microbial production of R-3-hydroxybutyric acid by recombinant *E. coli* harboring genes of phbA, phbB, and tesB" Appl Microbiol Biotechnol 2007 76(4):811-181.
Liu et al. "Zirconia microbial hollow fibre bioreactor for *Esherichia coli* culture" Ceramics International 2010 36:2087-2093.
Lo, H. & Chen, Y.J. "Gene cloning and biochemical characterization of a NAD(P)+-dependent aldehyde dehydrogenase from Bacillus licheniformis" Mol. Biotechnol 2010 46(2):157-67.
Luddeke et al. "Geraniol and geranial dehydrogenases induced in anaerobic monoterpene degradation by Castellaniella defragrans" Appl and Environmental Microbiology 2012 78(7):2128-2136.
Luddeke et al. "Enantiospecific (S)-(+)-linalool formation from beta-myrcene by linalool dehydratase-isomerase" Z. Naturforsch C 2011 66(708):409-412.
Luo et al. "Production of 3-hydroxypropionic acid through propionaldehyde dehydrogenase PduP mediated biosynthetic pathway in Klebsiella pneumonia" Bioresour Technol 2011 103(1):1-6.
Makkar et al. "*Cupriavidus necator* gen. nov., sp, nov.: a Non Obligate Bacterial Predator of Bacteria in Soil" Bacteriology 1987 37(4):323-326.
Martin et al. "High-titer production of monomeric hydroxyvalerates from levulinic acid in Pseudomonas putida" Journal of Biotechnology 2009 139(1):61-67.
Martin et al. "Engineering a mevalonate pathway in *Escherichia coli* for production of terpenoids" Nature Biotechnology 2003 21:796-802.
McCarthy et al. "Structural basis of functional group activation by sulfotransferases in complex metabolic pathways" ACS Chem Biol 2012 7:1994-2003.
Meijnen et al. "Improved p-hydroxybenzoate production by engineered Pseudomonas putida S12 by using a mixed-substrate feeding strategy" Applied Microbiology and Biotechnology 2011 90(3):885-893.
Mo et al. "Biosynthesis of the Allylmalonyl-CoA Extended Unit for the FK506 Polyketide Synthase (PKS) Proceeds Through a Dedicated PKS and Faciliates the Mutasynthesis of Novel Analogs" J Am Chem Soc 2010 1333(4):976-985.
Morrone et al. "Increasing diterpene yield with a modular metabolic engineering system in *E. coli*: comparison of MEV and MEP isoprenoid precursor pathway engineering" Applied Microbiology and Biotechnology 2010 85:1893-1906.
Muraki et al. "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7" Appl Environ Microbiol 2003 69(3):1564-1572.
Ohashi et al. "Continuous production of lactic acid from molasses by perfusion culture of Lactococcus lactis using a stirred ceramic membrane reactor" Journal of Bioscience and Bioengineering 1999 87(5): 647-654.
Papanikolaou et al. "Citric acid production by Yarrowia lipolytica cultivated on olive-mill wastewater-based media" Bioresource Technology 2008 99(7):2419-2428.
Perez-Pantoja et al. "Metabolic reconstruction of aromatic compounds degradation from the genome of the amazing pollutant-degrading bacterium Cupriavidus necator JMP134" FEMS Microbiology Reviews 2008 32:736-794.
Pitera et al. "Balancing a heterologous mevalonate pathway for improved isoprenoid production in *Escherichia coli*" Metabolic Engineering 2007 9:193-207.
Prather et al. "De novo biosynthetic pathways: rational design of microbial chemical factories" Curr Opin Biotechnol 2008 19:468-474.
"Production of Butadiene" China Synthetic Rubber Industry, Special Issue of 1978, 21 pages (with partial English translation).
Przybylski et al. "Third-generation feed stocks for the clean and sustainable biotechnological production of bulk chemicals: Synthesis of 2-hydroxyisobutyric acid" Energy, Sustainability and Society 2012 2(11):1-9.
Ramsay et al. "Use of a nylon manufacturing waste as an industrial fermentation substrate" Applied and Environmental Microbiology 1986 52(1):152-156.
Rettie et al. "CYP4 isozyme specificity and the relationship between omega-hydroxylation and terminal desaturation of valproic acid" Biochemistry 1995 34(24):7889-7895.
Rodruguez-Zavala et al. "Characterization of *E. coli* tetrameric aldehyde dehydrogenases with atypical properties compared to other aldehyde dehydrogenases" Protein Science 2006 15:1387-1396.
Rude et al. "Terminal olefin (1-alkene) biosynthesis by a novel p450 fatty acid decarboxylase from *Jeotgalicoccus* species" Appl Environ Microbiol 2011 77(5):1718-1727.
Schafer et al. "Synthesis of short-chain diols and unsaturated alcohols from secondary alcohol substrates by the Rieske nonheme mononuclear iron oxygenase MdpJ" Appl Environ Microbiol 2012 78(17):6280-6284.
Scherf & Buckel "Purification and properties of an iron-sulfur and FAD-containing 4-hydroxybutyryl-CoA dehydratase/vinylacetyl-CoA delta 3-delta 2-isomerase from Clostridium aminobutyricum" Eur J Biochem 1993 215(2):421-429.
Scherf et al. "Succinate-ethanol fermentation in Clostridium kluyveri: purification and characterisation of 4-hydroxybutyryl-CoA dehydratase/vinylacetyl-CoA delta 3-delta 2-isomerase" Arch Microbiol 1994 161(3):239-245.
Seedorf et al. "The genome of Clostridium kluyveri, a strict anaerobe with unique metabolic features" PNAS USA 2008 105:2128-2133.
Sen et al. "Developments in directed evolution for improving enzyme functions" Appl Biochem Biotechnol 2007 143:212-223.
Shen et al. "Driving forces enable high-titer anaerobic 1-butanol synthesis in *Escherichia coli*" Appl Environ Microbiol 2011 77(9):2905-2915.
Sillman et al. "Isolation of nonobligate bacterial predators of bacteria from soil" Can J Microbiol 1986 32:760-762.
Silver & Fall "Characterization of aspen isoprene synthase, an enzyme responsible for leaf isoprene emission to the atmosphere" J Biol Chem 1995 270(22):13010-13016.
Studier "Protein production by auto-induction in high density shaling cultures" Protein Expression and Purification 2005 41:207-234.
Sweeney et al. "Physiologically based pharmacokinetic modeling of 1,3-butadiene, 1,2-epoxy-3-butene, and 1,2:3,4-diepoxybutane toxicokinetics in mice and rats" Carcinogenesis 1997 18(4):611-625.
Toraya et al. "Radical catalysis of B12 enzymes: structure, mechanism, inactivation, and reactivation of diol and glycerol dehydratases" Cellular and Molecular Life Sciences 2000 57:106-127.
Tseng et al. "Biosynthesis of chiral 3-hydroxyvalerate from single propionate-unrelated carbon sources in metabolically engineered *E. coli*" Microb Cell Fact 2010 9:96.
Tsuge et al. "Molecular characterization and properties of (R)-specific enoyl-CoA hydratases from Pseudomonas aeruginosa: metabolic tools for synthesis of polyhydroxyalkanoates via fatty acid beta-oxidation" Int J. Biol Macromol 2003 31(4-5):195-205.
Ulmer et al. "Bacterial Production of Poly((β-hydroxyalkanoates) Contaning Unsaturated Repeating Units by Rhodospirillum rubrum" Macromolecules 1994 27(7):1675-1679.
Uniprot Accession No. 032472, Jun. 11, 2014, 2 pages.
Uniprot Accession No. B8ZLF3, Jun. 15, 2010, 2 pages.
Uniprot Accession No. I3RA72, Sep. 5, 2012, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.

(56) References Cited

OTHER PUBLICATIONS

Uniprot Accession No. P0AEK2, May 14, 2014, 4 pages.
Uniprot Accession No. P13001, Jun. 11, 2014, 4 pages.
Uniprot Accession No. P32377, Jun. 15, 2010, 4 pages.
Uniprot Accession No. Q5EU90, Feb. 19, 2014, 2 pages.
Uniprot Accession No. Q73A47, May 14, 2014, 2 pages.
Uniprot Accession No. Q7CCL9, Jun. 15, 2010, 2 pages.
Uniprot Accession No. Q818X2, Jun. 11, 2014, 2 pages.
Upton & McKinney "Role of the methylcitrate cycle in propionate metabolism and detoxification in Mycobacterium smegmatis" Microbiology 2007 153(Pt 12):3973-3982.
Van Leeuwen et al. "Fermentative production of isobutene" Appl Microbiol Biotechnol 2012 93(4):1377-1387.
Wang & Liao "Alteration of product specificity of Rhodobacter sphaeroides phytoene desaturase by directed evolution" J Biol Chem 2001 276(44):41161-41164.
Wee et al. "Biotechnological Production of Lactic Acid and Its Recent Applications" Food Technology and Biotechnology 2006 44(2):163-172.
Wendt et al. "Crystal structure of the carboxyltransferase subunit of the bacterial sodium ion pump glutaconyl-coenzyme A decarboxylase" EMBO J 2003 22(14):3493-3502.
Westin et al. "The identification of a succinyl-CoA thioesterase suggests a novel pathway for succinate production in peroxisomes" J Biol Chem 2005 280:38125-38132.
White "Butadiene production process overview" Chem Biol Interact 2007 166(1-3):10-14.
Yang et al. Enhancing Production of Bio-Isoprene Using Hybrid MVA Pathway and Isoprene Synthase in *E. coli*: PLoS One 2012 7:1-7.
Yang et al. "Value-added uses for crude glycerol-a byproduct of biodiesel production" Biotechnology for Biofuels 2012 5(10):1-10.
Zeph et al. "Gram-negative versus gram-positive (actinomycete) nonobligate bacterial predators of bacteria in soil" Appl Environ Microbiol 1986 522:819-823.
Zhang et al. "Genes encoding acyl-CoA dehydrogenase (AcdH) homologues from Streptomyces coelicolor and Streptomyces avermitilis provide insights into the metabolism of small branched-chain fatty acids and macrolide antibiotic production" Microbiology 1999 145(9):2323-2334.
Zhao et al. "Biosynthesis of isoprene in *Escherichia coli* via methylerythritol phosphate (MEP) pathway" Applied Microbiology and Biotechnology 2011 90:1915-1922.
Zhou et al. "Isopentenyl diphosphate and dimethylallyl diphosphate/isopentenyl diphosphate ratio measured with recombinant isopentenyl diphosphate isomerase and isoprene synthase" Analytical Biochemistry 2013 440:130-136.
Zhuang et al. "Structure of YciA from Haemophilus influenzae (HI0827), a hexameric broad specificity acyl-coenzyme a thioesterase" Biochemistry 2008 47(9):2789-2796.
Chinese Office Action in Chinese Application No. 201280040122.2 dated Jul. 17, 2015.
Office Communication in CN201280068870.1 dated Aug. 23, 2016.
Office Communication in CN201280040122.2 dated Jun. 8, 2016.
Office Communication in CN201380043586.3 dated Nov. 8, 2016.
European Communication pursuant to Rules 161(1) and 162 EPC in application No. EP 12799032.3 dated Jun. 25, 2014.
Office Communication in EP 12799032.3 dated Dec. 10, 2015.
Office Communication in EP 12799032.3 dated Mar. 3, 2016.
Office Communication in EP 12799032.3 dated Jun. 16, 2016.
Office Communication in EP12731825.1 dated Nov. 17, 2015.
Office Communication in EP12731825.1 dated Feb. 4, 2019.
Office Communication in EP 13812263.5 dated Jan. 12, 2017.
Office Communication in EP 13812263.5 dated Sep. 26, 2018.
Office Communication in U.S. Appl. No. 13/524,973 dated Jun. 11, 2014.
Office Communication in U.S. Appl. No. 13/524,973 dated Dec. 22, 2014.
Office Communication in U.S. Appl. No. 13/524,973 dated Jul. 23, 2015.
Office Communication in U.S. Appl. No. 13/524,973 dated Apr. 20, 2016.
Office Communication in U.S. Appl. No. 13/524,973 dated Aug. 30, 2016.
Office Communication in U.S. Appl. No. 13/524,973 dated Jan. 26, 2017.
Office Communication in U.S. Appl. No. 13/691,623 dated Mar. 4, 2014.
Office Communication in U.S. Appl. No. 13/691,623 dated Jun. 25, 2014.
Office Communication in U.S. Appl. No. 13/691,623 dated Dec. 9, 2014.
Office Communication in U.S. Appl. No. 13/691,623 dated Mar. 16, 2015.
Office Communication in U.S. Appl. No. 13/691,623 dated Apr. 23, 2015.
Office Communication in U.S. Appl. No. 13/691,623 dated Jul. 17, 2015.
Office Communication in U.S. Appl. No. 13/691,623 dated Dec. 7, 2015.
Office Communication in U.S. Appl. No. 13/691,623 dated May 4, 2016.
Office Communication in U.S. Appl. No. 13/916,156 dated Jan. 9, 2015.
Office Communication in U.S. Appl. No. 13/916,156 dated Jul. 14, 2015.
Office Communication in U.S. Appl. No. 13/916,156 dated Dec. 3, 2015.
Office Communication in U.S. Appl. No. 13/916,156 dated Mar. 15, 2016.
Office Communication in U.S. Appl. No. 13/916,156 dated Apr. 7, 2016.
Office Communication in U.S. Appl. No. 13/916,156 dated Apr. 20, 2016.
Office Communication in U.S. Appl. No. 13/916,156 dated May 17, 2016.
Office Communication in U.S. Appl. No. 14/092,115 dated Apr. 1, 2015.
Office Communication in U.S. Appl. No. 14/092,115 dated Oct. 27, 2015.
Office Communication in U.S. Appl. No. 14/092,115 dated Feb. 2, 2016.
Office Communication in U.S. Appl. No. 14/092,115 dated Mar. 21, 2016.
Office Communication in U.S. Appl. No. 14/092,115 dated Jul. 12, 2016.
Office Communication in U.S. Appl. No. 14/092,115 dated Oct. 12, 2016.
Office Communication in U.S. Appl. No. 14/092,115 dated Apr. 6, 2017.
Office Communication in U.S. Appl. No. 14/092,115 dated Jul. 27, 2017.
Office Communication in U.S. Appl. No. 14/334,190 dated Feb. 5, 2016.
Office Communication in U.S. Appl. No. 14/334,190 dated Jul. 27, 2016.
Office Communication in U.S. Appl. No. 14/334,190 dated Jan. 20, 2017.
Office Communication in U.S. Appl. No. 14/334,190 dated May 9, 2017.
Office Communication in U.S. Appl. No. 14/334,190 dated Oct. 5, 2017.
Office Communication in U.S. Appl. No. 14/334,190 dated Mar. 13, 2018.
Office Communication in U.S. Appl. No. 14/334,190 dated Apr. 25, 2018.
Office Communication in U.S. Appl. No. 14/334,190 dated Jul. 30, 2018.
Office Communication in U.S. Appl. No. 14/334,190 dated Sep. 10, 2018.
Office Communication in U.S. Appl. No. 14/334,190 dated Sep. 28, 2018.

(56) References Cited

OTHER PUBLICATIONS

Office Communication in U.S. Appl. No. 14/334,190 dated Nov. 16, 2018.
Office Communication in U.S. Appl. No. 14/334,190 dated Jan. 9, 2019.
Office Communication in U.S. Appl. No. 14/452,201 dated May 20, 2016.
Office Communication in U.S. Appl. No. 14/452,201 dated Oct. 28, 2016.
Office Communication in U.S. Appl. No. 14/452,201 dated Apr. 5, 2017.
Office Communication in U.S. Appl. No. 14/452,201 dated Aug. 30, 2017.
Office Communication in U.S. Appl. No. 14/914,741 dated Nov. 17, 2016.
Office Communication in U.S. Appl. No. 14/914,741 dated Feb. 7, 2017.
Office Communication in U.S. Appl. No. 14/914,741 dated Aug. 17, 2017.
Office Communication in U.S. Appl. No. 14/914,741 dated Jul. 24, 2018.
Office Communication in U.S. Appl. No. 14/914,741 dated Apr. 19, 2019.
Office Communication in U.S. Appl. No. 14/914,741 dated Sep. 16, 2019.
Office Communication in U.S. Appl. No. 15/238,225 dated Dec. 18, 2018.
Office Communication in U.S. Appl. No. 15/238,225 dated Mar. 11, 2019.
Office Communication in U.S. Appl. No. 15/238,225 dated Oct. 10, 2019.
Office Communication in U.S. Appl. No. 15/238,225 dated Feb. 27, 2020.
Office Communication in U.S. Appl. No. 15/238,234 dated Nov. 30, 2017.
Office Communication in U.S. Appl. No. 15/238,234 dated May 2, 2018.
Office Communication in U.S. Appl. No. 15/238,234 dated Aug. 13, 2018.
Office Communication in U.S. Appl. No. 15/238,234 dated Nov. 16, 2018.
Office Communication in U.S. Appl. No. 15/717,065 dated Nov. 8, 2018.
Office Communication in U.S. Appl. No. 15/717,065 dated Feb. 13, 2019.
Office Communication in U.S. Appl. No. 15/717,065 dated Jun. 19, 2019.
Office Communication in U.S. Appl. No. 15/717,065 dated Oct. 1, 2019.
Office Communication in U.S. Appl. No. 15/808,409 dated May 8, 2019.
Office Communication in U.S. Appl. No. 15/808,409 dated Sep. 5, 2019.
Office Communication in U.S. Appl. No. 15/932,217 dated Jun. 10, 2019.
Office Communication in U.S. Appl. No. 15/932,217 dated Sep. 13, 2019.
Office Communication in U.S. Appl. No. 15/932,189 dated Dec. 5, 2019.
Office Communication in U.S. Appl. No. 16/188,673 dated Dec. 10, 2019.
Office Communication in U.S. Appl. No. 16/023,055 dated Oct. 7, 2019.
Office Communication in U.S. Appl. No. 16/023,055 dated Feb. 5, 2020.
International Search Report in PCT/US2012/042757 dated Mar. 6, 2013.
International Preliminary Report on Patentability in PCT/US2012/042757 dated Dec. 17, 2013.
International Search Report in PCT/US2012/064407 dated Feb. 7, 2013.
International Preliminary Report on Patentability in PCT/US2012/064407 dated May 13, 2014.
International Search Report in PCT/US2012/067463 dated Jun. 17, 2013.
International Preliminary Report on Patentability in PCT/US2012/067463 dated Jun. 3, 2014.
International Search Report and Written Opinion in PCT/US2013/045430 dated Feb. 3, 2014.
International Preliminary Report on Patentability in PCT/US2013/045430 dated Dec. 16, 2014.
International Search Report and Written Opinion in PCT/US2013/072275 dated Mar. 6, 2014.
International Preliminary Report on Patentability in PCT/US2013/072275 dated Jun. 2, 2015.
International Search Report and Written Opinion in PCT/US2014/048606 dated Oct. 31, 2014.
International Preliminary Report on Patentability in PCT/US2014/048606 dated Feb. 2, 2016.
International Search Report and Written Opinion in PCT/US2014/049786 dated Sep. 11, 2015.
International Preliminary Report on Patentability in PCT/US2014/049786 dated Feb. 9, 2016.
International Search Report and Written Opinion in PCT/US2014/049807 dated Nov. 5, 2014.
International Preliminary Report on Patentability in PCT/US2014/049807 dated Feb. 9, 2016.
International Search Report and Written Opinion in PCT/IB2016/001233 dated Feb. 28, 2017.
International Report on Patentability in PCT/IB2016/001233 dated Feb. 20, 2018.
International Search Report and Written Opinion in PCT/IB2016/001245 dated Feb. 27, 2017.
International Report on Patentability in PCT/IB2016/001245 dated Feb. 20, 2018.
International Search Report and Written Opinion in PCT/US2017/053607 dated Dec. 22, 2017.
International Report on Patentability in PCT/ U52017/053607 dated Apr. 2, 2019.
International Search Report and Written Opinion in PCT/US2018/040213 dated Sep. 21, 2018.
International Report on Patentability in PCT/US2018/040213 dated Dec. 31, 2019.
International Search Report and Written Opinion in PCT/US2018/040218 dated Oct. 3, 2018.
International Report on Patentability in PCT/US2018/040218 dated Dec. 31, 2019.
Lv et al. "Significantly enhanced production of isoprene by ordered coexpression of genes dxs, dxr, and idi in *Escherichia coli*" Appl Microbio. Biotechnol 2013 97:2357-2365.
Office Communication in U.S. Appl. No. 16/144,035 dated Mar. 9, 2020.
Islam et al. "Investigating Moorella thermoacetica Metabolism with a Genome-Scale ConstraintObased Metabolic Model" Integrative Biology 2015 26 pages.
Marcellin et al. "Low Carbon Fuels and Commodity Chemicals from Waste Gases—Systematic Approach to Understand Energy Metabolism in a Model Acetogen" Green Chemistry Royal Society of Chemistry, 2016 10 pages.
Nagarajan et al. "Characterizing Acetogenic Metabolism Using a Genome-Scale Metabolic Reconstruction of Clostridium ljungdahili" Microbial Cell Factories 2013 pp. 1-13.
Pereira et al. "Improving the Flux Distributions Simulated with Genome-Scale Metabolic Models of Saccaromy cescerevisiae" Metabolic Engineering Communications 3 2016 153-163.
Valgepea et al. "Maintenance of ATP Homeostasis Triggers Metabolic Shifts in Gas-Fermenting Acetogens" Cell Systems 2017 4:505-515.
Office Communication in U.S. Appl. No. 16/144,035 dated Dec. 24, 2020.
Non Final Office Action received for U.S. Appl. No. 15/238,225, dated Dec. 14, 2020, 17 Pages.

(56) References Cited

OTHER PUBLICATIONS

Office Action received for U.S. Appl. No. 15/238,225, dated Apr. 1, 2022, 17 Pages.
Peoples et al.,"Poly-beta-hydroxybutyrate biosynthesis in Alcaligenes eutrophus H16", Characterization of the genes encodingbeta-ketothiolase and acetoacetyl-CoA reductase; J. Biol. Chem, vol. 264, No. 26, p. 15293-15297, 1989.
"A9ASTO UniProtKB" ,UniProt enzyme classification 5.3.3.2, IDI_BURM1, Isopentenyl-diphosphate delta-isomerase, Retrieved on on Sep. 13, 2022, 05 pages.
Genbank Accession No. AAA21972.1, Apr. 24, 1993, 1 page.
Genbank Accession No. AAA24665.1, Apr. 26, 1993, 1 page.
GenBank Accession No. AAG43513.1, Jul. 14, 2016, 1 page.
Genbank Accession No. AAK33797.1, Apr. 1, 2014, 2 pages.
GenBank Accession No. AAO//182.1, Jan. 31, 2014, 2 pages.
Genbank Accession No. ACA99172.1, Dec. 11, 2013, 3 pages.
Genbank Accession No. ACT54545.1, Jul. 21, 2009, 2 pages.
Genbank Accession No. ACV42478.1, Feb. 12, 2014, 2 pages.
Genbank Accession No. ADU56236.1, Apr. 8, 2011, 2 pages.
Genbank Accession No. ADU56239.1, Apr. 8, 2011, 2 pages.
Genbank Accession No. AER12131.1, Oct. 29, 2011, 2 pages.
Genbank Accession No. AFY98994.1, Aug. 27, 2013, 2 pages.
Genbank Accession No. AHF01884.1, Jan. 3, 2014, 2 pages.
Genbank Accession No. BAA14785.1, Sep. 29, 2018, 12 pages.
Genbank Accession No. BAB58708.1, Oct. 7, 2016, 2 pages.
Genbank Accession No. CAA44858.1, Apr. 28, 1992, 2 pages.
Genbank Accession No. CAA66158.1, Oct. 29, 1997, 2 pages.
Genbank Accession No. CAC12426.1, Feb. 27, 2015, 2 pages.
Genbank Accession No. CAR68209.1, Feb. 6, 2015, 2 pages.
Genbank Accession No. CBW30//6.1, Jan. 19, 2012, 1 page.
GenBank Accession No. CCC78182.1, Feb. 27, 2015, 2 pages.
Genbank Accession No. Q835L4, Oct. 31, 2006, 2 pages.
Genbank accession No. AEK70970.1, Apr. 15, 2013, 2 pages.
Wilding et al.,"Identification, Evolution, and Essentiality of the Mevalonate Pathway for Isopentenyl Diphosphate Biosynthesis in Gram-Positive Cocci" Journal of Bacteriology, vol. 182, No. 15, Aug. 2000, pp. 4319-4327.
Willis, M. A. et al., "Structure of YciA from Haemophilus influenzae (H10827), a Hexameric Broad Specificity Acyl-Coenzyme A Thioesterase," Biochemistry, 2008, vol. 47, Issue 9, pp. 2797-2805.
Zhuang, Z., et al., "Divergence of function in the hotdog fold enzyme superfamily: the bacterial thioesterase YciA", Biochemistry, vol. 47, No. 9, Mar. 4, 2008, pp. 2789-2796.
Lechner, A., et al., "Designed biosynthesis of 36-methyl-FK506 by polyketide precursor pathway engineering", ACS Synthetic Biology, vol. 2, Issue 7, Jul. 2013, pp. 379-383.
Lefurgy, S.T., et al., "Probing ligand-binding pockets of the mevalonate pathway enzymes from Streptococcus oneumoniae". The Journal of Biological Chemistry, vol. 285, Issue 27, Jul. 2010, pp. 20654-20663.
NCBI Reference Sequence: WP_000163323.1, Oct. 12, 2019, 2 pages.
NCBI Reference Sequence: WP_000210618.1, Mar. 22, 2021, 2 pages.
NCBI Reference Sequence: WP_000373455.1, Jun. 3, 2019, 1 page.
NCBI Reference Sequence: WP_000562415.1, Jun. 20, 2019, 1 page.
NCBI Reference Sequence: WP_002382276, Jun. 3, 2019, 2 Pages.
Non-Final Rejection received for U.S. Appl. No. 15/238,225, dated Oct. 3, 2022, 16 Pages.
Park, S.J., et al., "Identification and Characterization of a New Enoyl Coenzyme A Hydratase Involved in Biosynthesis of Medium-Chain-Length Polyhydroxyalkanoates in Recombinant *Escherichia coli*", Journal of Bacteriology, vol. 185, No. 18, Sep. 15, 2003, pp. 5391-5397.
Pohlmann et al."Genome sequence of the bioplastic-producing "Knallgas" bacterium Ralstonia eutropha H16", Nature Biotechnology, vol. 25, No. 4, 07 p. 2006.
Reference "NCBI" (2019, updated) https://www.ncbi.nlnn.nih.goV/protein/AN050205.1, "hydroxymethylglutaryl-CoA synthase", pp. 1-2.
Reference "NCBI" (2019, updated) https://www.ncbi.nlm.nih.gov/protein/WP_000786547.1, "acetyl-CoA acetyltransferase [Proteobacteria]", Jun. 30, 2016, p. 1.
Schafer, F., et al., "Formation of Alkenes via Degradation of tert-Alkyl Ethers and Alcohols by Aquincola tertiaricarbonis L108 and Methylibium spp.", Applied and environmental Microbiology, vol. 77, Issue 17, Sep. 2011, pp. 5981-5987.
Uniprot Accession No. Q73Q47, May 14, 2014, 2 pages.
UniProtKB/Swiss-Prot: Q50L36.1, Feb. 23, 2022, 3 pages.
Valgepea, K., et al., "Arginine deiminase pathway provides ATP and boosts growth of the gas-fermenting acetogen Clostridium autoethanogenum", Metabolic Engineering, vol. 41, May 2017, 44 pages.
Vinokur, J.M., et al., "Evidence of a novel mevalonate pathway in archaea", Biochemistry, vol. 53, Issue 25, Jul. 1, 2014, pp. 4161-4168.

* cited by examiner

METHODS, MATERIALS, SYNTHETIC HOSTS AND REAGENTS FOR THE BIOSYNTHESIS OF HYDROCARBONS AND DERIVATIVES THEREOF

This patent application claims the benefit of priority from U.S. Provisional Application Ser. No. 62/527,595, filed Jun. 30, 2017, the teachings of which are herein incorporated by reference in their entirety.

FIELD

The present invention relates to recombinant host cells polynucleotides and polypeptides, methods for their production, and methods for their use in production of hydrocarbons.

BACKGROUND

Hydrocarbons are important monomers for the production of specialty elastomers including motor mounts/fittings, surgical gloves, rubber bands, golf balls and shoes. For example, styrene-isoprene-styrene block copolymers form a key component of hot-melt pressure-sensitive adhesive formulations and cis-poly-isoprene is utilized in the manufacture of tires (Whited et al. Industrial Biotechnology 2010 6(3):152-163). Manufacturers of rubber goods depend on either imported natural rubber from the Brazilian rubber tree or petroleum-based synthetic rubber polymers (Whited et al. 2010, supra).

Given an over-reliance on petrochemical feedstocks, biotechnology offers an alternative approach to the generation of industrially relevant products, via biocatalysis. Biotechnology offers more sustainable methods for producing industrial intermediates, in particular isoprene and isoprenoids.

Construction of recombinant microorganisms and methods of their use to produce hydrocarbons such as isoprene are known in the art. However, many of these methods and processes are unsatisfactory because they rely on agricultural commodities such as sugar cane and corn which can be volatile in supply and cost from time to time. The use of sugar derived from agricultural waste, often called 'biomass' has been proposed.

There are known metabolic pathways leading to the synthesis of isoprene in eukaryotes such as *Populus alba* and some prokaryotes such as *Bacillus subtilis* have been reported to emit isoprene (Whited et al. 2010, supra). Isoprene production in prokaryotes is however rare, and no prokaryotic isoprene synthase (hereafter ISPS) has been described to date.

Generally, two metabolic routes have been described incorporating the molecule dimethylallyl-pyrophosphate, the precursor to isoprene. These are known as the mevalonate and the non-mevalonate pathways (Kuzuyama Biosci. Biotechnol. Biochem. 2002 66(8):1619-1627), both of which function in terpenoid synthesis in vivo. Both require the introduction of a non-native ISPS in order to divert carbon to isoprene production.

The mevalonate pathway generally occurs in higher eukaryotes and Archaea and incorporates a decarboxylase enzyme, mevalonate diphosphate decarboxylase (hereafter MDD), that introduces the first vinyl-group into the precursors leading to isoprene. The second vinyl-group is introduced by isoprene synthase in the final step in synthesizing isoprene. The non-mevalonate pathway or 2-C-methyl-D-erythritol 4-phosphate (MEP) pathway occurs in many bacteria and dimethylallyl-PP is generated alongside isopentenyl-PP, two molecules which are interconvertible via the action of isopentenyl pyrophosphate isomerase or isopentyl diphosphate isomerase (hereafter IDI).

The mevalonate (MVA) dependent pathway can be split into two units; the upper pathway for the generation of mevalonic acid from central metabolism and the lower pathway for the conversion of mevalonic acid to IPP and DMAPP. In the upper mevalonate pathway, two molecules of acetyl-CoA are condensed to form acetoacetyl-CoA by the action of acetoacetyl-CoA C-acetyltransferase (AACT, EC 2.3.1.9). Acetoacetyl-CoA is then converted to HMG-CoA by HMG-CoA synthase (HMGS, EC 2.3.3.10) and HMG-CoA reductase (HMGR, EC 1.1.1.34) catalyses the reduction of HMG-CoA to mevalonate. Mevalonate then feeds into the lower mevalonate pathway where sequential phosphorylation by mevalonate kinase (MVK, EC 2.7.1.36) and phosphomevalonate kinase (MPK, EC 2.7.4.2), followed by a decarboxylation reaction by mevalonate diphosphate decarboxylase (MDD, EC 4.1.1.33), converts mevalonate to IPP. IPP is then isomerised to DMAPP by isopentenyl diphosphate isomerase (IDI, EC 5.3.3.2).

There is a need for genetically engineered hosts capable of stable hydrocarbon production.

SUMMARY

Disclosed herein are methods, compositions and hosts for synthesizing hydrocarbons and derivatives thereof.

In one nonlimiting embodiment, the methods, compositions and hosts are used to synthesize hydrocarbons comprising one or more isoprene units as depicted in Formula I (I)

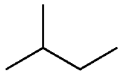

as well as salts or derivatives thereof.

An aspect of the present invention relates to a genetically engineered host capable of producing hydrocarbons or derivatives thereof via a mevalonate (MVA) pathway.

In one nonlimiting embodiment the hydrocarbon produced from the genetically engineered host comprises one or more isoprene units as depicted in Formula I (I)

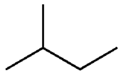

or a salt or derivative thereof.

Recombinant hosts of the present invention comprise at least one genome-integrated synthetic operon encoding an enzyme of the MVA pathway.

In one nonlimiting embodiment, the genetically engineered host comprises a genome-integrated synthetic operon encoding a plurality of enzymes of the MVA pathway.

In one nonlimiting embodiment, the genetically engineered host comprises a genome integrated synthetic operon encoding one or more enzymes of the upper MVA pathway.

In one nonlimiting embodiment, the genetically engineered host comprises a genome-integrated synthetic operon encoding the *Enterococcus faecalis* upper MVA pathway.

In one nonlimiting embodiment, the genetically engineered host comprises a genome integrated synthetic operon encoding one or more enzymes of the lower MVA pathway.

In one nonlimiting embodiment, the genetically engineered host comprises a genome-integrated synthetic operon encoding *Streptococcus pneumoniae* lower MVA pathway.

In one nonlimiting embodiment, the genetically engineered host comprises a genome-integrated synthetic operon encoding the *Enterococcus faecalis* upper MVA pathway and a genome-integrated synthetic operon encoding *Streptococcus pneumoniae* lower MVA pathway.

In one nonlimiting embodiment, the genetically engineered host comprises a genome-integrated synthetic operon encoding mevalonate kinase (MK), mevalonate phosphokinase (MPK), and mevalonate decarboxylase (MDD).

In any of these nonlimiting embodiments, the genetically engineered host may further comprise a genome-integrated transcription unit coding for an isoprene synthase.

In any of these embodiments, the genetically engineered host may further comprise one or more plasmids encoding one or more enzymes of the upper and/or lower MVA pathways.

Another aspect of the present invention relates to a method for producing genetically engineered stable strains of host cells which produce hydrocarbons.

In one nonlimiting embodiment the hydrocarbon produced from the genetically engineered host comprises one or more isoprene units as depicted in Formula I (I)

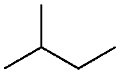

or a salt or derivative thereof.

In one nonlimiting embodiment of this method, at least one synthetic operon encoding an enzyme of the MVA pathway is integrated into the host genome.

In one nonlimiting embodiment of this method, at least one synthetic operon encoding a plurality of enzymes of the MVA pathway is integrated into the host genome.

In one nonlimiting embodiment of this method, a synthetic operon encoding one or more enzymes of the upper MVA pathway is integrated into the host genome.

In one nonlimiting embodiment of this method, a synthetic operon encoding all or part of the *Enterococcus faecalis* upper MVA pathway is integrated into the host genome.

In one nonlimiting embodiment of this method, a synthetic operon encoding one or more enzymes of the lower MVA pathway is integrated into the host genome.

In one nonlimiting embodiment of this method, a synthetic operon encoding all or part of the *Streptococcus pneumoniae* lower MVA pathway is integrated into the host genome.

In one nonlimiting embodiment, a synthetic operon encoding all or part of the *Enterococcus faecalis* upper MVA pathway and a synthetic operon encoding all or part of the *Streptococcus pneumoniae* lower MVA pathway are integrated into the host genome.

In one nonlimiting embodiment, a synthetic operon encoding mevalonate kinase (MK), mevalonate phosphokinase (MPK), and mevalonate decarboxylase (MDD) is integrated into the host genome.

Any of these nonlimiting embodiments of this method may further comprise integrating a transcription unit coding for an isoprene synthase into the host genome.

Further, in any of these embodiments, one or more plasmids encoding one or more enzymes of the upper and/or lower MVA pathways and/or an isoprene synthase may be incorporated into the host.

Another aspect of the present invention relates to methods for producing hydrocarbons in a genetically engineered host capable of stable hydrocarbon production.

In one nonlimiting embodiment the hydrocarbon produced from the genetically engineered host comprises one or more isoprene units as depicted in Formula I (I)

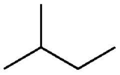

or a salt or derivative thereof.

Another aspect of the present invention relates to hydrocarbons such as bioderived hydrocarbons, produced in or obtainable from a genetically engineered host capable of stable hydrocarbon production, such as a host as described herein.

Yet another aspect of the present invention relates to products such as bio-derived, bio-based, or fermentation-derived products, produced from or obtainable from any of the hosts or methods described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word “comprising” in the claims may be replaced by “consisting essentially of” or with “consisting of,” according to standard practice in patent law.

DETAILED DESCRIPTION

Figure 1A:
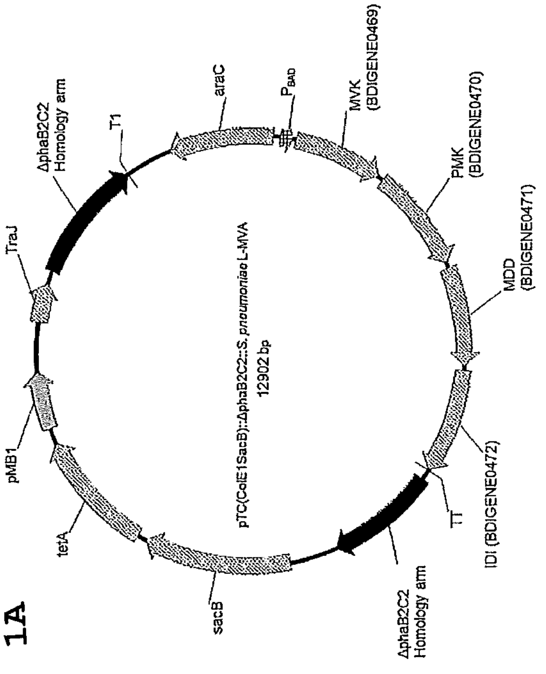
FIGS. 1A through 1D are plasmid maps for integration vectors pTc(ColE1SacB)::ΔphaB2C2::$P_{BAD}$::*S. pneumoniae* L-MVA (FIG. 1A) and pTC(p15ASacB)::$P_{CnBAD}$::IspS401::TT::HMGR::AACT::$P_{BAD}$ (FIG. 1B), *Salix* Sp. isoprene synthase expression plasmid pISP407 (FIG. 1C) and DxpS/IspS expression plasmid pBBR1MCS3-pBAD-His-Bs_DXS_OPT-ISPS (FIG. 1D). Hatched arrows, open reading frames (ORFs); Black arrows, knockin vector homology arms; Cross-hatched arrows, araBAD promoter; IspS, isoprene synthase; TT, transcriptional terminator; Grey arrow, *E. coli* origin of replication

The present invention provides genetically engineered hosts capable of producing hydrocarbons and derivatives thereof via a mevalonate (MVA) pathway as well as methods for production of these hosts and methods for their use in production of hydrocarbons and derivatives thereof.

Accordingly, disclosed herein are recombinant cells comprising an engineered enzymatic pathway that catalyze the conversion of a gas to a hydrocarbon or derivative thereof, compositions and methods for their production, and methods for their use in production of hydrocarbons or derivatives thereof. The compositions and methods disclosed herein provide low cost processes for conversion of industrial gases to chemicals in a fermenter. In the methods of the present invention, recombinant cells are introduced into a fermenter, mixed with gas feedstocks which are enzymatically converted to a hydrocarbon by the recombinant cells, and the hydrocarbon is then separated from the off-gases from the fermenter.

By "recombinant cell" or "recombinant host" as used herein it is meant to encompass any genetically engineered cell or host as described herein and such terms as recombinant, engineered, and genetically engineered are used interchangeably herein.

By "hydrocarbon" or hydrocarbons" as used herein, it is meant to encompass any organic compound comprised of carbons and hydrogens which can be enzymatically synthesized from a gas and is inclusive of saturated as well as unsaturated structures with double or triple bonds formed between carbon atoms, ring structures, salts and derivatives thereof. In one nonlimiting embodiment, the hydrocarbon comprises one or more isoprene units as depicted in Formula I (I)

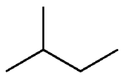

or a salt or derivative thereof.

By the phrase "one or more isoprene units as depicted in Formula I" it is meant to encompass any saturated or unsaturated 5 carbon branched structure derived from an isoprenoid including, isoprene as well as isoprenoids, terpenes and terpenoids as well as derivatives such as, but not limited to isoprenols, and salts thereof.

Nonlimiting examples of hydrocarbons comprising one or more isoprene units produced in accordance with the present invention include isoprene as well as any isoprenoid, terpene or terpenoid derivative of 5, including C5, C10, C15, C20, C25, C30, C35, C40, C45, C50, etc. Nonlimiting examples include hemiterpene, monoterpene, diterpene, triterpene, tetraterpene, polyterpene, lycopene, abietadiene, amorphadiene, carene, alpha-farnesene, beta-farnesene, farnesol, geraniol, geranylgeraniol, isoprene, linalool, limonene, myrcene, nerolidol, ocimene, patchoulol, beta-pinene, sabinene, gamma-terpinene, terpinolene and valencene, as well as derivatives and salts thereof.

The mevalonate pathway for the conversion of acetyl-CoA to the isoprenoid precursors, IPP and DMAPP, is found in eukaryotes, archaea and some bacteria, but is absent from the facultative chemolithoautotrophic bacterium, *Cupriavidus necator* (previously called *Hydrogenomonas eutrophus, Alcaligenes eutropha, Ralstonia eutropha*, and *Wautersia eutropha*). *Cupriavidus* necator is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. *C. necator* does not naturally contain genes for isoprene synthase (ISPS) and therefore does not express this enzyme. Additional properties of *Cupriavidus necator* include microaerophilicity, copper resistance (Makar and Casida; 1987), bacterial predation (Byrd et al., 1985; Sillman & Casida, 1986; Zeph & Casida, 1986) and polyhydrobutyrate (PHB) synthesis. In addition, the cells have been reported to be capable of both aerobic and nitrate dependent anaerobic growth.

In one nonlimiting embodiment, the host of the present invention is *Cupriavidus* necator, such as a genetically engineered strain of *Cupriavidus* necator capable of stable hydrocarbon production. In one nonlimiting embodiment, the present invention relates to *Cupriavidus necator* host capable of producing isoprenoids via a mevalonate (MVA) pathway, such as an isolated or substantially pure genetically engineered *Cupriavidus necator* host capable of producing isoprenoids via a mevalonate (MVA) pathway. A nonlimiting example of a *C. necator* host useful in the present invention is a *C. necator* of the H16 strain. In one nonlimiting embodiment, a *C. necator* host of the H16 strain with the phaCAB gene locus knocked out (ΔphaCAB) is used.

As used herein, a "substantially pure culture" of a recombinant host microorganism is a culture of that microorganism in which less than about 40% (i.e., less than about 35%; 30%; 25%; 20%; 150; 10%; 5%; 2%; 1%; 0.50; 0.250; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In another nonlimiting embodiment, the host of the present invention is a genetically engineered host having one or more of the above-mentioned properties of *Cupriavidus necator.*

In yet another nonlimiting embodiment, the host of the present invention is a genetically engineered host selected from non-pathogenic members of the genera *Ralstonia, Wausteria, Cupriavidus, Alcaligenes, Burkholderia* or *Pandoraea*.

The present invention provides methods and compositions for synthesizing hydrocarbons in these genetically engineered cells. In the methods and compositions of the present invention, a host of the invention, such as organisms such as *C. necator*, as well as non-pathogenic members of the genera *Ralstonia, Wausteria, Alcaligenes, Burkholderia* and *Pandoraea*, and other organisms having one or more of the above-mentioned properties of *Cupriavidus necator* can be used to synthesize hydrocarbons via a mevalonate (MVA) dependent pathway.

Recombinant hosts of the present invention comprise at least one genome-integrated synthetic operon encoding an enzyme of the MVA pathway. Nonlimiting examples of enzymes of this pathway include acetoacetyl-CoA C-acetyltransferase (AACT, EC 2.3.1.9) that catalyzes the chemical reaction 2 acetyl-CoA⇒CoA+acetoacetyl-CoA, HMG-CoA reductase (HMGR, EC 1.1.1.34) that catalyzes the reaction HMG-CoA (3-hydroxy-3-methylglutaryl-CoA)⇒mevalonic acid, hydroxymethylglutaryl-CoA synthase (HMGS, EC 2.3.3.10) that catalyzes the reaction acetoacetyl-CoA⇒HMG-CoA, mevalonate kinase (MVK, EC 2.7.1.36) that catalyzes the reaction mevalonic acid⇒mevalonate-5-phosphate, phosphomevalonate kinase (MPK, EC 2.7.4.2) that catalyzes the reaction mevalonate-5-phosphate⇒mevalonate-5-diphosphate, mevalonate diphosphate decarboxylase (MDD, EC 4.1.1.33) that catalyzes the reaction mevalonate-5-diphosphate⇒isopentyl-5-pyrophosphate, isopentenyl diphosphate isomerase (IDI, EC 5.3.3.2) that catalyzes the reaction isopentyl-5-pyrophosphate⇒dimethylallyl pyrophosphate, and isoprene synthase (ISPS, EC 4.2.3.27) that catalyses the reaction dimethylallyl pyrophosphate⇒isoprene+diphosphate. The host may comprise any one or more of these enzymes, such as at least two or at least three of these enzymes.

In one nonlimiting embodiment, the recombinant host comprises at least two genome-integrated synthetic operons encoding enzymes of the MVA pathway.

In one nonlimiting embodiment, the genetically engineered strain is produced by integration of a synthetic operon encoding one or more enzymes of the upper MVA pathway into the host genome. In one nonlimiting embodiment, the genetically engineered strain is produced by integration of a synthetic operon encoding one or more enzymes of the *Enterococcus faecalis* upper MVA pathway into the host genome.

In one nonlimiting embodiment, the host genome comprises an operon encoding one or more enzymes of the *Enterococcus faecalis* upper MVA pathway. The operon may be a synthetic operon. The operon may be exogenous to the host. One or more of the enzymes may be exogenous to the host. In some non-limiting embodiments, the operon encodes at least one AACT and/or at least one HMGR and/or at least one HMGS. In some non-limiting embodiments, the operon encodes at least one AACT and at least one HMGR and at least one HMGS. In some non-limiting embodiments, the operon includes sequences encoding AACT, HMGR and HMGS, arranged in that order.

Nonlimiting examples of enzymes of upper MVA pathway, genes of which can be integrated into the host genome, include the polypeptides of AACT (e.g. SEQ ID NO:1 and SEQ ID NO:56), HMGR (e.g. SEQ ID NOs: 1, 58, 60, 62, 64 and 66) and HMGS (e.g. SEQ ID NOs:2, 68, 70, 72 and 74) as well as polypeptides with similar enzymatic activities exhibiting at least 70%, 75%, 80, 85, 90%, 91%, 92%, 93%, 94%, 95%, 96%, 97%, 98%, 99% or 99.5% sequence identity to an amino acid sequence set forth in SEQ ID NOs: 1, 56, 58, 60, 62, 64, 66, 2, 68, 70, 72 or 74 or a functional fragment thereof. Nonlimiting examples of nucleic acid sequences encoding such enzymes which can be integrated into the host genome include the nucleic acid sequences of AACT (e.g. SEQ ID NO:23 and SEQ ID NO:55), HMGR (e.g. SEQ ID NOs: 23, 57, 59, 61, 63 and 65) and HMGS (e.g. SEQ ID NO:24, 67, 69, 71 and 73) as well as nucleic acid sequences encoding polypeptides with similar enzymatic activities exhibiting at least 70%, 75%, 80, 85, 90%, 91%, 92%, 93%, 94%, 95%, 96%, 97%, 98%, 99% or 99.5% sequence identity to the nucleic acid sequence set forth in SEQ ID NOs: 23, 55, 57, 59, 61, 63, 65, 24, 67, 69, 71 or 73 or a functional fragment thereof. The host may comprise any one or more of these enzymes, such as at least one AACT and/or at least one HMGR and/or at least one HMGS. In some non-limiting embodiments, the host comprises at least one AACT and at least one HMGR and at least one HMGS. In one nonlimiting embodiment, the nucleic acid sequence is codon optimized for *C. necator* expression.

In one nonlimiting embodiment, the genetically engineered strain is produced by integration of a synthetic operon encoding one or more enzymes of the lower MVA pathway into the host genome. In one nonlimiting embodiment, the genetically engineered strain is produced by integration of a synthetic operon encoding one or more enzymes of the *Streptococcus pneumoniae* lower MVA pathway into the host genome.

In one nonlimiting embodiment, the host genome comprises an operon encoding one or more enzymes of the *Streptococcus pneumoniae* lower MVA pathway. The operon may be a synthetic operon. The operon may be exogenous to the host. One or more of the enzymes may be exogenous to the host. In some non-limiting embodiments, the operon encodes one or more MVK and/or one or more MPK and/or one or more MDD and/or one or more IDI. In some non-limiting embodiments, the operon encodes at least one MVK and at least one MPK and at least one MDD, or encodes at least one MVK and at least one MPK and at least one MDD and at least one IDI. In some non-limiting embodiments, the operon comprises sequences coding for MVK, MPK and MDD, arranged in that order.

Nonlimiting examples of enzymes of the lower MVA pathway, genes of which can be integrated into the host genome, include mevalonate kinase (MVK; e.g. SEQ ID NO:3), phosphomevalonate kinase (MPK; e.g. SEQ ID NO:4), mevalonate diphosphate decarboxylase (MDD; e.g. SEQ ID NO:5) and isopentenyl diphosphate isomerase (IDI; e.g. SEQ ID NO:6) as well as polypeptides with similar enzymatic activities exhibiting at least 70%, 75%, 80, 85, 90%, 91%, 92%, 93%, 94%, 95%, 96%, 97%, 98%, 99% or 99.5% sequence identity to an amino acid sequence set forth in SEQ ID NOs: 3, 4, 5 or 6 or a functional fragment thereof. Nonlimiting examples of nucleic acid sequences encoding such enzymes which can be integrated into the host genome include the nucleic acid sequences of MVK (e.g. SEQ ID NO:25), MPK (e.g. SEQ ID NO:26), MDD (e.g. SEQ ID NO:27) and IDI (e.g. SEQ ID NO:28) as well as nucleic acid sequences encoding polypeptides with similar enzymatic activities exhibiting at least 70%, 75%, 80, 85, 90%, 91%, 92%, 93%, 94%, 95%, 96%, 97%, 98%, 99% or 99.5% sequence identity to the nucleic acid sequence set forth in SEQ ID NOs: 25, 26, 27 or 28 or a functional fragment thereof. The host may comprise any one or more of these enzymes, such as one or more MVK and/or one or more MPK and/or one or more MDD and/or one or more IDI. In some non-limiting embodiments, the host comprises at least one MVK and at least one MPK and at least one MDD, or encodes at least one MVK and at least one MPK and at least one MDD and at least one IDI.

In one nonlimiting embodiment, the nucleic acid sequence is codon optimized for *C. necator* expression.

In one nonlimiting embodiment, the genetically engineered strain comprises a genome-integrated synthetic operon encoding the one or more enzymes of the upper MVA pathway and a genome-integrated synthetic operon encoding one or more enzymes of the lower MVA pathway. In one nonlimiting embodiment, the genetically engineered strain comprises a genome-integrated synthetic operon encoding the one or more enzymes of the *Enterococcus faecalis* upper MVA pathway and a genome-integrated synthetic operon encoding one or more enzymes of the *Streptococcus pneumoniae* lower MVA pathway.

In one non-limiting embodiment, the host comprises any one or more enzymes of the upper MVA pathway as described above and any one or more enzymes of the lower MVA pathway as described above. In some non-limiting embodiments, these enzymes of the upper and/or lower MVA pathway are integrated into the genome of the host.

In one nonlimiting embodiment, the genetically engineered strain is produced by integration of a synthetic operon encoding mevalonate kinase (MK), mevalonate phosphokinase (MPK), and mevalonate decarboxylase (MDD) into the host genome. Nonlimiting examples of mevalonate kinase (MK), mevalonate phosphokinase (MPK), and mevalonate decarboxylase (MDD) enzymes, genes of which can be integrated into the host genome, include the polypeptides of SEQ ID NO: 9, 10, 11, 12, 13, 14, 15, 16, 17, 18, 19, 20, 21 or 22 as well as polypeptides with similar enzymatic activities exhibiting at least 70%, 75%, 80, 85, 90%, 91%, 92%, 93%, 94%, 95%, 96%, 97%, 98%, 99% or 99.5% sequence identity to an amino acid sequence set forth in SEQ ID NOs: 9, 10, 11, 12, 13, 14, 15, 16, 17, 18, 19, 20, 21 or 22 or a functional fragment thereof. Nonlimiting examples of nucleic acid sequences encoding such enzymes which can be integrated into the host genome include the nucleic acid sequences of SEQ ID NO:s 31, 32, 33, 34, 35, 36, 37, 38, 39, 40, 41, 42, 43 or 44 as well as nucleic acid sequences encoding polypeptides with similar enzymatic activities exhibiting at least 70%, 75%, 80, 85, 90%, 91%, 92%, 93%, 94%, 95%, 96%, 97%, 98%, 99% or 99.5% sequence identity to the nucleic acid sequence set forth in SEQ ID NOs: 31, 32, 33, 34, 35, 36, 37, 38, 39, 40, 41, 42, 43 or 44 or a functional fragment thereof.

In one nonlimiting embodiment, the nucleic acid sequence is codon optimized for *C. necator* expression.

In one nonlimiting embodiment, the genetically engineered strain is produced by integration of a synthetic operon comprising SEQ ID NO: 48, 49 or 50.

In some nonlimiting embodiments, the recombinant host further comprises at least one additional plasmid encoding an enzyme of the MVA pathway.

In some nonlimiting embodiments, the recombinant host further comprises a plurality of plasmids expressing enzymes of the lower and/or upper MVA pathway.

In some nonlimiting embodiments, the genetically engineered strain may further comprise a sequence coding for an isoprene synthase enzyme, such as a genome-integrated transcription unit coding for an isoprene synthase enzyme. Nonlimiting examples of isoprene synthase enzymes include the polypeptide sequence of *Populus alba* isoprene synthase (IspS), EC 4.2.3.27 (accession number Q50L36; SEQ ID NO:7), and the polypeptide sequence of *Salix* sp. DG-2011 isoprene synthase (IspS), EC 4.2.3.27 (accession number AEK70970; SEQ ID NO:8) as well as polypeptides with similar enzymatic activities exhibiting at least 70%, 75%, 80, 85, 90%, 91%, 92%, 93%, 94%, 95%, 96%, 97%, 98%, 99% or 99.5% sequence identity to an amino acid sequence set forth in SEQ ID NOs: 7 or 8 or a functional fragment thereof. Nonlimiting examples of nucleic acid sequences encoding such enzymes which can be integrated into the host genome include the nucleic acid sequences of *Populus alba* isoprene synthase (SEQ ID NO:29) and *Salix* sp. Isoprene synthase (SEQ ID NO:30) as well as nucleic acid sequences encoding polypeptides with similar enzymatic activities exhibiting at least 70%, 75%, 80, 85, 90%, 91%, 92%, 93%, 94%, 95%, 96%, 97%, 98%, 99% or 99.5% sequence identity to the nucleic acid sequence set forth in SEQ ID NOs: 29 or 30 or a functional fragment thereof.

In one nonlimiting embodiment, the nucleic acid sequence is codon optimized for *C. necator* expression.

Integration of the transcription unit coding for an isoprene synthase enzyme provides a convenient readout for DMAPP production in the host.

The percent identity (homology) between two amino acid sequences as disclosed herein can be determined as follows. First, the amino acid sequences are aligned using the BLAST 2 Sequences (B12seq) program from the stand-alone version of BLAST containing BLASTP version 2.0.14. This stand-alone version of BLAST can be obtained from the U.S. government's National Center for Biotechnology Information web site (www with the extension ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the polypeptides or nucleic acid sequences described herein can also be used in the methods of the document. The term "functional fragment" as used herein refers to a peptide fragment of a polypeptide or a nucleic acid sequence fragment encoding a peptide fragment of a polypeptide that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, polypeptide. The functional fragment can generally, but not always, be comprised of a continuous region of the polypeptide, wherein the region has functional activity.

Methods of the present invention can be performed in a host as described herein, such as a recombinant *Cupriavidus necator* host, as well as non-pathogenic members of the genera *Ralstonia, Wausteria, Alcaligenes, Burkholderia* and *Pandoraea*, and other organisms having one or more of the above-mentioned properties of *Cupriavidus necator.*

Recombinant hosts can naturally express none or some (e.g., one or more, two or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, engineered cells, genetically engineered cells, genetically engineered hosts or engineered hosts. Thus, as described herein, recombinant hosts can include exogenous nucleic acids encoding one or more of enzymes of the MVA pathway, as described herein. The recombinant host of the invention may be any genetically engineered cell or host as described herein.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

The utility of the MVA pathway for stable hydrocarbon production in *Cupriavidus necator* was evaluated in a genetically engineered strain containing two genome-integrated synthetic operons encoding the *Enterococcus faecalis* upper MVA pathway and *Streptococcus pneumoniae* lower MVA pathway, with a third genome-integrated transcription unit coding for the *Populus alba* isoprene synthase (IspS, EC 4.2.3.27) to provide a convenient readout for DMAPP production.

The *E. faecalis* upper MVA pathway and the *S. pneumoniae* lower MVA pathway were integrated into the *C. necator* H16 genome by homologous recombination as two arabinose-inducible operons, together with a third synthetic gene encoding *P. alba* isoprene synthase to provide a readout for DMAPP production. The resulting strain, BDISC_0921, was transformed with plasmid pISP407 expressing a second isoprene synthase gene from *Salix* Sp., to ensure there was sufficient in vivo isoprene activity to draw carbon flux though the MVA pathway. BDISC_0921 and its plasmid-containing derivative, BDISC_0990, were tested in an isoprene/mevalonolactone bioassay against a *C. necator* strain with enhanced DMAPP production through the overexpression of the non-mevalonate pathway enzyme, DxpS, and a control strain, BDISC_0913, containing only the upper MVA pathway with the *P. alba* IspS.

Figure 2A:
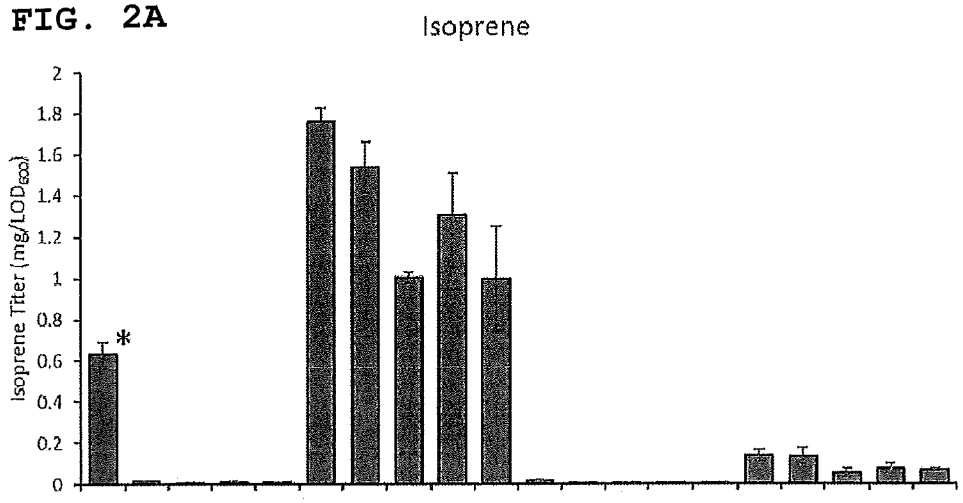
FIGS. 2A and 2B shows de novo synthesis of isoprene and mevalonolactone in *C. necator* strains encoding genome-integrated gene copies of the *E. faecalis* upper MVA pathway and the *S. pneumoniae* lower MVA pathway. *C. necator* MVA pathway strains and control strains were cultured at 30° C. for 24 hours in 10 ml GC-MS vials containing 2 ml of defined media with different ammonium chloride concentrations. Isoprene was measured in the headspace and mevalonolactone was measured in the culture supernatant by GC-MS (n=3 except for bars with an asterix where n=2). Measurements were normalized to culture optical density ($OD_{600}$). Error bars represent Standard Deviation of the mean. ND, not done.
Figure 2B:
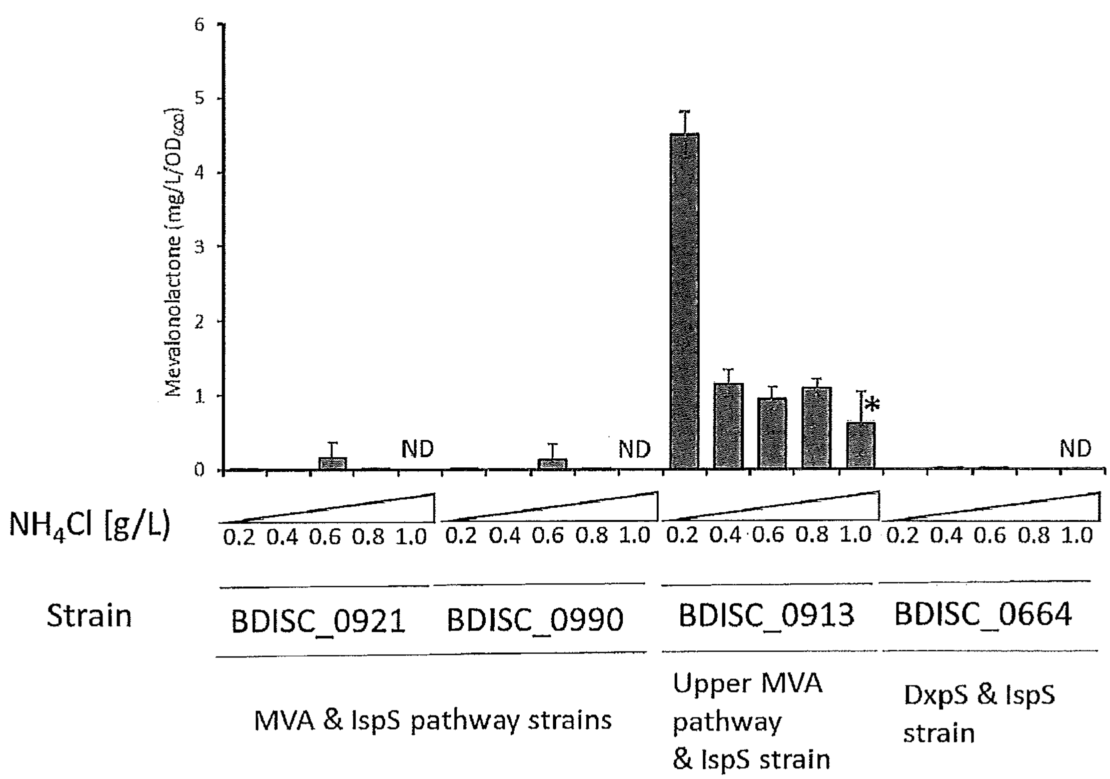
Figure 3:
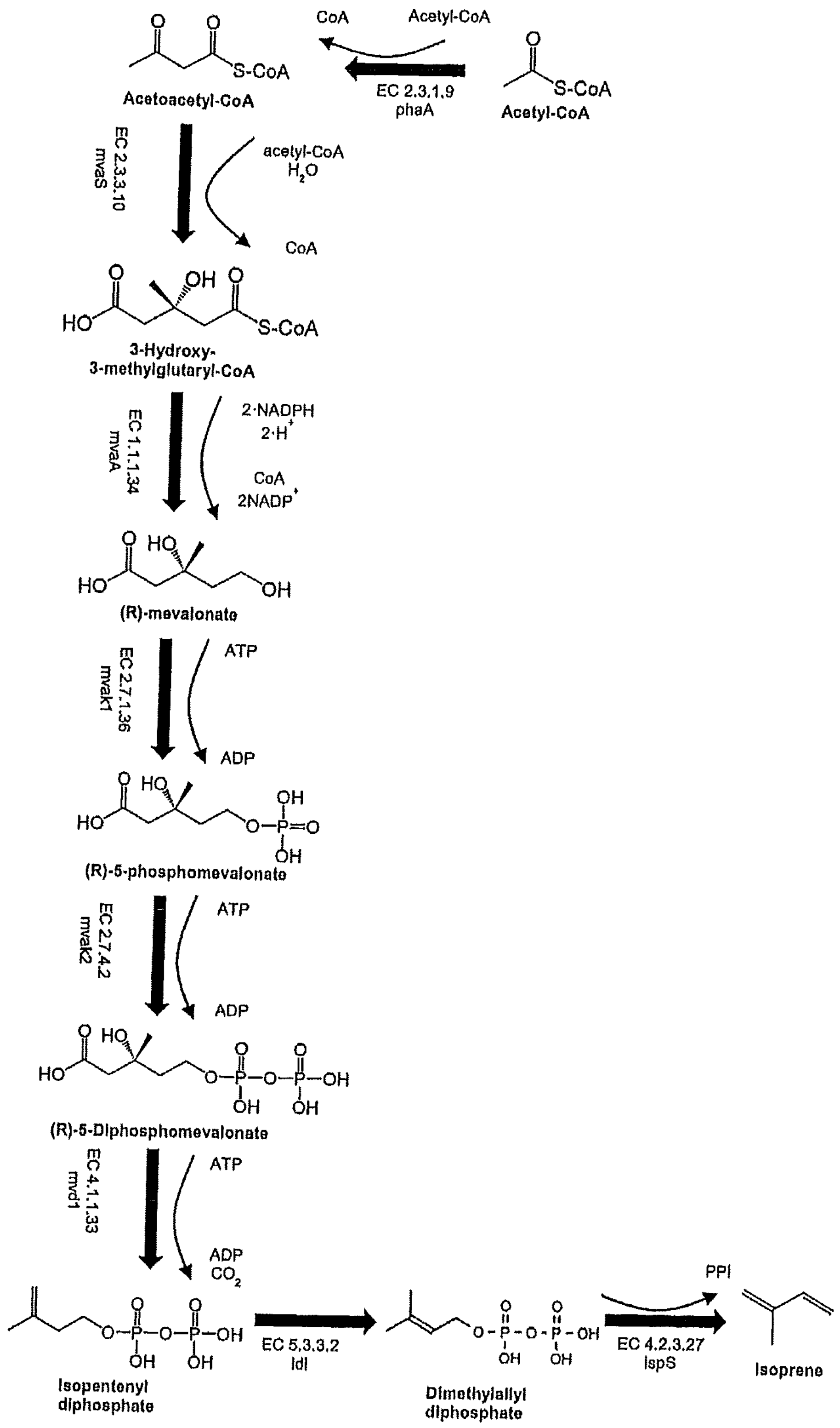
FIG. 3 is a schematic of the MVA pathway.

To create a utilizable pool of acetyl-CoA for the mevalonate pathway, the isoprene and mevalolactone bioassays were performed under nutrient-limitation conditions to induce the *C. necator* stringent response (Brigham et al. 2012). Following induction of the MVA/MEP pathway enzymes with arabinose, the strains were cultured for 24 hours in a titration series of defined media containing progressively lower concentrations of the main nitrogen source, ammonium chloride (See FIG. 2A). Of the strains tested, the two MVA pathway strains, BDISC_0921 and BDISC_0990, produced the highest isoprene titers of 0.63 and 1.76 mg/L/$OD_{600}$, respectively, in media with the lowest ammonium chloride concentration of 0.2 g/L (see FIG. 2A). By contrast, isoprene production from the MEP pathway strain, BDISC_0664, was significantly lower, ranging from 0.05-0.23 mg/L/$OD_{600}$ (see FIG. 2A). Mevalonolactone was only detectable above 1 mg/L in BDISC_0913, containing a genome-integrated copy of the upper MVA pathway in the absence of the mevalonate-consuming lower MVA pathway (see FIG. 2B). As with isoprene production in the full MVA pathway strains, BDISC_0913 produced the highest mevalonolactone titre, of 4.5 mg/L/$OD_{600}$, with 0.2 g/L ammonium chloride. Both the isoprene and mevalonolactone assay results are consistent with higher carbon flux going through the MVA pathway under nitrogen-limitation conditions used to induce the *C. necator* stringent response. Taken together these results confirm that the genome-integrated gene copies of the *E. faecalis* upper MVA pathway and the *S. pneumoniae* lower MVA pathway are functional in *C. necator* and are able to support the detectable bioconversion of acetyl-CoA from central metabolism to isoprene.

Further, several l-MVA variants were identified as being particularly effective in producing hydrocarbons as well. Nucleic acid sequences used in identifying these variants include SEQ ID NO: 45, 46 and 47. The identified l-MVA variants comprise the following combination of genes.

| | MK | MPK | MDD |
|---|---|---|---|
| l-MVA-9 | *M. mazei* | *S. cerevisiae* | *S. cerevisiae* |
| l-MVA-11 | *S. pneumoniae* | *S. pneumoniae* | *S. pneumoniae* |
| l-MVA-12 | *S. pneumoniae* | *Lactococcus lactis* | *S. pneumoniae* |

The full sequences of the operons for l-MVA-9, l-MVA-11 and lMVA-12 are depicted in SEQ ID NO:s 48, 49 and 50, respectively.

Thus, the present invention also provides methods for hydrocarbon production.

In a non-limiting embodiment, a method of hydrocarbon production as described herein is carried out using any host of the invention.

In a non-limiting embodiment is provided the use of a host of the invention, such as a recombinant or genetically engineered host as described herein, for the production of a hydrocarbon. The use may involve any method of hydrocarbon production as described herein.

In one nonlimiting embodiment the hydrocarbon produced from the genetically engineered host comprises one or more isoprene units as depicted in Formula I (I)

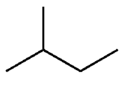

or a salt or derivative thereof.

Methods of the present invention can be performed in a recombinant *Cupriavidus necator* host, as well as non-pathogenic members of the genera *Ralstonia, Wausteria, Alcaligenes, Burkholderia* and *Pandoraea*, and other organisms having one or more of the above-mentioned properties of *Cupriavidus necator.*

In one nonlimiting embodiment, the method comprises enzymatically converting mevalonate to isopentenyl-pyrophosphate in a genetically engineered host as described herein.

In one nonlimiting embodiment, the hydrocarbon production method is performed using a genetically engineered host comprising at least one genome-integrated synthetic operon encoding an enzyme of the MVA pathway. Nonlimiting examples of enzymes of this pathway include acetoacetyl-CoA C-acetyltransferase (AACT), HMG-CoA reductase (HMGR), hydroxymethylglutaryl-CoA synthase (HMGS), mevalonate kinase (MVK), phosphomevalonate kinase (MPK), mevalonate diphosphate decarboxylase (MDD), isopentenyl diphosphate isomerase (IDI) and isoprene synthase (ISPS).

In one nonlimiting embodiment, the hydrocarbon production method is performed using a genetically engineered host comprising at least two genome-integrated synthetic operons encoding enzymes of the MVA pathway.

In one nonlimiting embodiment, the hydrocarbon production method is performed using a genetically engineered host comprising a synthetic operon encoding one or more enzymes of the upper MVA pathway into the host genome. In one nonlimiting embodiment, the hydrocarbon production method is performed using a genetically engineered host comprising a synthetic operon encoding one or more enzymes of the *E. faecalis, C. necator, S. cerevisiae, L. monocytogenes, S. pneumonia, L. lactis* or *S. aureus* upper MVA pathway into the host genome. In this embodiment, any of the nucleic acid sequences encoding a polypeptide having AACT (e.g. SEQ ID NO:1 and SEQ ID NO:56), HMGR (e.g. SEQ ID NOs: 1, 58, 60, 62, 64 and 66) and HMGS (e.g. SEQ ID NOs:2, 68, 70, 72 and 74) as well as polypeptides with similar enzymatic activities exhibiting at least 70%, 75%, 80, 85, 90%, 910, 92%, 93%, 94%, 95%, 96%, 97%, 98%, 99% or 99.5% sequence identity to an amino acid sequence set forth in SEQ ID NOs: 1, 56, 58, 60, 62, 64, 66, 2, 68, 70, 72 or 74 or a functional fragment thereof. as described supra can be used. Nonlimiting examples of nucleic acid sequences encoding such enzymes which can be integrated into the host genome include the nucleic acid sequences of AACT (e.g. SEQ ID NO:23 and SEQ ID NO:55), HMGR (e.g. SEQ ID NOs: 23, 57, 59, 61, 63 and 65) and HMGS (e.g. SEQ ID NO:24, 67, 69, 71 and 73) as well as nucleic acid sequences encoding polypeptides with similar enzymatic activities exhibiting at least 70%, 75%, 80, 85, 90%, 91%, 92%, 93%, 94%, 95%, 96%, 97%, 98%, 99% or 99.5% sequence identity to the nucleic acid sequence set forth in SEQ ID NOs: 23, 55, 57, 59, 61, 63, 65, 24, 67, 69, 71 or 73 or a functional fragment thereof.

In one nonlimiting embodiment, the hydrocarbon production method is performed using a genetically engineered host comprising a synthetic operon encoding one or more enzymes of the lower MVA pathway into the host genome. In one nonlimiting embodiment, the hydrocarbon production method is performed using a genetically engineered host comprising a synthetic operon encoding one or more enzymes of the *Streptococcus pneumoniae* lower MVA pathway into the host genome. In this embodiment, any of the nucleic acid sequences encoding a polypeptide having mevalonate kinase (MVK; e.g. SEQ ID NO:3), phosphomevalonate kinase (MPK; e.g. SEQ ID NO:4), mevalonate diphosphate decarboxylase (MDD; e.g. SEQ ID NO:5) or isopentenyl diphosphate isomerase (IDI; e.g. SEQ ID NO:6) activity or a polypeptide with similar enzymatic activities exhibiting at least 70%, 75%, 80, 85, 90%, 91%, 92%, 93%, 94%, 95%, 96%, 97%, 98%, 99% or 99.5% sequence identity to an amino acid sequence set forth in SEQ ID NOs: 3, 4, 5 or 6 or a functional fragment thereof as described supra can be used.

In another nonlimiting embodiment, the method is performed using a genetically engineered host comprising one or more exogenous nucleic acid sequences encoding one or more enzymes of the upper MVA pathway and one or more exogenous nucleic acid sequences encoding one or more enzymes of the lower MVA pathway. In one nonlimiting embodiment, the method is performed using a genetically engineered host comprising one or more exogenous nucleic acid sequences encoding one or more enzymes of the *Enterococcus faecalis* upper MVA pathway as described supra and one or more exogenous nucleic acid sequences encoding one or more enzymes of the *Streptococcus pneumoniae* lower MVA pathway as described supra.

In another nonlimiting embodiment, the hydrocarbon production method is performed using a genetically engineered strain produced by integration of a synthetic operon encoding mevalonate kinase (MK), mevalonate phosphokinase (MPK), and mevalonate decarboxylase (MDD) into the host genome. In this embodiment, any of the nucleic acid sequences encoding a mevalonate kinase (MK), mevalonate phosphokinase (MPK), and/or mevalonate decarboxylase (MDD) enzyme including the polypeptides of SEQ ID NO: 9, 10, 11, 12, 13, 14, 15, 16, 17, 18, 19, 20, 21 or 22 or polypeptides exhibiting similar enzymatic activities exhibiting at least 70%, 75%, 80, 85, 90%, 91%, 92%, 93%, 94%, 95%, 96%, 97%, 98%, 99% or 99.5% sequence identity to an amino acid sequence set forth in SEQ ID NOs: 9, 10, 11, 12, 13, 14, 15, 16, 17, 18, 19, 20, 21 or 22 or a functional fragment thereof as described supra can be used.

In one nonlimiting embodiment, the hydrocarbon production method is performed using a genetically engineered strain comprising a nucleic acid sequence codon optimized for *C. necator* expression.

In one nonlimiting embodiment, the hydrocarbon production method is performed using a genetically engineered strain comprising a synthetic operon comprising SEQ ID NO: 48, 49 or 50.

In some nonlimiting embodiments, the hydrocarbon production method is performed using a genetically engineered strain further comprising at least one additional plasmid encoding an enzyme of the MVA pathway.

In some nonlimiting embodiments, the hydrocarbon production method is performed using a genetically engineered strain further comprising a plurality of plasmids expressing enzymes of the lower and/or upper MVA pathway.

In some nonlimiting embodiments, the genetically engineered strain used in the hydrocarbon production methods may further comprise a genome-integrated transcription unit coding for an isoprene synthase enzyme as described supra.

In some non-limiting embodiments, the method comprises contacting a host of the invention with a suitable substrate under conditions such that the host is capable of producing a hydrocarbon from the substrate via a MVA pathway. Such a method may comprise culturing a host of the invention in the presence of a suitable substrate. In some non-limiting embodiments, the substrate is acetyl-CoA, or a substrate that can be converted to form acetyl-CoA by the host.

In any the methods described herein, a fermentation strategy can be used that entails anaerobic, micro-aerobic or aerobic cultivation. A fermentation strategy can entail nutrient limitation such as nitrogen, phosphate or oxygen limitation. A cell retention strategy using a ceramic hollow fiber membrane can be employed to achieve and maintain a high cell density during fermentation. The substrate, or the principal carbon source fed to the fermentation, can be or can derive from a biological or non-biological feedstock. The biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue (NVR) a caustic wash waste stream from cyclohexane oxidation processes or waste stream from a chemical industry such as, but not limited to a carbon black industry or a hydrogen-refining industry, or petrochemical industry.

In one nonlimiting embodiment, at least one of the enzymatic conversions of the hydrocarbon production method comprises gas fermentation within the recombinant *Cupriavidus necator* host, or a non-pathogenic member of the genera *Ralstonia, Wausteria, Alcaligenes, Burkholderia* and *Pandoraea*, and other recombinant organism having one or more of the above-mentioned properties of *Cupriavidus necator*. In this embodiment, the gas fermentation may comprise at least one of natural gas, syngas, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO_2/H_2$.

In some non-limiting embodiments the substrate is a gas. In some non-limiting embodiments, the method comprises contacting the host with a gas. In some of these embodiments, the gas comprises at least one of natural gas, syngas, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one non-limiting embodiment, the gas comprises $CO_2/H_2$.

The methods of the present invention may further comprise recovering produced hydrocarbons from the recombinant host. In these embodiments, the hydrocarbons may comprise one or more isoprene units, as described herein.

In some non-limiting embodiments, the hydrocarbon produced by a method of the invention is a gas. In some non-limiting embodiments the method further comprises recovering produced gaseous hydrocarbon from the host.

Once produced, any method can be used to isolate hydrocarbons. For example, hydrocarbons can be recovered from the fermenter off-gas stream as a volatile product as the boiling point of isoprene is 34.1° C. At a typical fermentation temperature of approximately 30° C., hydrocarbons have a high vapor pressure and can be stripped by the gas flow rate through the broth for recovery from the off-gas. Hydrocarbons can be selectively adsorbed onto, for example, an adsorbent and separated from the other off-gas components. Membrane separation technology may also be employed to separate hydrocarbons from the other off-gas compounds. Hydrocarbons may be desorbed from the adsorbent using, for example, nitrogen and condensed at low temperature and high pressure.

Because of the gaseous nature of isoprene, in embodiments of the present invention wherein the hydrocarbon produced is isoprene, an advantage is easy separation of the product.

Also provided by the present invention are hydrocarbons bioderived from, produced by, or obtainable from, a recombinant host according to any of methods described herein. In one nonlimiting embodiment, the hydrocarbon has carbon isotope ratio that reflects an atmospheric carbon dioxide uptake source. Examples of such ratios include, but are not limited to, carbon-12, carbon-13, and carbon-14 isotopes.

In addition, the present invention provides a product such as a bio-derived, bio-based, or fermentation-derived product produced using the methods and/or compositions disclosed herein. Examples of such products include, but are not limited to, compositions comprising at least one bio-derived, bio-based, or fermentation-derived compound or any combination thereof, as well as polymers, rubbers such as cis-polyisoprene rubber, trans-polyisoprene rubber, or liquid polyisoprene rubber, molded substances, formulations and semi-solid or non-semi-solid streams comprising one or more of the bio-derived, bio-based, or fermentation-derived compounds or compositions, combinations or products thereof.

In addition, the present invention provides methods of producing such a product. In some non-limiting embodiments, the method comprises producing a hydrocarbon by a method of the invention and converting the hydrocarbon to said product. In one non-limiting embodiment, a method of producing a polymer comprises the steps of producing a hydrocarbon by a method as described herein and forming a polymer from said hydrocarbon.

Although specific advantages have been enumerated above, various embodiments may include some, none, or all of the enumerated advantages. Further, other technical advantages may become readily apparent to one of ordinary skill in the art after review of the figures and description herein. It should be understood at the outset that, although exemplary embodiments are illustrated in the figures and described herein, the principles of the present disclosure may be implemented using any number of techniques, whether currently known or not. The present disclosure should in no way be limited to the exemplary implementations and techniques illustrated in the drawings and described herein.

Unless otherwise specifically noted, articles depicted in the drawings are not necessarily drawn to scale.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The following section provides further illustration of the methods and compositions of the present invention. These working examples are illustrative only and are not intended to limit the scope of the invention in any way.

EXAMPLES

Example 1: Gene Selection

The MVA pathway was assembled in *C. necator* from genes encoding the enzymes of the *E. faecalis* upper MVA pathway (AACT and HMGR) and *S. pneumoniae* lower MVA pathway (MVK, MPK, MDD and IDI). The performance of the *E. faecalis/S. pneumoniae* mevalonate pathway was monitored in live *C. necator* cells by converting DMAPP to isoprene with truncated versions of the *Populus alba* and *Salix* sp. DG-2011 isoprene synthase (IspS, EC 4.2.3.27), each containing a deletion of residues 1 to 36 encoding plastidic targeting sequences. Synthetic genes encoding these enzymes were codon optimized for expression in *C. necator* (see polypeptide and nucleotide sequences in Appendices 1 and 2).

Figure 1B:
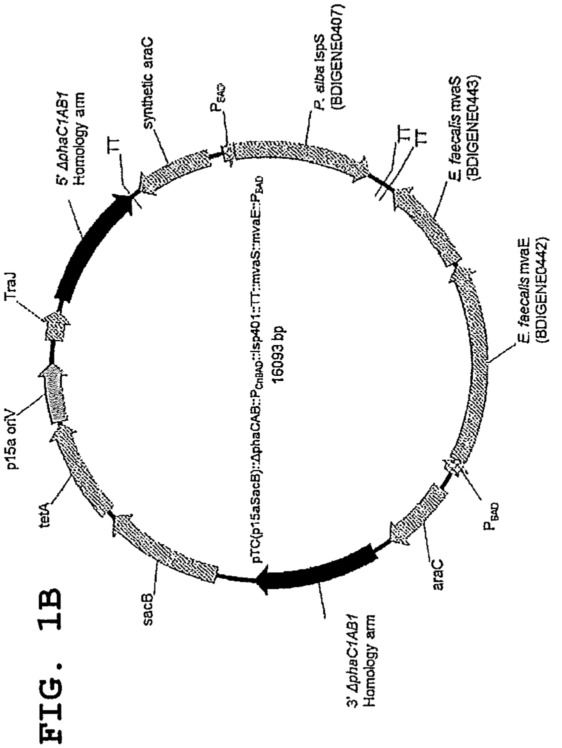

Example 2: Construction of the *C. necator* Genome-Integrated MVA Pathway Strain Two knockin vectors were assembled for the targeted integration of the *E. faecalis* upper MVA pathway, the *S. pneumoniae* lower MVA pathway and *P. alba* isoprene synthase into the *C. necator* genome. Plasmid pTc (ColE1SacB)::ΔphaB2C2::$P_{BAD}$::*S. pneumoniae* L-MVA (FIG. 1A) consisted of a synthetic operon encoding the *S. pneumoniae* lower MVA pathway (MVK, MPK, MDD) under the control of the araBAD promoter, flanked by 1 kb homology arms to the surrounding genes of phaB2C2 locus. When introduced into *C. necator* H16 by conjugation, the knockin vector was designed to integrate the lower MVA pathway at the phaB2C2 locus of chromosome 1 by homologous recombination and delete the phaB2C2 operon. The second knockin vector, pTC (p15ASacB)::ΔphaCAB::$P_{CnBAD}$::IspS401::TT::HMGR::AACT::$P_{BAD}$ (FIG. 1B), consisted of separate transcription units coding for the *E. faecalis* upper MVA pathway and *P. alba* isoprene synthase under the control two facing $P_{BAD}$ promoters, flanked by 1.5 kb homology arms to the phaC1AB1 locus. The *P. alba* IspS/*E. faecalis* upper MVA pathway double promoter cassette was designed to integrate at the phaC1AB1 locus on chromosome 1 and delete the phaC1AB1 operon encoding essential enzymes of the competing polyhydroxyalkanoate (PHA) pathway.

Figure 1C:
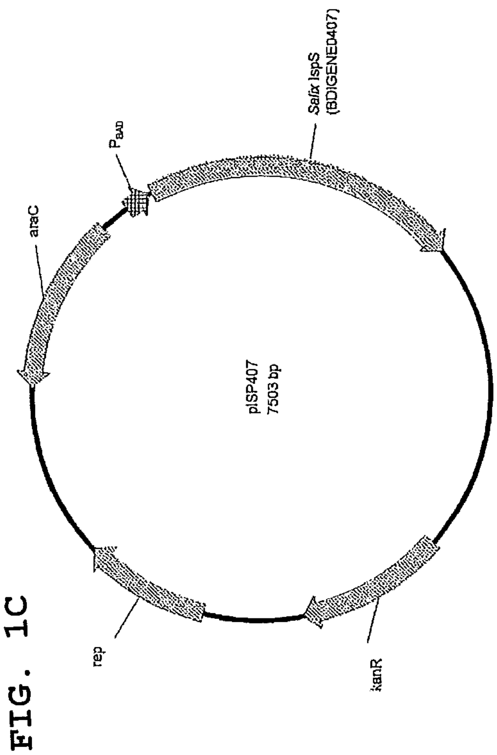
Figure 1D:
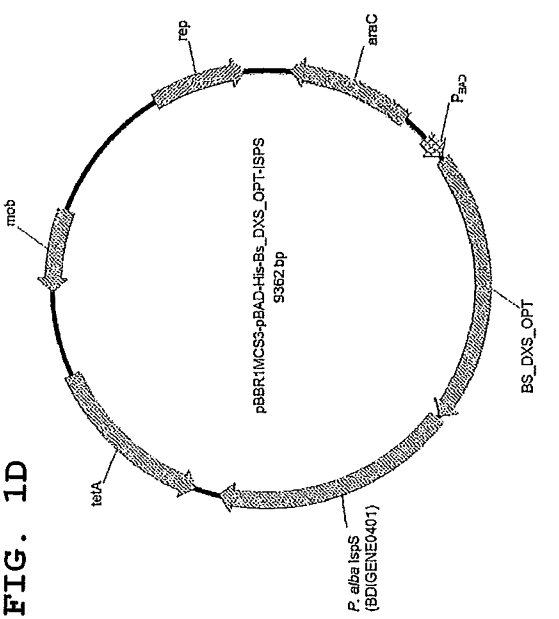

The knockin vectors were introduced into *C. necator* H16 by conjugation, essentially as described by Slater et al., 1998. *C. necator* exconjugants derived from single crossover events were selected on defined medium (1.15 g/L $KH_2PO_4$; 1.15 g/L $Na_2HPO_4$; 1 g/L $NH_4Cl$; 0.5 g/L $MgSO_4.7H_2O$; 0.062 g/L $CaCl_2.2H_2O$; 2 g/L fructose; 15 mg/L $FeSO_4.7H_2O$; 2.4 mg/L $MnSO_4.H_2O$; 2.4 mg/L $ZnSO_4.7H_2O$; 0.48 mg/L $CuSO_4.5H_2O$) supplemented with 20 μg/ml tetracycline. Marker recovery was then performed by sacB counter-selection on LB agar plates supplemented with 10% w/v sucrose and 2% w/v fructose. For the construction of the genome-integrated MVA pathway strain, the *S. pneumoniae* lower MVA pathway was first integrated into wild type *C. necator* H16. Following marker recovery, sucrose-resistant colonies were genotyped by colony PCR with primers BDIPRIM 4874 and 4875 (Table 1), to confirm the correct insertion of the $P_{BAD}$::L-MVA pathway operon at the phaB2C2 locus. A PCR-positive clone containing the ΔphaC1AB1::$P_{BAD}$::L-MVA pathway insertion was then mated with an *E. coli* S17-1 donor strain containing plasmid pTC(p15ASacB)::ΔphaCAB::$P_{CnBAD}$::IspS401::TT::HMGR::AACT::$P_{BAD}$. Following a second round of sacB counter-selection, sucrose-resistant colonies displaying a PHA-deficient visual phenotype were genotyped by colony PCR with primers BDIPRIM 2496 and 2543 (Table 1), to confirm the correct insertion of the IspS/U-MVA pathway cassette at the phaC1AB1 locus. The resulting genome-integrated MVA pathway strain, BDISC_0921, was evaluated against two control strains, BDISC_0913 containing just the *E. faecalis* upper MVA pathway and IspS cassette integrated at the phaC1AB1 locus and a plasmid-based strain, BDISC_0664 (*C. necator* H16 ΔphaC1AB1::pBBR1MCS3-pBAD-His-Bs_DXS_OPT-ISPS, FIG. 1D) expressing *P. alba* IspS and *Bacillus subtilis* MEP pathway enzyme 1-deoxy-D-xylulose-5-phosphate synthase, DxpS (EC 2.2.1.7), from an arabinose-inducible promoter. To increase isoprene titers from the genome-integrated MVA pathway, plasmid pISP407 (FIG. 1C), expressing a second arabinose-inducible isoprene synthase (*Salix* Sp. DG-2011 IspS), was introduced into BDISC_0921 by electroporation, creating *C. necator* strain BDISC_0990 (BDISC_0921::pISP407).

Example 3: Primers

Table 1 provides the amplification primers used for genotyping *C. necator* H16 ΔphaB2C2 and ΔphaC1AB1 gene knockin strains.

TABLE 1

| Primer No | Description | | Primer Sequence |
|---|---|---|---|
| BDIPRIM4874 | *C. necator* H16 ΔphaB2C2 | F | GAGAGCCGGCTGACATAGAC (SEQ ID NO: 51) |
| BDIPRIM4875 | Knockout/Knockin genotyping primers | R | CGGCGACCTATGAGATCACT (SEQ ID NO: 52) |
| BDIPRIM2496 | *C. necator* H16 ΔphaC1AB1 | F | AGAAGGCTGGGACGAAGTCT (SEQ ID NO: 53) |
| BDIPRIM2543 | Knockout/Knockin genotyping primers | R | CAAATTTCCGACCGCTGGTATTC (SEQ ID NO: 54) |

Example 4: De Novo Isoprene and Mevalonate Production from the *C. necator* Genome-Integrated MVA Pathway Strain The genome-integrated MVA pathway strains, BDISC_0921 and BDISC_0990 (BDISC_0921::pISP407), were evaluated for de novo isoprene and mevalonolactone synthesis against control strains BDISC_0913 and BDISC_0664 in bioassays based on gas chromatography-mass spectrometry (GC-MS). To maximize the carbon flux into the MVA pathway, the isoprene and mevalonolactone bioassays were performed in defined media under nitrogen limitation conditions similar to those used for PHA production (Ishizaki, 2001). The optimal carbon to nitrogen ratio for isoprene/mevalonolactone production was tested by performing the bioassays in defined media with different ammonium chloride concentrations, ranging from 0.2 to 1.0 g/L.

Seeding cultures were prepared for each strain by inoculating a single colony into 20 ml of 27.5 g/L Tryptone Soya broth without Dextrose (TSB-D media, Sigma Aldrich catalogue number T3938-500G) containing the appropriate antibiotic when necessary. The seeding cultures were incubated at 30° C., 230 rpm for 48 hours, then diluted by 1 in 50 into fresh TSB-D media (10 ml) in 50 ml sterile Falcon tubes and incubated for approximately 6 hours at 30° C., 230 rpm. MVA pathway and isoprene synthase expression was induced by adding arabinose to a final concentration of 1% w/v and the cultures were incubated for a further 16 hours (overnight) at 30° C., 230 rpm. The cultures were pelleted by centrifugation at 6000 g for 20 minutes and wet cell weight was measured for each cell pellet. The density of each culture was normalized to 0.1 g WCW/ml by re-suspending the *C. necator* cells with the appropriate volume of defined media (1.15 g/L $KH_2PO_4$; 1.15 g/L $Na_2HPO_4$; 0.5 g/L $MgSO_4.7H_2O$; 0.062 g/L $CaCl_2.2H_2O$; 2 g/L fructose; 15 mg/L $FeSO_4.7H_2O$; 2.4 mg/L $MnSO_4.H_2O$; 2.4 mg/L $ZnSO_4.7H_2O$; 0.48 mg/L $CuSO_4.5H_2O$) containing each of the $NH_4Cl$ concentrations tested (0.2, 0.4, 0.6, 0.8, 1 g/L). For each experimental variable (strain and $NH_4Cl$ concentration), separate isoprene and mevalolactone bioassays were set up in triplicate in 10 ml GC-MS vials containing 2 ml fresh defined media (with 1% w/v arabinose and appropriate antibiotics) and 40 μl of 0.1 g WCW/ml of either BDISC_0921, BDISC_0990, BDISC_0913 or BDISC_0664.

For the isoprene bioassay, an isoprene calibration series was set up in 10 ml GC-MS vials containing 1990 μl defined media with 10 μl of 20 ppm to 1000 ppm of isoprene standards dissolved in 0.5% v/v methanol at 4° C. To test isoprene assay robustness and precision, spike-recovery vials were also set up containing 10 μl of 1 ppm isoprene, for a random selection of the experimental conditions tested (one randomly selected strain for each $NH_4Cl$ concentration set up in duplicate). All vials (isoprene/mevalonolactone experimental, isoprene standard and spike recovery vials) were incubated at 30° C., 160 rpm, for 24 hours.

Example 5: Measurement of Headspace Isoprene Concentrations

Headspace isoprene measurements were performed by GC-MS on an Agilent Technologies 7890B gas chromatograph connected to an Agilent quadrupole 5977A MSD instrument with an electronically controlled split/split-less injection port. The instrument was equipped with a dual head MPS autosampler (Gerstel) for head Space analysis. GC separation was performed on a db-624 capillary column (60 m×0.25 mm×1.4 μm J&W Scientific). The GC-MS parameters were as described in table 2. The M-1 ion was used for isoprene quantification.

TABLE 2

GCMS parameters for the measurement of head space isoprene concentrations
GCMS CONDITIONS

| PARAMETER | VALUE | |
|---|---|---|
| Carrier Gas | Helium at constant flow (2.0 ml/min) | |
| Injector | Split ratio | Split 10:L |
| | Temperature | 150° C. |
| Detector | Source Temperature | 230° C. |
| | Quad Temperature | 150° C. |
| | Interface | 260° C. |
| | Gain | 1 |
| | Scan Range | m/z 28-200 |
| | Threshold | 150 |
| | Scan Speed | 4 |
| | 2^2 (A/D samples) | |
| | Sampling Rate | |
| | 2^n = 2^2 | |
| | Mode | SCAN and SIM |
| Solvent delay * | 5.50 min | |
| Oven Temperature | Initial T: 40° C. × 6.9 min | |
| Oven Ramp | 120° C./min to 260° C. for 6 min | |
| Injection volume | 500 μl from the HS in the GC 2 ml vial | |
| Incubation time and T | 13 min at 95° C. | |
| Agitator | ON 500 rpm | |
| Injection volume | 500 μl of the Head Space | |
| Gas saver | On after 2 min | |
| Concentration range (μg/ml) | 0.1-5.0 | |
| GC Column | DB-624 122-1334 Agilent (60 m × 250 μm × 1.4 μm) | |

Example 6: Measurement of Culture Mevalolactone Concentrations

Culture broths were clarified by centrifugation 10,000 g for 10 minutes. The resulting supernatant (0.4 ml) was acidified with 0.2 mL 0.5 M HCl, vortex for 10s and agitated at 1400 rpm for 15 minutes to convert all the mevalonic acid into mevalonolactone. The mevalonolactone was extracted from the aqueous phase by the addition of 0.5 ml of MTBE ((Methyl tertiary butyl ether) and the samples were wortex for 10s agitated at 1400 rpm for a further 30 minutes. The MTBE used for the extraction contained an internal standard, carophyllene, at a concentration 10 ppm, for data normalisation (Pitera et al., 2006). A Thermomixer from Eppendorf was used for the 2 agitation spets. A mevalonolactone calibration series was set up by a diluting mevalonolactone standard in 400 µl of defined media to final concentrations ranging from 1.5625 ppm to 100 ppm. To test assay robustness, spike recovery samples were set up with selected samples. All samples, including the standards were treated in the same way. Following extraction, but leaving both phases in the same vial, 2 µl of the top layer was injected onto the GCMS. The GCMS parameters used to measure mevalonolactone are presented in Table 3. The presence of mevalonolactone in samples was confirmed by comparison of retention time and ion ratios (Table 4) to those of the mevalonolactone standards, with the ion—43 m/z being selected for quantification. All data from standards and samples were normalised to the internal standard caryophyllene (selected ion—93 m/z).

TABLE 3

GCMS parameters for the measurement of culture mevalonolactone concentrations
GCMS CONDITIONS

| PARAMETER | VALUE | |
|---|---|---|
| Carrier Gas | Helium at constant flow (1.0 ml/min) | |
| Injector | Split ratio | Split less |
| | Temperature | 230° C. |
| Detector | Source Temperature | 230° C. |
| | Quad Temperature | 150° C. |
| | Interface | 270° C. |
| | Gain | 2 |
| | Scan Range | m/z 30-300 |
| | Threshold | 150 |
| | Scan Speed | 4 |
| | 2^2 (A/D samples) | |
| | Sampling Rate | |
| | 2^n = 2^2 | |
| | Mode | SCAN and SIM |
| Solvent delay * | 7.0 min | |
| Oven Temperature | Initial T: 90° C. × 2 min | |
| Oven Ramp | 60° C./min to 260° C. for 12 min | |
| Injection volume | 2 µl from the op organic layer in the 2 ml GC vial | |
| Gas saver | On after 2 min | |
| Concentration range (µg/ml) | 1.5625-100 | |
| GC Column | DB-624 (60 m × 250 m × 1.4 µm) | |

Ions used for analysis and quantification of mevalonolactone and the internal standard (caryophyllene) in selected ion monitoring (SIM) acquisition mode are listed in Table 4.

TABLE 4

Ions used for mevalolactone and the internal standard (caryophyllene) for quantitation in selected ion monitoring (SIM) acquisition mode

| Compound | Ions monitored in SIM Mode (m/z) |
|---|---|
| Mevalonolactone | 43, 58, 71 |
| Internal standard - Caryophyllene | 79, 91, 133 |

Example 7: Preparation of l-MVA Variants

Chemically competent cells were transformed with variants of the l-MVA pathway which were designed to be arranged as single operons under the control of the wild type $P_{BAD}$ promoter. The DNA assembly protocol used for this purpose was an optimized single-step overlap-extension PCR strategy. All operons contained the following genes in this specific order: i) mevalonate kinase (MVK), ii) mevalonate phosphokinase (MPK) and iii) mevalonate decarboxylase (MDD). Specifically, PCR products corresponding to each of the individual genes (MK, MPK and MDD, polypeptides of SEQ ID NO: 9, 10, 11, 12, 13, 14, 15, 16, 17, 18, 19, 20, 21 or 22 and nucleic acid sequences of SEQ ID NO: 31, 32, 33, 34, 35, 36, 37, 38, 39, 40, 41, 42, 43 or 44) and flanked by appropriately designed overlaps introduced by PCR were gel-extracted and suspended in $dH_2O$ at a concentration of 1 ng/µl. One microliter of each of these DNA solutions was added (i.e. 3 µl in total) as DNA template to a PCR reaction, and a standard PCR procedure was carried out.

For the assembly of the combinatorial library the same strategy was used, but all the 17 different genes were pooled together simultaneously in a single 1.5 ml Eppendorf tube, for a total DNA concentration of approx. 30 ng/µl (about 1.8 ng/µl each gene). One microliter of this solution was used as template DNA in a standard PCR reaction, and gel extraction was performed to isolate amplicons of fragment size of between 2.5 and 3.5 kb approximately. Gel-extracted DNA was digested with AscI and SpeI and cloned.

The activity of the assembled l-MVA pathway variants was assessed by a functional assay providing indirect information about *E. coli* cellular synthesis of isopentenyl pyrophosphate (IPP) and dimethylallyl pyrophosphate (DMAPP), two essential metabolites used as terpenoids building blocks and synthesized as the last products of the l-MVA pathway (or the MEP pathway).

The antibiotic fosmidomycin (inhibitor of DOXP reductase (dxr), the second enzyme of the MEP pathway) was selected to inhibit the native *E. coli* MEP pathway that supplies the essential metabolites IPP and DMAPP. NEB5α competent cells were transformed with pBDISC0768-derivatives expressing the different l-MVA pathway variants, and then plated on LBA supplemented with tetracycline (10 µg/ml), fosmidomycin (5 µg/ml), and 1 mM (R)-mevalonic acid or (R)-Mevalonolactone. (R)-Mevalonolactone produced the same results as the corresponding acid form (R)-mevalonic acid (also in the isoprene detection assay described below), and it was selected as the substrate throughout both assays. As cells expressing a functional l-MVA pathway can grow in the presence of inhibitory concentrations of fosmidomycin only when an appropriate concentration of (R)-mevalonate is also provided, this type of medium was specifically selective for functional l-MVA pathway variants from a library.

Isoprene production in the l-MVA pathway variants was also assessed. Specifically, pre-cultures of all *C. necator* strains tested were prepared in 20 ml TSB-D supplemented with appropriate antibiotics (tetracycline 10 ng/µl, kanamycin 200 ng/µl). After 48 hours of growth at 30° C., these pre-cultures were used to inoculate (2% v/v) 10 ml of the same medium and grown ON at 30° C. at 230 rpm in a shaking incubator (induction with 1% (w/v) arabinose after 6-8 hours of growth).

The next day cultures were centrifuged and the pellet was re-suspended in new TSB-D plus antibiotic/inducer at a concentration of 0.1 g wcw/ml (wet cell weight/ml).

Gas chromatography vials (screw cap headspace gas chromatography (GC) vials (Anatune 093640-040-00 and 093640-038-00)) were prepared that contained with 1.96 ml of TSB-D supplemented with appropriate antibiotics as above, arabinose 1%, and 15 mM (R)-mevalonolactone, and inoculated with 40 µl of the respective ON cell culture. All samples and 5 additional positive controls (containing standard concentration of isoprene) were prepared in triplicate and incubate 24h at 30° C. (160 rpm), before being analysed by gas chromatography-mass spectrometry using an Agilent GCMS 7890B-5977A with a Gerstel MPS Autosampler, set with the parameters reported in the following two tables Table A and Table B.

TABLE A

| GCMS CONDITIONS | | |
|---|---|---|
| PARAMETER | VALUE | |
| Carrier Gas | Helium at constant flow (2.0 ml/min) | |
| Injector | Split ratio | Split 200:1 |
| | Temperature | 150° C. |
| Detector | Source Temperature | 230° C. |
| | Quad Temperature | 150° C. |
| | Interface | 260° C. |
| | Gain | 1 |
| | Scan Range | m/z 28-200 |
| | Threshold | 150 |
| | Scan Speed | 4 |

TABLE A-continued

| GCMS CONDITIONS | |
|---|---|
| PARAMETER | VALUE |
| | 2^2 (A/D samples) |
| | Sampling Rate |
| | 2^n = 2^2 |
| | Mode SCAN and SIM |
| Solvent delay * | 5.50 min |
| Oven Temperature | Initial T: 40° C. × 7.5 min |
| Oven Ramp | 120° C./min to 260° C. for 5 min |
| Injection volume | 300 µl from the HS in the GC 2 ml vial |
| Incubation time and T | 15 min at 95° C. |
| Agitator | ON 500 rpm |
| Injection volume | 300 µl of the Head Space |
| Gas saver | On after 2 min |
| Concentration range (µg/ml) | 25-250 PPM |
| GC Column | DB-624 122-1334 Agilent) |
| | 60 m × 250 µm × 1.4 µm |

TABLE B

| Compound | Ions monitored in SIM Mode (m/z) |
|---|---|
| Isoprene | 39, 53, 67 |

Ions used for the Isoprene quantitation in selected ion monitoring (SIM) acquisition mode

Example 8: Preparation of u-MVA Variants

The selection of genes used to prepare u-MVA is provided in Table 5.

TABLE 5

Genes used to perform the uMVA screen, with SEQ ID NO, organism of origin, gene function and GenBank/Uniprot identifier provided.

| SEQ ID NO (nucleotide) | SEQ ID NO (amino acid) | Organism | Gene | GenBank/UniProt |
|---|---|---|---|---|
| 55 | 56 | *C. necator* | Acetoacetyl-CoA C-acetyltransferase | CAJ92573 |
| 67 | 68 | *Saccharomyces cerevisiae* | Hydroxymethylglutaryl-CoA synthase | NP_013580 |
| 69 | 70 | *Listeria monocytogenes* | hydroxymethylglutaryl-CoA synthase | WP_003732325 |
| 71 | 72 | *Lactococcus lactis* | Hydroxymethylglutaryl-CoA synthase | WP_010906037 |
| 57 | 58 | *Saccharomyces cerevisiae* | Hydroxymethylglutaryl-CoA reductase (Residues 554-1054) | AJS96703 |
| 59 | 60 | *Listeria monocytogenes* | Hydroxymethylglutaryl-CoA reductase | WP_003721392 |
| 61 | 62 | *Streptococcus pneumoniae* | Hydroxymethylglutaryl-CoA reductase | WP_000704390 |
| 63 | 64 | *Lactococcus lactis* | Hydroxymethylglutaryl-CoA reductase | WP_010906035 |
| 65 | 66 | *Staphylococcus aureus* | Hydroxymethylglutaryl-CoA reductase | WP_072512079.1 |
| 73 | 2 | *Enterococcus faecalis* | mvaS mutant, Hydroxymethylglutaryl-CoA synthase, with A110G mutation | 2HDB_A |
| 23 | 1 | *Enterococcus faecalis* | mvaE (bifunctional enzyme with acetoacetyl-CoA C-acetylransferase and hydroxymethylglutaryl-CoA | WP_002382276 |

uMVA Pathway Library Cloning Strategy

The uMVA pathway library was constructed by assembling a set of synthetic operons, under the control of the arabinose-inducible $P_{BAD}$ promoter, with the following order of DNA parts: $P_{BAD}$ promoter-ISPS-PhaA-HMGR-HMGS-rrrnBT2 terminator. (ISPS=isoprene synthase; PhaA=acetoacetyl-CoA C-acetyltransferase; HMGR=hydroxymethylglutaryl-CoA reductase and HMGS=hydroxymethylglutaryl-CoA synthase).

Individual genes were amplified by PCR and cloned using standard molecular biology techniques. The different operons assembled are listed in Table 6. The constructs were transformed into chemically competent *E. coli* cells and correct clones were verified by colony PCR. Plasmids were recovered, and the presence of the insert was confirmed by sequencing. The correct constructs were transformed in *C. necator* and new strains were assessed by their ability to generate isoprene.

TABLE 6

Description of uMVA constructs generated.

| uMVA variant | Description |
|---|---|
| uMVA_01 | pBBR1-1A-pBAD-*Salix* ISPS-*C. necator*_phaA-*S. cerevisiae* HMGR -*S. cerevisiae* HMGS-rrnBt2 |
| uMVA_02 | pBBR1-1A-pBAD- *Salix* ISPS -*C. necator*_phaA-*S. cerevisiae* HMGR -*L. monocytogenes* HMGS-rrnBt2 |
| uMVA_03 | pBBR1-1A-pBAD- *Salix* ISPS -*C. necator*_phaA-*S. cerevisiae* HMGR -*L. lactis* HMGS-rrnBt2 |
| uMVA_04 | pBBR1-1A-pBAD- *Salix* ISPS -*C. necator*_phaA-*S. cerevisiae* HMGR -*E. faecalis* mvaS mutant-rrnBt2 |
| uMVA_05 | pBBR1-1A-pBAD- *Salix* ISPS -*C. necator*_phaA- *L. monocytogenes* HMGR - *S. cerevisiae* HMGS -rrnBt2 |
| uMVA_06 | pBBR1-1A-pBAD- *Salix* ISPS -*C. necator*_phaA- *L. monocytogenes* HMGR - *L. monocytogenes* HMGS -rrnBt2 |
| uMVA_07 | pBBR1-1A-pBAD- *Salix* ISPS -*C. necator*_phaA- *L. monocytogenes* HMGR - *L. lactis* HMGS -rrnBt2 |
| uMVA_08 | pBBR1-1A-pBAD- *Salix* ISPS -*C. necator* phaA- *L. monocytogenes* HMGR - *E. faecalis* mvaS mutant rrnBt2 |
| uMVA_13 | pBBR1-1A-pBAD- *Salix* ISPS -*C. necator*_phaA- *S. pneumoniae* HMGR- *S. cerevisiae* HMGS -rrnBt2 |
| uMVA_14 | pBBR1-1A-pBAD- *Salix* ISPS -*C. necator*_phaA- *S. pneumoniae* HMGR - *L. monocytogenes* HMGS -rrnBt2 |
| uMVA_15 | pBBR1-1A-pBAD- *Salix* ISPS -*C. necator*_phaA- *S. pneumoniae* HMGR - *L. lactis* HMGS -rrnBt2 |
| uMVA_16 | pBBR1-1A-pBAD- *Salix* ISPS -*C. necator*_phaA- *S. pneumoniae* HMGR - *E. faecalis* mvaS mutant-rrnBt2 |
| uMVA_17 | pBBR1-1A-pBAD- *Salix* ISPS -*C. necator*_phaA-*L. lactis* HMGR - *S. cerevisiae* HMGS -rrnBt2 |
| uMVA_18 | pBBR1-1A-pBAD- *Salix* ISPS -*C. necator*_phaA-*L. lactis* HMGR - *L. monocytogenes* HMGS -rrnBt2 |
| uMVA_19 | pBBR1-1A-pBAD- *Salix* ISPS -*C. necator*_phaA-*L. lactis* HMGR - *L. lactis* HMGS -rrnBt2 |
| uMVA_20 | pBBR1-1A-pBAD- *Salix* ISPS -*C. necator*_phaA-*L. lactis* HMGR - *E. faecalis* mvaS mutant-rrnBt2 |
| uMVA_21 | pBBR1-1A-pBAD- *Salix* ISPS -*C. necator*_phaA-*S. aureus* HMGR- *S. cerevisiae* HMGS -rrnBt2 |
| uMVA_22 | pBBR1-1A-pBAD- *Salix* ISPS -*C. necator*_phaA-*S. aureus* HMGR - *L. monocytogenes* HMGS -rrnBt2 |
| uMVA_23 | pBBR1-1A-pBAD- *Salix* ISPS -*C. necator*_phaA-*S. aureus* HMGR - *L. lactis* HMGS -rrnBt2 |
| uMVA_24 | pBBR1-1A-pBAD- *Salix* ISPS -*C. necator*_phaA-*S. aureus* HMGR - *E. faecalis* mvaS mutant-rrnBt2 |
| uMVA_25 | pBBR1-1A-pBAD- *Salix* ISPS - *E. faecalis* mvaE-*E. faecalis* mvaS -rrBt2 |

Isoprene Assay

To assess isoprene production in a *C. necator* strain with the whole MVA pathway and an isoprene synthase, uMVA-pathway variants were expressed in a *C. necator* H16 derivative strain. This strain possesses the ΔphaC1AB1 and ΔH16_A0006-9 genotypes conferring a PHA-phenotype and improved transformation efficiency, respectively. This strain also has an ispS (encoding the isoprene synthase of *P. alba*) and the *E. faecalis* uMVA construct integrated into chromosome 1 at the phaC1AB1 locus. It also has the *S. pneumonia* 1MVA-idi construct integrated into chromosome 1 at the phaB2C2 locus. Expression of the plasmid-based uMVA-pathway variants in this genetic background supplemented the activity conferred by the integrated *E. faecalis* uMVA construct. Therefore, it was possible to assess the impact (if any) of the different uMVA pathways on isoprene production.

*C. necator* library strains were evaluated for de novo isoprene synthesis in bioassays based on gas chromatography-mass spectrometry (GC-MS). Seeding cultures were prepared for each strain by inoculating a single colony into 20 ml of 27.5 g/L Tryptone Soya Broth without Dextrose containing the appropriate antibiotic when necessary. Unless otherwise stated, the seeding cultures were incubated at 30° C., 230 rpm for 48 hours, then diluted by 1 in 50 into fresh TSB-D media (10 ml) in 50 ml sterile Falcon tubes and incubated for approximately 6-7 hours at 30° C., 230 rpm. MVA pathway and isoprene synthase expression was induced by adding arabinose to a final concentration of 0.4-1% w/v and the cultures were incubated for a further 16 hours (overnight) at 30° C., 230 rpm. The cultures were pelleted by centrifugation at 6000 g for 20 minutes and the density of each culture was normalized to either a standard optical density ($OD_{600}$) or wet cell weight (WCW) concentration (gWCW/ml) by re-suspending the *C. necator* cells with the appropriate volume of either minimal media or TSB media. For each experimental variable (strain and media conditions), separate isoprene bioassays were set up in triplicate in 10 ml GC-MS vials containing 2 ml fresh minimal or TSB media (with 1% w/v arabinose and appropriate antibiotics) and 40 µl-60 µl of each cell suspension.

An isoprene calibration series was set up in 10 ml GC-MS vials containing 1990 µl minimal/TSB media with 10 µl of 20 ppm to 1000 ppm of isoprene standards dissolved in 0.5% v/v methanol at 4° C. To test isoprene assay robustness and precision, spike-recovery vials were also set up containing 10 µl of 1 ppm isoprene, for a random selection of the experimental conditions tested. All vials (isoprene experimental, isoprene standard and spike recovery vials) were incubated at 30° C., 160 rpm, for 24 hours.

Measurement of Headspace Isoprene Concentrations

Headspace isoprene measurements were performed by GC-MS on an Agilent Technologies 7890B gas chromatograph connected to an Agilent quadrupole 5977A MSD instrument with an electronically controlled split/split-less injection port. The instrument was equipped with a dual head MPS autosampler (Gerstel) for head Space analysis. GC separation was performed on a db-624 capillary column (60 m×0.25 mm×1.4 µm J&W Scientific). The GC-MS parameters were as described in Table 7. The M-1 ion was used for isoprene quantification.

TABLE 7

Typical GCMS parameters for the measurement of head space isoprene concentrations.

GCMS CONDITIONS

| PARAMETER | VALUE | |
|---|---|---|
| Carrier Gas | Helium at constant flow (2.0 ml/min) | |
| Injector | Split ratio | Split 10:L |
| | Temperature | 150° C. |
| Detector | Source Temperature | 230° C. |
| | Quad Temperature | 150° C. |

TABLE 7-continued

Typical GCMS parameters for the measurement of head space isoprene concentrations.
GCMS CONDITIONS

| PARAMETER | VALUE | |
|---|---|---|
| | Interface | 260° C. |
| | Gain | 1 |
| | Scan Range | m/z 28-200 |
| | Threshold | 150 |
| | Scan Speed | 4 |
| | 2^2 (A/D samples) Sampling Rate 2^n = 2^2 | |
| | Mode | SCAN and SIM |
| Solvent delay * | 5.50 min | |
| Oven Temperature | Initial T: 40° C. × 6.9 min | |
| Oven Ramp | 120° C./min to 260° C. for 6 min | |
| Injection volume | 500 μl from the HS in the GC 2 ml vial | |
| Incubation time and T | 13 min at 95° C. | |

TABLE 7-continued

Typical GCMS parameters for the measurement of head space isoprene concentrations.
GCMS CONDITIONS

| PARAMETER | VALUE |
|---|---|
| Agitator | ON 500 rpm |
| Injection volume | 500 μl of the Head Space |
| Gas saver | On after 2 min |
| Concentration range (μg/ml) | 0.1-5.0 |
| GC Column | DB-624 122-1334 Agilent (60 m × 250 μm × 1.4 μm) |

A total of 11 strains yielded more isoprene than the benchmark strain (harbouring a plasmid expressing the *Salix* ISPS) with uMVA_22 and uMVA_21 variants producing highest isoprene titers. Nine variants are shown in Table 8 which show isoprene accumulation of more than 200 ppm.

TABLE 8

Isoprene accumulation in BDISC0921 in parts per million (ppm) and peak area (response*). Values represent average of 3 technical replicas (AV) and respective standard deviation (SD). Strains are ranked according to response. BM, Benchmark strain is BDISC1079; ISPS is a negative control. Calibration curve: 10-100 ppm (linearity confirmed until 200 ppm).

| Sample # | Plasmids | ISPS | Thiolase (phaA) | HMG-Reductase | HMG-Synthase | Isoprene [ppm] Av | Isoprene [ppm] SD | Response Av | Response SD |
|---|---|---|---|---|---|---|---|---|---|
| uMVA_22 | pBBR1-1A-pBAD-ISPS-phaA-HMGR-HMGS | *Salix* | *C. necator* | *S. aureaus* | *L. monocytogenes* | >200 | N/A | 10688202 | 364067 |
| uMVA_21 | pBBR1-1A-pBAD- ISPS-phaA-HMGR-HMGS | *Salix* | *C. necator* | *S. aureaus* | *S. cerevisiae* | >200 | N/A | 7871810 | 1245912 |
| uMVA_02 | pBBR1-1A-pBAD- ISPS-phaA-HMGR-HMGS | *Salix* | *C. necator* | *S. cerevisiae* | *L. monocytogenes* | >200 | N/A | 7717383 | 249189 |
| uMVA_05 | pBBR1-1A-pBAD- ISPS-phaA-HMGR-HMGS | *Salix* | *C. necator* | *L. monocytogenes* | *S. cerevisiae* | >200 | N/A | 7419799 | 525728 |
| uMVA_06 | pBBR1-1A-pBAD- ISPS-phaA-HMGR-HMGS | *Salix* | *C. necator* | *L. monocytogenes* | *L. monocytogenes* | >200 | N/A | 7415379 | 1659318 |
| uMVA_03 | pBBR1-1A-pBAD- ISPS-phaA-HMGR-HMGS | *Salix* | *C. necator* | *S. cerevisiae* | *L. lactis* | >200 | N/A | 7118750 | 713724 |
| uMVA_01 | pBBR1-1A-pBAD- ISPS-phaA-HMGR-HMGS | *Salix* | *C. necator* | *S. cerevisiae* | *S. cerevisiae* | >200 | N/A | 6415893 | 871819 |
| uMVA_13 | pBBR1-1A-pBAD- ISPS-phaA-HMGR-HMGS | *Salix* | *C. necator* | *S. pneumoniae* | *S. cerevisiae* | >200 | N/A | 5323252 | 705510 |
| uMVA_14 | pBBR1-1A-pBAD- ISPS-phaA-HMGR-HMGS | *Salix* | *C. necator* | *S. pneumoniae* | *L. monocytogenes* | >200 | N/A | 3522866 | 426528 |
| BM | pBBR1-1A-pBAD- ISPS-HMGS | *Salix* | — | — | *S. cerevisiae* | 105.342 | 55.417 | 1712451 | 900867 |
| ISPS | pBBR1-1A-pBAD-407 | *Salix* | — | — | — | 1.735 | 0.674 | 28212 | 10956 |

What is claimed is:

1. A genetically engineered *Cupriavidus* host capable of producing hydrocarbons comprising one or more isoprene units, said genetically engineered *Cupriavidus* host comprising a genome-integrated synthetic operon comprising an exogenous nucleic acid sequence encoding a polypeptide having acetoacetyl-CoA C-acetyltransferase (AACT), an exogenous nucleic acid sequence encoding HMG-CoA reductase (HMGR) or hydroxymethylglutaryl-CoA synthase (HMGS) enzyme activity and an exogenous nucleic acid sequence encoding an isoprene synthase (IspS) enzyme wherein the polypeptide having AACT enzyme activity that catalyzes the chemical reaction of 2 acetyl-CoA to CoA and acetoacetyl-CoA and has at least 90% sequence identity to SEQ ID NO:56 or is encoded by a nucleic acid sequence with at least 90% sequence identity to SEQ ID NO: 55, the polypeptide having HMGR enzyme activity that catalyzes the reaction of HMG-CoA (3-hydroxy-3-methylglutaryl-CoA) to mevalonic acid and has at least 90% sequence identity to SEQ ID NO:58, 60, 62, 64 or 66 or is encoded by a nucleic acid sequence with at least 90% sequence identity to SEQ ID NO:57, 59, 61, 63 or 65 or the polypeptide having HMGS enzyme activity that catalyzes the reaction of acetoacetyl-CoA to HMG-CoA and has at least 90% sequence identity to SEQ ID NO: 68, 70, 72 or 74 or is encoded by a nucleic acid sequence with at least 90% sequence identity to SEQ ID NO: 67, 69, 71 or 73, and wherein the IspS enzyme has at least 90% sequence identity to an amino acid sequence set forth in SEQ ID NOs: 7, 8, 29 or 30 and catalyzes the reaction dimethylallyl pyrophosphate to isoprene and diphosphate, wherein said genetically engineered *Cupriavidus* host produces the hydrocarbon comprising one or more isoprene units from a gas stream comprising at least one of natural gas, methanol, ethanol, non-volatile residue, caustic wash from cyclohexane oxidation processes, or waste stream, or derivative thereof, in an amount at least 60 times greater than a *Cupriavidus* host cell harbouring a plasmid expressing only IspS.

2. The genetically engineered host of claim 1, wherein said hydrocarbon comprises said one or more isoprene units as depicted in Formula I (I)

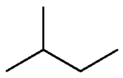

or a salt or derivative thereof.

3. The genetically engineered host of claim 1 further comprising one or more enzymes selected from mevalonate kinase (MVK), phosphomevalonate kinase (MPK), mevalonate diphosphate decarboxylase (MDD) and isopentenyl diphosphate isomerase (IDI).

4. The genetically engineered host of claim 1 wherein the genome-integrated synthetic operon encodes one or more *Enterococcus faecalis* enzymes.

5. The genetically engineered host of claim 1 further comprising one or more plasmids encoding one or more enzymes of the lower and/or upper MVA pathways.

6. The genetically engineered host of claim 1 wherein the genome integrated synthetic operon comprises an exogenous nucleic acid sequence encoding a polypeptide having AACT enzyme activity, an exogenous nucleic acid sequence encoding a polypeptide having HMGR enzyme activity, an exogenous nucleic acid sequence encoding a polypeptide having HMGS enzyme activity and an exogenous nucleic acid sequence encoding a polypeptide having IspS enzyme activity.

* * * * *

SEQUENCE LISTING

<160> NUMBER OF SEQ ID NOS: 74

<210> SEQ ID NO 1
<211> LENGTH: 803
<212> TYPE: PRT
<213> ORGANISM: Enterococcus faecalis

<400> SEQUENCE: 1

Met Lys Thr Val Val Ile Ile Asp Ala Leu Arg Thr Pro Ile Gly Lys
1 5 10 15

Tyr Lys Gly Ser Leu Ser Gln Val Ser Ala Val Asp Leu Gly Thr His
20 25 30

Val Thr Thr Gln Leu Leu Lys Arg His Ser Thr Ile Ser Glu Glu Ile
35 40 45

Asp Gln Val Ile Phe Gly Asn Val Leu Gln Ala Gly Asn Gly Gln Asn
50 55 60

Pro Ala Arg Gln Ile Ala Ile Asn Ser Gly Leu Ser His Glu Ile Pro
65 70 75 80

Ala Met Thr Val Asn Glu Val Cys Gly Ser Gly Met Lys Ala Val Ile
85 90 95

Leu Ala Lys Gln Leu Ile Gln Leu Gly Glu Ala Glu Val Leu Ile Ala
100 105 110

Gly Gly Ile Glu Asn Met Ser Gln Ala Pro Lys Leu Gln Arg Phe Asn
115 120 125

Tyr Glu Thr Glu Ser Tyr Asp Ala Pro Phe Ser Ser Met Met Tyr Asp
130 135 140

Gly Leu Thr Asp Ala Phe Ser Gly Gln Ala Met Gly Leu Thr Ala Glu
145 150 155 160

Asn Val Ala Glu Lys Tyr His Val Thr Arg Glu Glu Gln Asp Gln Phe
165 170 175

Ser Val His Ser Gln Leu Lys Ala Ala Gln Ala Gln Ala Glu Gly Ile
180 185 190

Phe Ala Asp Glu Ile Ala Pro Leu Glu Val Ser Gly Thr Leu Val Glu
195 200 205

Lys Asp Glu Gly Ile Arg Pro Asn Ser Ser Val Glu Lys Leu Gly Thr
210 215 220

Leu Lys Thr Val Phe Lys Glu Asp Gly Thr Val Thr Ala Gly Asn Ala
225 230 235 240

Ser Thr Ile Asn Asp Gly Ala Ser Ala Leu Ile Ile Ala Ser Gln Glu
245 250 255

Tyr Ala Glu Ala His Gly Leu Pro Tyr Leu Ala Ile Ile Arg Asp Ser
260 265 270

Val Glu Val Gly Ile Asp Pro Ala Tyr Met Gly Ile Ser Pro Ile Lys
275 280 285

Ala Ile Gln Lys Leu Leu Ala Arg Asn Gln Leu Thr Thr Glu Glu Ile
290 295 300

Asp Leu Tyr Glu Ile Asn Glu Ala Phe Ala Ala Thr Ser Ile Val Val
305 310 315 320

Gln Arg Glu Leu Ala Leu Pro Glu Glu Lys Val Asn Ile Tyr Gly Gly
325 330 335

Gly Ile Ser Leu Gly His Ala Ile Gly Ala Thr Gly Ala Arg Leu Leu
340 345 350

Thr Ser Leu Ser Tyr Gln Leu Asn Gln Lys Glu Lys Lys Tyr Gly Val
355 360 365

-continued

```
Ala Ser Leu Cys Ile Gly Gly Gly Leu Gly Leu Ala Met Leu Leu Glu
    370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
                405                 410                 415

Lys Lys Glu Phe Glu Asn Thr Ala Leu Ser Ser Gln Ile Ala Asn His
            420                 425                 430

Met Ile Glu Asn Gln Ile Ser Glu Thr Glu Val Pro Met Gly Val Gly
        435                 440                 445

Leu His Leu Thr Val Asp Glu Thr Asp Tyr Leu Val Pro Met Ala Thr
    450                 455                 460

Glu Glu Pro Ser Val Ile Ala Ala Leu Ser Asn Gly Ala Lys Ile Ala
465                 470                 475                 480

Gln Gly Phe Lys Thr Val Asn Gln Gln Arg Leu Met Arg Gly Gln Ile
                485                 490                 495

Val Phe Tyr Asp Val Ala Asp Pro Glu Ser Leu Ile Asp Lys Leu Gln
            500                 505                 510

Val Arg Glu Ala Glu Val Phe Gln Gln Ala Glu Leu Ser Tyr Pro Ser
        515                 520                 525

Ile Val Lys Arg Gly Gly Gly Leu Arg Asp Leu Gln Tyr Arg Thr Phe
    530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
                565                 570                 575

Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
        595                 600                 605

Ser Arg Leu Ser Lys Gly Ser Asn Gly Arg Glu Ile Ala Glu Lys Ile
    610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
        675                 680                 685

Gln Leu Ile Gly Glu Ile Ser Val Pro Leu Ala Leu Ala Thr Val Gly
    690                 695                 700

Gly Ala Thr Lys Val Leu Pro Lys Ser Gln Ala Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
        755                 760                 765

Gly Ala Thr Gly Lys Glu Val Glu Ala Val Ala Gln Gln Leu Lys Arg
    770                 775                 780

Gln Lys Thr Met Asn Gln Asp Arg Ala Met Ala Ile Leu Asn Asp Leu
```

-continued 785 790 795 800

Arg Lys Gln

<210> SEQ ID NO 2
<211> LENGTH: 383
<212> TYPE: PRT
<213> ORGANISM: Enterococcus faecalis

<400> SEQUENCE: 2

Met Thr Ile Gly Ile Asp Lys Ile Ser Phe Phe Val Pro Pro Tyr Tyr
1 5 10 15

Ile Asp Met Thr Ala Leu Ala Glu Ala Arg Asn Val Asp Pro Gly Lys
20 25 30

Phe His Ile Gly Ile Gly Gln Asp Gln Met Ala Val Asn Pro Ile Ser
35 40 45

Gln Asp Ile Val Thr Phe Ala Ala Asn Ala Ala Glu Ala Ile Leu Thr
50 55 60

Lys Glu Asp Lys Glu Ala Ile Asp Met Val Ile Val Gly Thr Glu Ser
65 70 75 80

Ser Ile Asp Glu Ser Lys Ala Ala Ala Val Val Leu His Arg Leu Met
85 90 95

Gly Ile Gln Pro Phe Ala Arg Ser Phe Glu Ile Lys Glu Ala Cys Tyr
100 105 110

Gly Ala Thr Ala Gly Leu Gln Leu Ala Lys Asn His Val Ala Leu His
115 120 125

Pro Asp Lys Lys Val Leu Val Val Ala Ala Asp Ile Ala Lys Tyr Gly
130 135 140

Leu Asn Ser Gly Gly Glu Pro Thr Gln Gly Ala Gly Ala Val Ala Met
145 150 155 160

Leu Val Ala Ser Glu Pro Arg Ile Leu Ala Leu Lys Glu Asp Asn Val
165 170 175

Met Leu Thr Gln Asp Ile Tyr Asp Phe Trp Arg Pro Thr Gly His Pro
180 185 190

Tyr Pro Met Val Asp Gly Pro Leu Ser Asn Glu Thr Tyr Ile Gln Ser
195 200 205

Phe Ala Gln Val Trp Asp Glu His Lys Lys Arg Thr Gly Leu Asp Phe
210 215 220

Ala Asp Tyr Asp Ala Leu Ala Phe His Ile Pro Tyr Thr Lys Met Gly
225 230 235 240

Lys Lys Ala Leu Leu Ala Lys Ile Ser Asp Gln Thr Glu Ala Glu Gln
245 250 255

Glu Arg Ile Leu Ala Arg Tyr Glu Glu Ser Ile Val Tyr Ser Arg Arg
260 265 270

Val Gly Asn Leu Tyr Thr Gly Ser Leu Tyr Leu Gly Leu Ile Ser Leu
275 280 285

Leu Glu Asn Ala Thr Thr Leu Thr Ala Gly Asn Gln Ile Gly Leu Phe
290 295 300

Ser Tyr Gly Ser Gly Ala Val Ala Glu Phe Phe Thr Gly Glu Leu Val
305 310 315 320

Ala Gly Tyr Gln Asn His Leu Gln Lys Glu Thr His Leu Ala Leu Leu
325 330 335

Asp Asn Arg Thr Glu Leu Ser Ile Ala Glu Tyr Glu Ala Met Phe Ala
340 345 350

Glu Thr Leu Asp Thr Asp Ile Asp Gln Thr Leu Glu Asp Glu Leu Lys

```
        355                 360                 365

Tyr Ser Ile Ser Ala Ile Asn Asn Thr Val Arg Ser Tyr Arg Asn
    370                 375                 380


<210> SEQ ID NO 3
<211> LENGTH: 292
<212> TYPE: PRT
<213> ORGANISM: Streptococcus pneumoniae

<400> SEQUENCE: 3

Met Thr Lys Lys Val Gly Val Gly Gln Ala His Ser Lys Ile Ile Leu
1               5                   10                  15

Ile Gly Glu His Ala Val Val Tyr Gly Tyr Pro Ala Ile Ser Leu Pro
            20                  25                  30

Leu Leu Glu Val Glu Val Thr Cys Lys Val Val Pro Ala Glu Ser Pro
        35                  40                  45

Trp Arg Leu Tyr Glu Glu Asp Thr Leu Ser Met Ala Val Tyr Ala Ser
    50                  55                  60

Leu Glu Tyr Leu Asn Ile Thr Glu Ala Cys Ile Arg Cys Glu Ile Asp
65                  70                  75                  80

Ser Ala Ile Pro Glu Lys Arg Gly Met Gly Ser Ser Ala Ala Ile Ser
                85                  90                  95

Ile Ala Ala Ile Arg Ala Val Phe Asp Tyr Tyr Gln Ala Asp Leu Pro
            100                 105                 110

His Asp Val Leu Glu Ile Leu Val Asn Arg Ala Glu Met Ile Ala His
        115                 120                 125

Met Asn Pro Ser Gly Leu Asp Ala Lys Thr Cys Leu Ser Asp Gln Pro
    130                 135                 140

Ile Arg Phe Ile Lys Asn Val Gly Phe Thr Glu Leu Glu Met Asp Leu
145                 150                 155                 160

Ser Ala Tyr Leu Val Ile Ala Asp Thr Gly Val Tyr Gly His Thr Arg
                165                 170                 175

Glu Ala Ile Gln Val Val Gln Asn Lys Gly Lys Asp Ala Leu Pro Phe
            180                 185                 190

Leu His Ala Leu Gly Glu Leu Thr Gln Gln Ala Glu Val Ala Ile Ser
        195                 200                 205

Gln Lys Asp Ala Glu Gly Leu Gly Gln Ile Leu Ser Gln Ala His Leu
    210                 215                 220

His Leu Lys Glu Ile Gly Val Ser Ser Pro Glu Ala Asp Phe Leu Val
225                 230                 235                 240

Glu Thr Thr Leu Ser His Gly Ala Leu Gly Ala Lys Met Ser Gly Gly
                245                 250                 255

Gly Leu Gly Gly Cys Ile Ile Ala Leu Val Thr Asn Leu Thr His Ala
            260                 265                 270

Gln Glu Leu Ala Glu Arg Leu Glu Glu Lys Gly Ala Val Gln Thr Trp
        275                 280                 285

Ile Glu Ser Leu
    290


<210> SEQ ID NO 4
<211> LENGTH: 335
<212> TYPE: PRT
<213> ORGANISM: Streptococcus pneumoniae

<400> SEQUENCE: 4

Met Ile Ala Val Lys Thr Cys Gly Lys Leu Tyr Trp Ala Gly Glu Tyr
```

-continued

```
1               5                   10                  15

Ala Ile Leu Glu Pro Gly Gln Leu Ala Leu Ile Lys Asp Ile Pro Ile
            20                  25                  30

Tyr Met Arg Ala Glu Ile Ala Phe Ser Asp Ser Tyr Arg Ile Tyr Ser
        35                  40                  45

Asp Met Phe Asp Phe Ala Val Asp Leu Arg Pro Asn Pro Asp Tyr Ser
    50                  55                  60

Leu Ile Gln Glu Thr Ile Ala Leu Met Gly Asp Phe Leu Ala Val Arg
65                  70                  75                  80

Gly Gln Asn Leu Arg Pro Phe Ser Leu Glu Ile Cys Gly Lys Met Glu
                85                  90                  95

Arg Glu Gly Lys Lys Phe Gly Leu Gly Ser Ser Gly Ser Val Val Val
            100                 105                 110

Leu Val Val Lys Ala Leu Leu Ala Leu Tyr Asp Val Ser Val Asp Gln
        115                 120                 125

Glu Leu Leu Phe Lys Leu Thr Ser Ala Val Leu Leu Lys Arg Gly Asp
    130                 135                 140

Asn Gly Ser Met Gly Asp Leu Ala Cys Ile Val Ala Glu Asp Leu Val
145                 150                 155                 160

Leu Tyr Gln Ser Phe Asp Arg Gln Lys Val Ala Ala Trp Leu Glu Glu
                165                 170                 175

Glu Asn Leu Ala Thr Val Leu Glu Arg Asp Trp Gly Phe Ser Ile Ser
            180                 185                 190

Gln Val Lys Pro Thr Leu Glu Cys Asp Phe Leu Val Gly Trp Thr Lys
        195                 200                 205

Glu Val Ala Val Ser Ser His Met Val Gln Gln Ile Lys Gln Asn Ile
    210                 215                 220

Asn Gln Asn Phe Leu Thr Ser Ser Lys Glu Thr Val Thr Ser Leu Val
225                 230                 235                 240

Glu Ala Leu Glu Gln Gly Lys Ser Glu Lys Ile Ile Asp Gln Val Glu
                245                 250                 255

Val Ala Ser Lys Leu Leu Glu Gly Leu Ser Thr Asp Ile Tyr Thr Pro
            260                 265                 270

Leu Leu Arg Gln Leu Lys Glu Ala Ser Gln Asp Leu Gln Thr Val Ala
        275                 280                 285

Lys Ser Ser Gly Ala Gly Gly Gly Asp Cys Gly Ile Ala Leu Ser Phe
    290                 295                 300

Asp Ala Gln Ser Thr Lys Thr Leu Lys Asn Arg Trp Ala Asp Leu Gly
305                 310                 315                 320

Ile Glu Leu Leu Tyr Gln Glu Arg Ile Gly His Asp Asp Lys Ser
                325                 330                 335
```

<210> SEQ ID NO 5
<211> LENGTH: 317
<212> TYPE: PRT
<213> ORGANISM: Streptococcus pneumoniae

<400> SEQUENCE: 5

```
Met Asp Arg Glu Pro Val Thr Val Arg Ser Tyr Ala Asn Ile Ala Ile
1               5                   10                  15

Ile Lys Tyr Trp Gly Lys Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45
```

-continued

```
Ser Pro Leu Pro Ala Asn Val Thr Ala Asp Glu Phe Tyr Ile Asn Gly
    50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly His Arg Tyr Arg Leu Ile
    290                 295                 300

Val Ser Lys Thr Lys Asp Leu Ser Gln Asp Asp Cys Cys
305                 310                 315
```

<210> SEQ ID NO 6
<211> LENGTH: 336
<212> TYPE: PRT
<213> ORGANISM: Streptococcus pneumoniae

<400> SEQUENCE: 6

```
Met Thr Thr Asn Arg Lys Asp Glu His Ile Leu Tyr Ala Leu Glu Gln
1               5                   10                  15

Lys Ser Ser Tyr Asn Ser Phe Asp Glu Val Glu Leu Ile His Ser Ser
            20                  25                  30

Leu Pro Leu Tyr Asn Leu Asp Glu Ile Asp Leu Ser Thr Glu Phe Ala
        35                  40                  45

Gly Arg Lys Trp Asp Phe Pro Phe Tyr Ile Asn Ala Met Thr Gly Gly
    50                  55                  60

Ser Asn Lys Gly Arg Glu Ile Asn Gln Lys Leu Ala Gln Val Ala Glu
65                  70                  75                  80

Ser Cys Gly Ile Leu Phe Val Thr Gly Ser Tyr Ser Ala Ala Leu Lys
                85                  90                  95

Asn Pro Thr Asp Asp Ser Phe Ser Val Lys Ser Ser His Pro Asn Leu
            100                 105                 110
```

Leu Leu Gly Thr Asn Ile Gly Leu Asp Lys Pro Val Glu Leu Gly Leu
115 120 125

Gln Thr Val Glu Glu Met Asn Pro Val Leu Leu Gln Val His Val Asn
130 135 140

Val Met Gln Glu Leu Leu Met Pro Glu Gly Glu Arg Lys Phe Arg Ser
145 150 155 160

Trp Gln Ser His Leu Ala Asp Tyr Ser Lys Gln Ile Pro Val Pro Ile
165 170 175

Val Leu Lys Glu Val Gly Phe Gly Met Asp Ala Lys Thr Ile Glu Arg
180 185 190

Ala Tyr Glu Phe Gly Val Arg Thr Val Asp Leu Ser Gly Arg Gly Gly
195 200 205

Thr Ser Phe Ala Tyr Ile Glu Asn Arg Arg Ser Gly Gln Arg Asp Tyr
210 215 220

Leu Asn Gln Trp Gly Gln Ser Thr Met Gln Ala Leu Leu Asn Ala Gln
225 230 235 240

Glu Trp Lys Asp Lys Val Glu Leu Leu Val Ser Gly Gly Val Arg Asn
245 250 255

Pro Leu Asp Met Ile Lys Cys Leu Val Phe Gly Ala Lys Ala Val Gly
260 265 270

Leu Ser Arg Thr Val Leu Glu Leu Val Glu Thr Tyr Thr Val Glu Glu
275 280 285

Val Ile Gly Ile Val Gln Gly Trp Lys Ala Asp Leu Arg Leu Ile Met
290 295 300

Cys Ser Leu Asn Cys Ala Thr Ile Ala Asp Leu Gln Lys Val Asp Tyr
305 310 315 320

Leu Leu Tyr Gly Lys Leu Lys Glu Ala Lys Asp Gln Met Lys Lys Ala
325 330 335

<210> SEQ ID NO 7
<211> LENGTH: 559
<212> TYPE: PRT
<213> ORGANISM: Populus alba

<400> SEQUENCE: 7

Arg Cys Ser Val Ser Thr Glu Asn Val Ser Phe Thr Glu Thr Glu Thr
1 5 10 15

Glu Ala Arg Arg Ser Ala Asn Tyr Glu Pro Asn Ser Trp Asp Tyr Asp
20 25 30

Tyr Leu Leu Ser Ser Asp Thr Asp Glu Ser Ile Glu Val Tyr Lys Asp
35 40 45

Lys Ala Lys Lys Leu Glu Ala Glu Val Arg Arg Glu Ile Asn Asn Glu
50 55 60

Lys Ala Glu Phe Leu Thr Leu Leu Glu Leu Ile Asp Asn Val Gln Arg
65 70 75 80

Leu Gly Leu Gly Tyr Arg Phe Glu Ser Asp Ile Arg Gly Ala Leu Asp
85 90 95

Arg Phe Val Ser Ser Gly Gly Phe Asp Ala Val Thr Lys Thr Ser Leu
100 105 110

His Gly Thr Ala Leu Ser Phe Arg Leu Leu Arg Gln His Gly Phe Glu
115 120 125

Val Ser Gln Glu Ala Phe Ser Gly Phe Lys Asp Gln Asn Gly Asn Phe
130 135 140

Leu Glu Asn Leu Lys Glu Asp Ile Lys Ala Ile Leu Ser Leu Tyr Glu

```
145                 150                 155                 160

Ala Ser Phe Leu Ala Leu Glu Gly Glu Asn Ile Leu Asp Glu Ala Lys
                165                 170                 175

Val Phe Ala Ile Ser His Leu Lys Glu Leu Ser Glu Glu Lys Ile Gly
            180                 185                 190

Lys Glu Leu Ala Glu Gln Val Asn His Ala Leu Glu Leu Pro Leu His
        195                 200                 205

Arg Arg Thr Gln Arg Leu Glu Ala Val Trp Ser Ile Glu Ala Tyr Arg
    210                 215                 220

Lys Lys Glu Asp Ala Asn Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Arg
            260                 265                 270

Asp Arg Leu Ile Glu Ser Phe Tyr Trp Ala Val Gly Val Ala Phe Glu
        275                 280                 285

Pro Gln Tyr Ser Asp Cys Arg Asn Ser Val Ala Lys Met Phe Ser Phe
    290                 295                 300

Val Thr Ile Ile Asp Asp Ile Tyr Asp Val Tyr Gly Thr Leu Asp Glu
305                 310                 315                 320

Leu Glu Leu Phe Thr Asp Ala Val Glu Arg Trp Asp Val Asn Ala Ile
                325                 330                 335

Asn Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Asp Lys Gly Glu Asn
        355                 360                 365

Ile Leu Pro Tyr Leu Thr Lys Ala Trp Ala Asp Leu Cys Asn Ala Phe
    370                 375                 380

Leu Gln Glu Ala Lys Trp Leu Tyr Asn Lys Ser Thr Pro Thr Phe Asp
385                 390                 395                 400

Asp Tyr Phe Gly Asn Ala Trp Lys Ser Ser Ser Gly Pro Leu Gln Leu
                405                 410                 415

Val Phe Ala Tyr Phe Ala Val Val Gln Asn Ile Lys Lys Glu Glu Ile
            420                 425                 430

Glu Asn Leu Gln Lys Tyr His Asp Thr Ile Ser Arg Pro Ser His Ile
        435                 440                 445

Phe Arg Leu Cys Asn Asp Leu Ala Ser Ala Ser Ala Glu Ile Ala Arg
    450                 455                 460

Gly Glu Thr Ala Asn Ser Val Ser Cys Tyr Met Arg Thr Lys Gly Ile
465                 470                 475                 480

Ser Glu Glu Leu Ala Thr Glu Ser Val Met Asn Leu Ile Asp Glu Thr
                485                 490                 495

Trp Lys Lys Met Asn Lys Glu Lys Leu Gly Gly Ser Leu Phe Ala Lys
            500                 505                 510

Pro Phe Val Glu Thr Ala Ile Asn Leu Ala Arg Gln Ser His Cys Thr
        515                 520                 525

Tyr His Asn Gly Asp Ala His Thr Ser Pro Asp Glu Leu Thr Arg Lys
    530                 535                 540

Arg Val Leu Ser Val Ile Thr Glu Pro Ile Leu Pro Phe Glu Arg
545                 550                 555
```

<210> SEQ ID NO 8

<211> LENGTH: 559
<212> TYPE: PRT
<213> ORGANISM: Salix sp.

<400> SEQUENCE: 8

```
Arg Cys Ser Val Ser Thr Glu Asn Val Ser Phe Thr Glu Thr Glu Thr
1               5                   10                  15

Glu Thr Arg Arg Ser Ala Asn Tyr Glu Pro Asn Ser Trp Asp Tyr Asp
            20                  25                  30

Tyr Leu Leu Ser Ser Asp Thr Asp Glu Ser Ile Glu Val Tyr Lys Asp
        35                  40                  45

Lys Ala Lys Lys Leu Glu Ala Glu Val Arg Arg Glu Ile Asn Asn Glu
    50                  55                  60

Lys Ala Glu Phe Leu Thr Leu Leu Glu Leu Ile Asp Asn Val Gln Arg
65                  70                  75                  80

Leu Gly Leu Gly Tyr Arg Phe Glu Ser Asp Ile Arg Arg Ala Leu Asp
                85                  90                  95

Arg Phe Val Ser Ser Gly Gly Phe Asp Ala Val Thr Lys Thr Ser Leu
            100                 105                 110

His Ala Thr Ala Leu Ser Phe Arg Phe Leu Arg Gln His Gly Phe Glu
        115                 120                 125

Val Ser Gln Glu Ala Phe Gly Gly Phe Lys Asp Gln Asn Gly Asn Phe
    130                 135                 140

Leu Glu Asn Leu Lys Glu Asp Ile Lys Ala Ile Leu Ser Leu Tyr Glu
145                 150                 155                 160

Ala Ser Phe Leu Ala Leu Glu Gly Glu Asn Ile Leu Asp Glu Ala Lys
                165                 170                 175

Val Phe Ala Ile Ser His Leu Lys Glu Leu Ser Glu Glu Lys Ile Gly
            180                 185                 190

Lys Asp Leu Ala Glu Gln Val Asn His Ala Leu Glu Leu Pro Leu His
        195                 200                 205

Arg Arg Thr Gln Arg Leu Glu Ala Val Trp Ser Ile Glu Ala Tyr Arg
    210                 215                 220

Lys Lys Glu Asp Ala Asn Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Arg
            260                 265                 270

Asp Arg Leu Ile Glu Ser Phe Tyr Trp Ala Val Gly Val Ala Phe Glu
        275                 280                 285

Pro Gln Tyr Ser Asp Cys Arg Asn Ser Val Ala Lys Met Phe Ser Phe
    290                 295                 300

Val Thr Ile Ile Asp Asp Ile Tyr Asp Val Tyr Gly Thr Leu Asp Glu
305                 310                 315                 320

Leu Glu Leu Phe Thr Asp Ala Val Glu Arg Trp Asp Val Asn Ala Ile
                325                 330                 335

Asn Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Glu Lys Gly Glu Asn
        355                 360                 365

Ile Leu Pro Tyr Leu Thr Lys Ala Trp Ala Asp Leu Cys Asn Ala Phe
    370                 375                 380

Leu Gln Glu Ala Lys Trp Leu Tyr Asn Lys Ser Thr Pro Thr Phe Asp
```

-continued 385 390 395 400

Asp Tyr Phe Gly Asn Ala Trp Lys Ser Ser Ser Gly Pro Leu Gln Leu
405 410 415

Val Phe Ala Tyr Phe Ala Val Val Gln Asn Ile Lys Lys Glu Glu Ile
420 425 430

Glu Asn Leu Gln Lys Tyr His Asp Ile Ile Ser Arg Pro Ser His Ile
435 440 445

Phe Arg Leu Cys Asn Asp Leu Ala Ser Ala Ser Ala Glu Ile Ala Arg
450 455 460

Gly Glu Thr Ala Asn Ser Val Ser Cys Tyr Met Arg Thr Lys Gly Ile
465 470 475 480

Ser Glu Glu Leu Ala Thr Glu Ser Val Met Asn Leu Ile Asp Glu Thr
485 490 495

Trp Lys Lys Met Asn Lys Glu Lys Leu Gly Gly Ser Leu Phe Pro Lys
500 505 510

Pro Phe Val Glu Thr Ala Ile Asn Leu Ala Arg Gln Ser His Cys Thr
515 520 525

Tyr His Asn Gly Asp Ala His Thr Ser Pro Asp Glu Leu Thr Arg Lys
530 535 540

Arg Val Leu Ser Val Ile Thr Glu Pro Ile Leu Pro Phe Glu Arg
545 550 555

<210> SEQ ID NO 9
<211> LENGTH: 396
<212> TYPE: PRT
<213> ORGANISM: Homo sapien

<400> SEQUENCE: 9

Met Leu Ser Glu Val Leu Leu Val Ser Ala Pro Gly Lys Val Ile Leu
1 5 10 15

His Gly Glu His Ala Val Val His Gly Lys Val Ala Leu Ala Val Ser
20 25 30

Leu Asn Leu Arg Thr Phe Leu Arg Leu Gln Pro His Ser Asn Gly Lys
35 40 45

Val Asp Leu Ser Leu Pro Asn Ile Gly Ile Lys Arg Ala Trp Asp Val
50 55 60

Ala Arg Leu Gln Ser Leu Asp Thr Ser Phe Leu Glu Gln Gly Asp Val
65 70 75 80

Thr Thr Pro Thr Ser Glu Gln Val Glu Lys Leu Lys Glu Val Ala Gly
85 90 95

Leu Pro Asp Asp Cys Ala Val Thr Glu Arg Leu Ala Val Leu Ala Phe
100 105 110

Leu Tyr Leu Tyr Leu Ser Ile Cys Arg Lys Gln Arg Ala Leu Pro Ser
115 120 125

Leu Asp Ile Val Val Trp Ser Glu Leu Pro Pro Gly Ala Gly Leu Gly
130 135 140

Ser Ser Ala Ala Tyr Ser Val Cys Leu Ala Ala Ala Leu Leu Thr Val
145 150 155 160

Cys Glu Glu Ile Pro Asn Pro Leu Lys Asp Gly Asp Cys Val Asn Arg
165 170 175

Trp Thr Lys Glu Asp Leu Glu Leu Ile Asn Lys Trp Ala Phe Gln Gly
180 185 190

Glu Arg Met Ile His Gly Asn Pro Ser Gly Val Asp Asn Ala Val Ser
195 200 205

-continued

Thr Trp Gly Gly Ala Leu Arg Tyr His Gln Gly Lys Ile Ser Ser Leu
    210                 215                 220

Lys Arg Ser Pro Ala Leu Gln Ile Leu Leu Thr Asn Thr Lys Val Pro
225                 230                 235                 240

Arg Asn Thr Arg Ala Leu Val Ala Gly Val Arg Asn Arg Leu Leu Lys
                245                 250                 255

Phe Pro Glu Ile Val Ala Pro Leu Leu Thr Ser Ile Asp Ala Ile Ser
            260                 265                 270

Leu Glu Cys Glu Arg Val Leu Gly Glu Met Gly Glu Ala Pro Ala Pro
        275                 280                 285

Glu Gln Tyr Leu Val Leu Glu Glu Leu Ile Asp Met Asn Gln His His
    290                 295                 300

Leu Asn Ala Leu Gly Val Gly His Ala Ser Leu Asp Gln Leu Cys Gln
305                 310                 315                 320

Val Thr Arg Ala Arg Gly Leu His Ser Lys Leu Thr Gly Ala Gly Gly
                325                 330                 335

Gly Gly Cys Gly Ile Thr Leu Leu Lys Pro Gly Leu Glu Gln Pro Glu
            340                 345                 350

Val Glu Ala Thr Lys Gln Ala Leu Thr Ser Cys Gly Phe Asp Cys Leu
        355                 360                 365

Glu Thr Ser Ile Gly Ala Pro Gly Val Ser Ile His Ser Ala Thr Ser
    370                 375                 380

Leu Asp Ser Arg Val Gln Gln Ala Leu Asp Gly Leu
385                 390                 395

<210> SEQ ID NO 10
<211> LENGTH: 301
<212> TYPE: PRT
<213> ORGANISM: Methanosarcina mazei

<400> SEQUENCE: 10

Met Val Ser Cys Ser Ala Pro Gly Lys Ile Tyr Leu Phe Gly Glu His
1               5                   10                  15

Ala Val Val Tyr Gly Glu Thr Ala Ile Ala Cys Ala Val Glu Leu Arg
            20                  25                  30

Thr Arg Val Arg Ala Glu Leu Asn Asp Ser Ile Thr Ile Gln Ser Gln
        35                  40                  45

Ile Gly Arg Thr Gly Leu Asp Phe Glu Lys His Pro Tyr Val Ser Ala
    50                  55                  60

Val Ile Glu Lys Met Arg Lys Ser Ile Pro Ile Asn Gly Val Phe Leu
65                  70                  75                  80

Thr Val Asp Ser Asp Ile Pro Val Gly Ser Gly Leu Gly Ser Ser Ala
                85                  90                  95

Ala Val Thr Ile Ala Ser Ile Gly Ala Leu Asn Glu Leu Phe Gly Phe
            100                 105                 110

Gly Leu Ser Leu Gln Glu Ile Ala Lys Leu Gly His Glu Ile Glu Ile
        115                 120                 125

Lys Val Gln Gly Ala Ala Ser Pro Thr Asp Thr Tyr Val Ser Thr Phe
    130                 135                 140

Gly Gly Val Val Thr Ile Pro Glu Arg Arg Lys Leu Lys Thr Pro Asp
145                 150                 155                 160

Cys Gly Ile Val Ile Gly Asp Thr Gly Val Phe Ser Ser Thr Lys Glu
                165                 170                 175

Leu Val Ala Asn Val Arg Gln Leu Arg Glu Ser Tyr Pro Asp Leu Ile
            180                 185                 190

Glu Pro Leu Met Thr Ser Ile Gly Lys Ile Ser Arg Ile Gly Glu Gln
195 200 205

Leu Val Leu Ser Gly Asp Tyr Ala Ser Ile Gly Arg Leu Met Asn Val
210 215 220

Asn Gln Gly Leu Leu Asp Ala Leu Gly Val Asn Ile Leu Glu Leu Ser
225 230 235 240

Gln Leu Ile Tyr Ser Ala Arg Ala Ala Gly Ala Phe Gly Ala Lys Ile
245 250 255

Thr Gly Ala Gly Gly Gly Gly Cys Met Val Ala Leu Thr Ala Pro Glu
260 265 270

Lys Cys Asn Gln Val Ala Glu Ala Ile Ala Gly Ala Gly Gly Lys Val
275 280 285

Thr Ile Thr Lys Pro Thr Glu Gln Gly Leu Lys Val Asp
290 295 300

<210> SEQ ID NO 11
<211> LENGTH: 443
<212> TYPE: PRT
<213> ORGANISM: Saccharomyces cerevisiae

<400> SEQUENCE: 11

Met Ser Leu Pro Phe Leu Thr Ser Ala Pro Gly Lys Val Ile Ile Phe
1 5 10 15

Gly Glu His Ser Ala Val Tyr Asn Lys Pro Ala Val Ala Ala Ser Val
20 25 30

Ser Ala Leu Arg Thr Tyr Leu Leu Ile Ser Glu Ser Ser Ala Pro Asp
35 40 45

Thr Ile Glu Leu Asp Phe Pro Asp Ile Ser Phe Asn His Lys Trp Ser
50 55 60

Ile Asn Asp Phe Asn Ala Ile Thr Glu Asp Gln Val Asn Ser Gln Lys
65 70 75 80

Leu Ala Lys Ala Gln Gln Ala Thr Asp Gly Leu Ser Gln Glu Leu Val
85 90 95

Ser Leu Leu Asp Pro Leu Leu Ala Gln Leu Ser Glu Ser Phe His Tyr
100 105 110

His Ala Ala Phe Cys Phe Leu Tyr Met Phe Val Cys Leu Cys Pro His
115 120 125

Ala Lys Asn Ile Lys Phe Ser Leu Lys Ser Thr Leu Pro Ile Gly Ala
130 135 140

Gly Leu Gly Ser Ser Ala Ser Ile Ser Val Ser Leu Ala Leu Ala Met
145 150 155 160

Ala Tyr Leu Gly Gly Leu Ile Gly Ser Asn Asp Leu Glu Lys Leu Ser
165 170 175

Glu Asn Asp Lys His Ile Val Asn Gln Trp Ala Phe Ile Gly Glu Lys
180 185 190

Cys Ile His Gly Thr Pro Ser Gly Ile Asp Asn Ala Val Ala Thr Tyr
195 200 205

Gly Asn Ala Leu Leu Phe Glu Lys Asp Ser His Asn Gly Thr Ile Asn
210 215 220

Thr Asn Asn Phe Lys Phe Leu Asp Asp Phe Pro Ala Ile Pro Met Ile
225 230 235 240

Leu Thr Tyr Thr Arg Ile Pro Arg Ser Thr Lys Asp Leu Val Ala Arg
245 250 255

Val Arg Val Leu Val Thr Glu Lys Phe Pro Glu Val Met Lys Pro Ile

-continued

```
            260                 265                 270

Leu Asp Ala Met Gly Glu Cys Ala Leu Gln Gly Leu Glu Ile Met Thr
        275                 280                 285

Lys Leu Ser Lys Cys Lys Gly Thr Asp Asp Glu Ala Val Glu Thr Asn
    290                 295                 300

Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
                325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Leu Arg Arg Asp Ile Thr Gln
        355                 360                 365

Glu Gln Ile Asp Ser Phe Lys Lys Lys Leu Gln Asp Asp Phe Ser Tyr
    370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430

Leu Pro Gly Asn Thr Asn Leu Pro Trp Thr Ser
        435                 440


<210> SEQ ID NO 12
<211> LENGTH: 451
<212> TYPE: PRT
<213> ORGANISM: Saccharomyces cerevisiae

<400> SEQUENCE: 12

Met Ser Glu Leu Arg Ala Phe Ser Ala Pro Gly Lys Ala Leu Leu Ala
1               5                   10                  15

Gly Gly Tyr Leu Val Leu Asp Thr Lys Tyr Glu Ala Phe Val Val Gly
            20                  25                  30

Leu Ser Ala Arg Met His Ala Val Ala His Pro Tyr Gly Ser Leu Gln
        35                  40                  45

Gly Ser Asp Lys Phe Glu Val Arg Val Lys Ser Lys Gln Phe Lys Asp
    50                  55                  60

Gly Glu Trp Leu Tyr His Ile Ser Pro Lys Ser Gly Phe Ile Pro Val
65                  70                  75                  80

Ser Ile Gly Gly Ser Lys Asn Pro Phe Ile Glu Lys Val Ile Ala Asn
                85                  90                  95

Val Phe Ser Tyr Phe Lys Pro Asn Met Asp Asp Tyr Cys Asn Arg Asn
            100                 105                 110

Leu Phe Val Ile Asp Ile Phe Ser Asp Asp Ala Tyr His Ser Gln Glu
        115                 120                 125

Asp Ser Val Thr Glu His Arg Gly Asn Arg Arg Leu Ser Phe His Ser
    130                 135                 140

His Arg Ile Glu Glu Val Pro Lys Thr Gly Leu Gly Ser Ser Ala Gly
145                 150                 155                 160

Leu Val Thr Val Leu Thr Thr Ala Leu Ala Ser Phe Phe Val Ser Asp
                165                 170                 175

Leu Glu Asn Asn Val Asp Lys Tyr Arg Glu Val Ile His Asn Leu Ala
            180                 185                 190
```

-continued

```
Gln Val Ala His Cys Gln Ala Gln Gly Lys Ile Gly Ser Gly Phe Asp
        195                 200                 205

Val Ala Ala Ala Ala Tyr Gly Ser Ile Arg Tyr Arg Arg Phe Pro Pro
    210                 215                 220

Ala Leu Ile Ser Asn Leu Pro Asp Ile Gly Ser Ala Thr Tyr Gly Ser
225                 230                 235                 240

Lys Leu Ala His Leu Val Asp Glu Glu Asp Trp Asn Ile Thr Ile Lys
                245                 250                 255

Ser Asn His Leu Pro Ser Gly Leu Thr Leu Trp Met Gly Asp Ile Lys
            260                 265                 270

Asn Gly Ser Glu Thr Val Lys Leu Val Gln Lys Val Lys Asn Trp Tyr
        275                 280                 285

Asp Ser His Met Pro Glu Ser Leu Lys Ile Tyr Thr Glu Leu Asp His
    290                 295                 300

Ala Asn Ser Arg Phe Met Asp Gly Leu Ser Lys Leu Asp Arg Leu His
305                 310                 315                 320

Glu Thr His Asp Asp Tyr Ser Asp Gln Ile Phe Glu Ser Leu Glu Arg
                325                 330                 335

Asn Asp Cys Thr Cys Gln Lys Tyr Pro Glu Ile Thr Glu Val Arg Asp
            340                 345                 350

Ala Val Ala Thr Ile Arg Arg Ser Phe Arg Lys Ile Thr Lys Glu Ser
        355                 360                 365

Gly Ala Asp Ile Glu Pro Pro Val Gln Thr Ser Leu Leu Asp Asp Cys
    370                 375                 380

Gln Thr Leu Lys Gly Val Leu Thr Cys Leu Ile Pro Gly Ala Gly Gly
385                 390                 395                 400

Tyr Asp Ala Ile Ala Val Ile Thr Lys Gln Asp Val Asp Leu Arg Ala
                405                 410                 415

Gln Thr Ala Asn Asp Lys Arg Phe Ser Lys Val Gln Trp Leu Asp Val
            420                 425                 430

Thr Gln Ala Asp Trp Gly Val Arg Lys Glu Lys Asp Pro Glu Thr Tyr
        435                 440                 445

Leu Asp Lys
    450
```

<210> SEQ ID NO 13
<211> LENGTH: 396
<212> TYPE: PRT
<213> ORGANISM: Saccharomyces cerevisiae

<400> SEQUENCE: 13

```
Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110
```

-continued

```
Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
    290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
    370                 375                 380

Ser Leu Ile Asp Ala Lys Thr Gly Leu Pro Lys Glu
385                 390                 395


<210> SEQ ID NO 14
<211> LENGTH: 310
<212> TYPE: PRT
<213> ORGANISM: Lactococcus lactis

<400> SEQUENCE: 14

Met Thr Ile Asn Lys Met Gly Thr Gly Ile Ala His Ser Lys Leu Ile
1               5                   10                  15

Leu Ile Gly Glu His Ser Val Val Tyr Gly Gln Pro Ala Ile Ala Leu
            20                  25                  30

Pro Val Thr Ile Leu Lys Thr Thr Val Thr Ile Thr Ser Ser Lys Tyr
        35                  40                  45

Gly Gln Tyr Ile Glu Asn Asn Glu Phe Arg Arg Arg Leu Asp Leu Met
    50                  55                  60

Gly Asp Glu Phe Glu Gly Ile Arg Gln Leu Ile Met Arg Leu Leu Ser
65                  70                  75                  80

Lys Phe His Ser Ser Lys Met Pro Phe Ser Leu Glu Ile Asp Ser Asn
```

-continued

```
                85                  90                  95

Ile Pro Gln Gly Arg Gly Leu Gly Ala Ser Ala Ser Leu Ala Thr Ala
            100                 105                 110

Ile Ile Arg Ala Phe Tyr Asp Phe Phe Asp Ala Glu Leu Pro Gln Lys
        115                 120                 125

Asp Leu Leu Phe Tyr Ala Asn Phe Ser Glu Asn Ile Thr His Gly Lys
    130                 135                 140

Ser Ser Gly Ile Asp Val Ala Thr Val Asn Ser Glu His Pro Leu Trp
145                 150                 155                 160

Phe Ile Lys Asp Ser Thr Ile Glu Pro Phe Glu Leu Asn Leu His Gly
                165                 170                 175

Phe Ile Val Ile Gly Asp Thr Gly Val His Gly Phe Thr Ser Gln Ala
            180                 185                 190

Ile Asn Ile Val Arg Glu Lys Leu Val Glu Glu Lys Glu Lys Thr Gln
        195                 200                 205

Asp Ser Ile Asn His Leu Gly Gln Leu Ala Thr Asp Ser Lys Asp Phe
    210                 215                 220

Leu Met Thr Asp Lys Leu Lys Glu Phe Gly His Val Met Asn Lys Ala
225                 230                 235                 240

His Glu Arg Leu Ser Asp Leu Gly Val Ser His Pro Arg Leu Asp Asn
                245                 250                 255

Leu Val Glu Thr Ala Arg Lys Asn Gly Ala Leu Gly Ala Lys Leu Thr
            260                 265                 270

Gly Ser Gly Leu Gly Gly Val Met Val Ala Leu Ala Glu Asn Glu Lys
        275                 280                 285

Asp Ala Ile Arg Ile Ser Gln Arg Leu Leu Lys Asn Gly Ala Lys Asn
    290                 295                 300

Thr Trp Ile Tyr Ser Phe
305                 310


<210> SEQ ID NO 15
<211> LENGTH: 329
<212> TYPE: PRT
<213> ORGANISM: Lactococcus lactis

<400> SEQUENCE: 15

Met Asn Ile Ser Glu Lys Lys Met Ser Ile Lys Val Pro Gly Lys Leu
1               5                   10                  15

Phe Phe Ala Gly Glu Tyr Ser Val Thr Lys Glu Gly Asn Leu Ala Leu
            20                  25                  30

Ile Thr Thr Ile Glu Thr Asn Phe Glu Val Arg Ile Ser Ala Thr Thr
        35                  40                  45

Gly Lys Ser Ile Phe Lys Thr Asn Val Gly Leu Ser Asp Phe Glu Phe
    50                  55                  60

Ser Leu Ser Lys Ile Glu Phe Thr Lys Glu Asn Pro Trp Asn Phe Ala
65                  70                  75                  80

Leu Thr Ala Leu Lys Asn Thr Leu Ser Ala Ala Asp Ser Phe Glu Lys
                85                  90                  95

Lys Ser Val Ser Lys Ile Leu Ser Ser Ser Pro Glu Ile Ser Leu Glu
            100                 105                 110

Ile Val Ser Asp Leu Gly Phe Gly Glu Asn Lys Lys Gly Tyr Gly Ser
        115                 120                 125

Ser Ala Ser Val Val Cys Gly Leu Val Asn Ala Val Asn Gln Phe Phe
    130                 135                 140
```

-continued

```
Asp Phe Gln Leu Ser Leu Glu Lys Arg Phe Glu Ile Ala Ala Lys Thr
145                 150                 155                 160

His Phe Glu Val Gln Gly Ser Gly Ser Met Gly Asp Ile Ala Ala Ile
                165                 170                 175

Met Tyr Gly Gly Ser Val Phe Tyr Gln Asn His Lys Arg Val Ile Pro
            180                 185                 190

Leu Glu Ile Pro Trp Ala Thr Tyr Val Val Gln Thr Gly Lys Ala Ala
        195                 200                 205

Lys Thr Ser Glu Lys Ile Lys Ile Lys Leu Ser Asp Glu Phe Tyr Gln
    210                 215                 220

Ala Ser Asn Glu Leu Val Ile Glu Leu Ala Thr Ala Ile Asp Ile Gln
225                 230                 235                 240

Asp Phe Ala Leu Phe Lys Glu Lys Leu Ser Glu Asn Gln Leu Leu Leu
                245                 250                 255

Leu Glu Asn Ile Pro Glu Gly Tyr Met Thr Lys Glu Leu Ala Ile Ala
            260                 265                 270

Leu Asn Leu Leu Asn Ser Tyr Pro Glu Phe Ala Ala Lys Ile Ser Gly
        275                 280                 285

Ala Gly Phe Gly Glu Asn Ile Ile Leu Phe Ala Gln Asn Thr Gln Ala
    290                 295                 300

Ile Ala Glu Val Gln Asn Lys Leu Ser Glu Tyr Gly Ile Asn Leu Glu
305                 310                 315                 320

Lys Phe Lys Val Ala Gln Lys Asn Asn
                325


<210> SEQ ID NO 16
<211> LENGTH: 318
<212> TYPE: PRT
<213> ORGANISM: Lactococcus lactis

<400> SEQUENCE: 16

Met Lys Asn Ile Val Thr Ala Arg Ala His Thr Asn Ile Ala Leu Ile
1               5                   10                  15

Lys Tyr Trp Gly Lys Ala Asp Ile Ala Leu Asn Ile Pro Thr Thr Ser
            20                  25                  30

Ser Leu Ser Met Thr Leu Glu Pro Phe Tyr Thr Thr Thr Ser Val Glu
        35                  40                  45

Phe Thr Asp Asn Glu Ser Asp Ser Leu Ile Leu Asn Ser Glu Val Ala
    50                  55                  60

Asp Ser Ser Arg Val Ser Gln Phe Leu Glu Met Met Arg Gly Gln Tyr
65                  70                  75                  80

Gly Asn Phe Pro Lys Val Met Ile Gln Ser Glu Asn His Val Pro Thr
                85                  90                  95

Ala Ala Gly Leu Ala Ser Ser Ala Ser Ser Phe Ala Ala Leu Thr Ala
            100                 105                 110

Ala Met Phe Gly Leu Leu Asp Leu Glu Lys Asp Asp Ser Glu Met Ser
        115                 120                 125

Arg Ile Ala Arg Arg Gly Ser Gly Ser Ala Ser Arg Ser Ile Phe Gly
    130                 135                 140

Asn Phe Ser Val Trp Asn Lys Gly Glu Asp His Gln Ser Ser Phe Ala
145                 150                 155                 160

Glu Ser Phe Tyr Asn Glu Asp Ile Gly Leu Ser Met Ile Val Ala Glu
                165                 170                 175

Ile Ser Ala Glu Lys Lys Lys Met Ser Ser Thr Lys Gly Met Gln Leu
            180                 185                 190
```

Ala Gln Thr Ala Pro Thr Tyr Ser Ala Trp Val Glu Lys Ser Ala Ile
195 200 205

Gln Leu Glu Glu Met Lys Gln Ala Ile Leu Asn Ala Asp Ile Glu Lys
210 215 220

Val Gly Leu Val Ala Gln Asp Asn Ala Leu Gly Met His Glu Gln Asn
225 230 235 240

Arg Leu Ser Asn Gln Pro Phe Asp Tyr Phe Thr His Glu Thr Arg His
245 250 255

Val Ile Asp Phe Val Asn Gln Ala Tyr Gln Ser Gly Leu Leu Ala Phe
260 265 270

Val Thr Ile Asp Ala Gly Pro Asn Val Lys Ile Ile Thr Asp His Ala
275 280 285

Thr Glu Lys Val Leu Leu Ala Lys Leu Gln Ala Glu Phe Pro Glu Leu
290 295 300

Thr Phe Asp Ile Ala Arg Ala Gly Gly Ala Tyr Glu Tyr Leu
305 310 315

<210> SEQ ID NO 17
<211> LENGTH: 322
<212> TYPE: PRT
<213> ORGANISM: Listeria monocytogenes

<400> SEQUENCE: 17

Met Ala Thr Gly Ile Gly Thr Ala Lys Met Ile Leu Cys Gly Glu His
1 5 10 15

Ala Val Val Tyr Gly Glu Pro Ala Ile Ser Val Pro Phe Thr Gln Ala
20 25 30

Val Val Thr Thr Asn Val Glu Thr Ser Ile Lys Thr Lys Phe Ser Ser
35 40 45

Ala Phe Phe Ser Gly Asp Leu Asp Asp Met Pro Asp Phe Leu Ala Gly
50 55 60

Ile Lys Ala Leu Val Val Asp Val Leu Asn Glu Ile Gly Asn Gly Glu
65 70 75 80

Cys Val Ser Ile His Val Val Ser Gly Val Pro Ile Gly Arg Gly Leu
85 90 95

Gly Ser Ser Ala Ala Val Ala Thr Ser Ile Ala Arg Gly Leu Tyr Lys
100 105 110

Tyr Phe Asn Gln Glu Leu Asp Ser Lys Lys Leu Leu Ala Ile Val Asn
115 120 125

Ala Ala Glu Lys Ile Ala His Gly Asn Ala Ser Gly Val Asp Ala Ile
130 135 140

Thr Val Val Ser Glu Lys Pro Val Trp Tyr Glu Arg Asp Arg Lys Leu
145 150 155 160

Glu Ile Met His Phe Pro Lys Lys Ile Thr Phe Val Val Ala Asp Thr
165 170 175

Gly Val Pro Ser Glu Thr Arg Asp Ala Val Lys Asp Val Gln Val Leu
180 185 190

Tyr Lys Glu Asn Gln Val Glu Ile Gly Lys Ile Ile His Gln Leu Gly
195 200 205

Asp Ile Ser Arg Glu Ile Lys Thr His Leu Glu Gly Asp Ala Asp Thr
210 215 220

Val Lys Ile Gly Ala Ala Met Asn Lys Ala Gln Ser Tyr Leu Glu Thr
225 230 235 240

Leu Thr Val Ser Asp Ser Ser Leu Glu Lys Leu Ile Lys Val Ala Arg

-continued

```
                245                 250                 255

Ser Asn Gly Ala Asp Gly Ala Lys Leu Thr Gly Gly Gly Arg Gly Gly
            260                 265                 270

Cys Ile Ile Ala Val Ala Lys Asn Gln Glu Ile Ala Glu Gln Ile Thr
        275                 280                 285

Lys Ala Leu His Asn Ala Gly Ala Ala Gln Glu Trp Ile Phe Thr Ile
    290                 295                 300

Gly Glu Gly Ser Tyr Glu Ser Asp Ser His Arg Thr His Glu Cys Gly
305                 310                 315                 320

Ala Asn


<210> SEQ ID NO 18
<211> LENGTH: 359
<212> TYPE: PRT
<213> ORGANISM: Listeria monocytogenes

<400> SEQUENCE: 18

Met Tyr Gln Met Lys Asn Lys Leu Gln Val Lys Ile Pro Gly Lys Leu
1               5                   10                  15

Tyr Val Ala Gly Glu Tyr Ala Val Val Glu Ser Gly His Thr Ala Ile
            20                  25                  30

Leu Thr Ala Val Asn Arg Tyr Ile Thr Leu Thr Leu Glu Asp Ser Glu
        35                  40                  45

Arg Asn Glu Leu Trp Ile Pro His Tyr Glu Asn Pro Val Ser Trp Pro
    50                  55                  60

Val Gly Gly Glu Leu Lys Pro Asp Gly Glu His Trp Thr Phe Thr Ala
65                  70                  75                  80

Glu Ala Ile Asn Ile Ala Thr Thr Phe Leu Lys Ser Glu Gly Ile Glu
                85                  90                  95

Leu Thr Pro Val Lys Met Ile Ile Glu Thr Glu Leu Ile Asp Gln Ser
            100                 105                 110

Gly Ala Lys Tyr Gly Leu Gly Ser Ser Ala Ala Ala Thr Val Ala Val
        115                 120                 125

Ile Asn Ala Leu Met Thr Lys Phe Tyr Pro Glu Ile Ser Met Leu Lys
    130                 135                 140

Lys Phe Lys Leu Ala Ala Leu Ser His Leu Val Val Gln Gly Asn Gly
145                 150                 155                 160

Ser Cys Gly Asp Ile Ala Ser Cys Met Tyr Gly Gly Trp Ile Ala Tyr
                165                 170                 175

Thr Thr Phe Asp Gln Glu Trp Val Lys His Arg Leu Ala Tyr Lys Ser
            180                 185                 190

Leu Glu Trp Phe Met Lys Glu Pro Trp Pro Met Leu Gln Ile Glu Thr
        195                 200                 205

Leu Glu Glu Pro Val Pro Thr Phe Ser Val Gly Trp Thr Gly Thr Pro
    210                 215                 220

Val Ser Thr Gly Lys Leu Val Ser Gln Ile His Ala Phe Lys Gln Glu
225                 230                 235                 240

Asp Ser Lys Asn Tyr Gln His Phe Leu Thr Arg Asn Asn Glu Ile Met
                245                 250                 255

Lys Gln Ile Ile Gln Ala Phe His Thr Lys Asp Glu Glu Leu Leu Tyr
            260                 265                 270

Ser Ala Ile Lys Glu Asn Arg Arg Ile Leu Gln Glu Leu Gly Thr Lys
        275                 280                 285

Ala Gly Val Asn Ile Glu Thr Ser Leu Leu Lys Glu Leu Ala Asp Ser
```

-continued

```
    290                 295                 300

Ala Glu Asn Met Gly Gly Ala Gly Lys Ser Ser Gly Ser Gly Gly Gly
305                 310                 315                 320

Asp Cys Gly Ile Ala Phe Ser Lys Thr Lys Glu Leu Ala Glu Lys Leu
                325                 330                 335

Val Asn Glu Trp Glu Lys Leu Gly Ile Lys His Leu Pro Phe His Thr
            340                 345                 350

Gly Arg Val Gln Ile Thr Glu
        355


<210> SEQ ID NO 19
<211> LENGTH: 323
<212> TYPE: PRT
<213> ORGANISM: Listeria monocytogenes

<400> SEQUENCE: 19

Met Lys Ala Thr Ala Ile Ala His Thr Asn Val Ala Leu Ile Lys Tyr
1               5                   10                  15

Trp Gly Lys Arg Asp Glu His Leu Ile Leu Pro Ala Asn Ser Ser Leu
            20                  25                  30

Ser Phe Thr Val Asp Lys Phe Tyr Thr Lys Thr Thr Val Glu Trp Asp
        35                  40                  45

Glu Lys Leu Thr Gln Asp Thr Phe Ile Leu Asn Asn Glu Gln Lys Thr
    50                  55                  60

Asp Ala Lys Val Ala Arg Phe Ile Asp Lys Met Arg Glu Glu Phe Gly
65                  70                  75                  80

Ile Ser Ala Lys Ala Lys Ile Thr Ser Glu Asn His Val Pro Thr Ala
                85                  90                  95

Ala Gly Leu Ala Ser Ser Ala Ser Ala Phe Ala Ala Leu Ala Leu Ala
            100                 105                 110

Gly Ser Asn Ala Ala Gly Arg Lys Asp Thr Lys Glu Tyr Ile Ser Arg
        115                 120                 125

Leu Ala Arg Phe Gly Ser Gly Ser Ala Ser Arg Ser Val Phe Gly Asp
    130                 135                 140

Phe Val Ile Trp Glu Lys Gly Glu Leu Ala Asp Gly Ser Asp Ser Phe
145                 150                 155                 160

Ala Val Pro Phe Thr Asn Lys Leu Cys Asp Lys Met Ser Leu Val Val
                165                 170                 175

Ala Val Val Ser Asp Lys Glu Lys Lys Val Ser Ser Arg Asp Gly Met
            180                 185                 190

Arg Leu Thr Val Glu Thr Ser Pro Phe Phe Glu Asn Trp Val Ser Ala
        195                 200                 205

Ala Glu Ile Asp Leu Glu Glu Met Lys Gln Ala Ile Leu Asp Glu Asp
    210                 215                 220

Phe Ile Lys Val Gly Glu Ile Thr Glu Arg Asn Gly Met Lys Met His
225                 230                 235                 240

Ala Thr Thr Leu Gly Ala Glu Pro Pro Phe Thr Tyr Phe Gln Pro Gln
                245                 250                 255

Ser Leu Glu Ile Met Asp Ala Val Arg Glu Leu Arg Glu Asn Gly Ile
            260                 265                 270

Pro Ala Tyr Phe Thr Met Asp Ala Gly Pro Asn Val Lys Val Ile Cys
        275                 280                 285

Glu Arg Ala Asn Glu Asn Ile Val Ala Glu Lys Leu Ser Gly Leu Ala
    290                 295                 300
```

Lys Asn Val Leu Ile Cys His Ala Gly Lys Glu Ala Ser Val Val Ser
305 310 315 320

Asp Glu Lys

<210> SEQ ID NO 20
<211> LENGTH: 314
<212> TYPE: PRT
<213> ORGANISM: Enterococcus faecalis

<400> SEQUENCE: 20

Met Asn Ile Lys Lys Gln Gly Leu Gly Gln Ala Thr Gly Lys Ile Ile
1 5 10 15

Leu Met Gly Glu His Ala Val Val Tyr Gly Glu Pro Ala Ile Ala Phe
20 25 30

Pro Phe Gln Ala Thr Glu Ile Thr Ala Val Phe Thr Leu Ala Lys Thr
35 40 45

Met Gln Ile Asp Cys Ala Tyr Phe Thr Gly Leu Leu Glu Asp Val Pro
50 55 60

Gln Glu Leu Ala Asn Ile Lys Glu Val Val Gln Gln Thr Leu His Phe
65 70 75 80

Leu Lys Glu Asp Thr Phe Lys Gly Thr Leu Thr Leu Thr Ser Thr Ile
85 90 95

Pro Ala Glu Arg Gly Met Gly Ser Ser Ala Ala Thr Ala Val Ala Ile
100 105 110

Val Arg Ser Leu Phe Asp Tyr Phe Asp Tyr Ala Tyr Thr Tyr Gln Glu
115 120 125

Leu Phe Glu Leu Val Ser Leu Ser Glu Lys Ile Ala His Gly Asn Pro
130 135 140

Ser Gly Ile Asp Ala Ala Ala Thr Ser Gly Ala Asp Pro Leu Phe Phe
145 150 155 160

Thr Arg Gly Phe Pro Pro Thr His Phe Ser Met Asn Leu Ser Asn Ala
165 170 175

Tyr Leu Val Val Ala Asp Thr Gly Ile Lys Gly Gln Thr Arg Glu Ala
180 185 190

Val Lys Asp Ile Ala Gln Leu Ala Gln Asn Asn Pro Thr Ala Ile Ala
195 200 205

Glu Thr Met Lys Gln Leu Gly Ser Phe Thr Lys Glu Ala Lys Gln Ala
210 215 220

Ile Leu Gln Asp Asp Lys Gln Lys Leu Gly Gln Leu Met Thr Leu Ala
225 230 235 240

Gln Glu Gln Leu Gln Gln Leu Ser Val Ser Asn Asp Met Leu Asp Arg
245 250 255

Leu Val Ala Leu Ser Leu Glu His Gly Ala Leu Gly Ala Lys Leu Thr
260 265 270

Gly Gly Gly Arg Gly Gly Cys Met Ile Ala Leu Thr Asp Asn Lys Lys
275 280 285

Thr Ala Gln Thr Ile Ala Gln Thr Leu Glu Glu Asn Gly Ala Val Ala
290 295 300

Thr Trp Ile Gln Ser Leu Glu Val Lys Lys
305 310

<210> SEQ ID NO 21
<211> LENGTH: 368
<212> TYPE: PRT
<213> ORGANISM: Enterococcus faecalis -continued

<400> SEQUENCE: 21

```
Met Ile Glu Val Thr Thr Pro Gly Lys Leu Phe Ile Ala Gly Glu Tyr
1               5                   10                  15

Ala Val Val Glu Pro Gly His Pro Ala Ile Ile Val Ala Val Asp Gln
            20                  25                  30

Phe Val Thr Val Thr Val Glu Glu Thr Thr Asp Glu Gly Ser Ile Gln
        35                  40                  45

Ser Ala Gln Tyr Ser Ser Leu Pro Ile Arg Trp Thr Arg Arg Asn Gly
    50                  55                  60

Glu Leu Val Leu Asp Ile Arg Glu Asn Pro Phe His Tyr Val Leu Ala
65                  70                  75                  80

Ala Ile His Leu Thr Glu Lys Tyr Ala Gln Glu Gln Asn Lys Glu Leu
                85                  90                  95

Ser Phe Tyr His Leu Lys Val Thr Ser Glu Leu Asp Ser Ser Asn Gly
            100                 105                 110

Arg Lys Tyr Gly Leu Gly Ser Ser Gly Ala Val Thr Val Gly Thr Val
        115                 120                 125

Lys Ala Leu Asn Ile Phe Tyr Asp Leu Gly Leu Glu Asn Glu Glu Ile
    130                 135                 140

Phe Lys Leu Ser Ala Leu Ala His Leu Ala Val Gln Gly Asn Gly Ser
145                 150                 155                 160

Cys Gly Asp Ile Ala Ala Ser Cys Tyr Gly Gly Trp Ile Ala Phe Ser
                165                 170                 175

Thr Phe Asp His Asp Trp Val Asn Gln Lys Val Ala Thr Glu Thr Leu
            180                 185                 190

Thr Asp Leu Leu Ala Met Asp Trp Pro Glu Leu Met Ile Phe Pro Leu
        195                 200                 205

Lys Val Pro Lys Gln Leu Arg Leu Leu Ile Gly Trp Thr Gly Ser Pro
    210                 215                 220

Ala Ser Thr Ser Asp Leu Val Asp Arg Val His Gln Ser Lys Glu Glu
225                 230                 235                 240

Lys Gln Ala Ala Tyr Glu Gln Phe Leu Met Lys Ser Arg Leu Cys Val
                245                 250                 255

Glu Thr Met Ile Asn Gly Phe Asn Thr Gly Lys Ile Ser Val Ile Gln
            260                 265                 270

Lys Gln Ile Thr Lys Asn Arg Gln Leu Leu Ala Glu Leu Ser Ser Leu
        275                 280                 285

Thr Gly Val Val Ile Glu Thr Glu Ala Leu Lys Asn Leu Cys Asp Leu
    290                 295                 300

Ala Glu Ser Tyr Thr Gly Ala Ala Lys Ser Ser Gly Ala Gly Gly Gly
305                 310                 315                 320

Asp Cys Gly Ile Val Ile Phe Arg Gln Lys Ser Gly Ile Leu Pro Leu
                325                 330                 335

Met Thr Ala Trp Glu Lys Asp Gly Ile Thr Pro Leu Pro Leu His Val
            340                 345                 350

Tyr Thr Tyr Gly Gln Lys Glu Cys Lys Glu Lys His Glu Ser Lys Arg
        355                 360                 365
```

<210> SEQ ID NO 22
<211> LENGTH: 331
<212> TYPE: PRT
<213> ORGANISM: Enterococcus faecalis

<400> SEQUENCE: 22

-continued

```
Met Leu Ser Gly Lys Ala Arg Ala His Thr Asn Ile Ala Leu Ile Lys
1               5                   10                  15

Tyr Trp Gly Lys Ala Asn Glu Glu Tyr Ile Leu Pro Met Asn Ser Ser
            20                  25                  30

Leu Ser Leu Thr Leu Asp Ala Phe Tyr Thr Glu Thr Thr Val Ile Phe
        35                  40                  45

Asp Ala His Tyr Ser Glu Asp Val Phe Ile Leu Asp Gly Ile Leu Gln
    50                  55                  60

Asn Glu Lys Gln Thr Lys Lys Val Lys Glu Phe Leu Asn Leu Val Arg
65                  70                  75                  80

Gln Gln Ala Asp Cys Thr Trp Phe Ala Lys Val Glu Ser Gln Asn Phe
                85                  90                  95

Val Pro Thr Ala Ala Gly Leu Ala Ser Ser Ala Ser Gly Leu Ala Ala
            100                 105                 110

Leu Ala Gly Ala Cys Asn Val Ala Leu Gly Leu Asn Leu Ser Ala Lys
        115                 120                 125

Asp Leu Ser Arg Leu Ala Arg Arg Gly Ser Gly Ser Ala Cys Arg Ser
    130                 135                 140

Ile Phe Gly Gly Phe Ala Gln Trp Asn Lys Gly His Ser Asp Glu Thr
145                 150                 155                 160

Ser Phe Ala Glu Asn Ile Pro Ala Asn Asn Trp Glu Asn Glu Leu Ala
                165                 170                 175

Met Leu Phe Ile Leu Ile Asn Asp Gly Glu Lys Asp Val Ser Ser Arg
            180                 185                 190

Asp Gly Met Lys Arg Thr Val Glu Thr Ser Ser Phe Tyr Gln Gly Trp
        195                 200                 205

Leu Asp Asn Val Glu Lys Asp Leu Ser Gln Val His Glu Ala Ile Lys
    210                 215                 220

Thr Lys Asp Phe Pro Arg Leu Gly Glu Ile Ile Glu Ala Asn Gly Leu
225                 230                 235                 240

Arg Met His Gly Thr Thr Leu Gly Ala Val Pro Pro Phe Thr Tyr Trp
                245                 250                 255

Ser Pro Gly Ser Leu Gln Ala Met Ala Leu Val Arg Gln Ala Arg Ala
            260                 265                 270

Lys Gly Ile Pro Cys Tyr Phe Thr Met Asp Ala Gly Pro Asn Val Lys
        275                 280                 285

Val Leu Val Glu Lys Lys Asn Leu Glu Ala Leu Lys Thr Phe Leu Ser
    290                 295                 300

Glu His Phe Ser Lys Glu Gln Leu Val Pro Ala Phe Ala Gly Pro Gly
305                 310                 315                 320

Ile Glu Leu Phe Glu Thr Lys Gly Met Asp Lys
                325                 330
```

<210> SEQ ID NO 23
<211> LENGTH: 2412
<212> TYPE: DNA
<213> ORGANISM: Enterococcus faecalis

<400> SEQUENCE: 23

```
atgaaaaccg tggtcatcat cgatgccctg cgcaccccga tcggcaagta taagggctcc      60

ctctcccaag tgtcggccgt ggacctgggt acccacgtga ccacccaact cctgaagcgc     120

catagcacga tctccgaaga gatcgaccag gtgatctttg gcaacgtgct ccaggccggc     180

aacggccaga acccggcccg ccagatcgcc atcaactccg gcctgagcca cgaaatcccc     240
```

-continued

```
gccatgaccg tgaacgaagt ctgcggctcg ggcatgaagg ccgtcatcct ggcgaagcag    300
ctcatccagc tcggcgaagc ggaagtgctg atcgccggcg gcatcgagaa tatgtcgcag    360
gcgccgaagc tgcagcgctt caactatgaa accgagtcgt acgacgcgcc gttcagctcc    420
atgatgtacg acggcctgac ggacgccttc tccggccaag ccatgggcct gacggcggaa    480
aacgtggccg agaagtacca cgtgacgcgc gaggaacagg accagttctc ggtccattcg    540
cagctgaagg ccgcccaggc ccaggccgag ggcatctttg cggacgagat cgcgccgctg    600
gaggtcagcg gcaccctggt ggaaaaggac gaaggcattc gccccaactc ctcggtcgag    660
aagctgggca ccctcaagac cgtgttcaag gaggacggca ccgtcaccgc gggcaatgcc    720
tcgaccatca acgacggcgc gtcggccctc atcatcgcga gccaggaata cgcggaagcg    780
catggcctgc cgtacctcgc gatcatccgt gactccgtgg aagtcggcat cgacccggcg    840
tacatgggca tctcccccat caaggccatc caaaagctcc tggcgcgcaa ccagctgacg    900
acggaggaga tcgacctgta cgagatcaac gaagcgttcg cggcgacgag catcgtggtg    960
cagcgcgagc tggccctgcc ggaggaaaag gtgaatatct acggcggcgg catttcgctg   1020
ggccatgcga tcggcgcgac cggcgcccgc ctgctgacca gcctgtcgta tcaactcaat   1080
caaaaggaaa agaagtacgg cgtggcgtcg ctgtgcatcg gcggtggcct gggcctcgcc   1140
atgctgctgg agcgcccgca gcagaagaag aactcgcgct tttaccagat gtcgcccgag   1200
gaacggctgg cgtcgctcct gaacgaaggc caaatctcgg ccgataccaa gaaggagttc   1260
gaaaacaccg ccctgtcgag ccagatcgcg aaccacatga tcgaaaatca gatcagcgaa   1320
accgaagtgc cgatgggcgt gggcctccat ctgaccgtgg acgaaacgga ctatctggtc   1380
ccgatggcca ccgaggaacc gtcggtgatc gccgcgctgt ccaacggcgc caagatcgcc   1440
cagggcttca agacggtgaa ccagcagcgc ctgatgcgcg gtcagatcgt gttctacgat   1500
gtggcggacc cggagtcgct gatcgacaag ctccaggtgc gtgaagccga agtgttccag   1560
caagccgaac tgtcgtaccc cagcatcgtc aagcgcggcg gcggcctccg cgatctccag   1620
taccgcacct tcgacgagtc gttcgtgtcg gtcgattttc tggtggatgt gaaggacgcc   1680
atgggtgcga acatcgtcaa cgccatgctg gaaggcgtcg ccgaactgtt ccgggagtgg   1740
ttcgccgagc agaagatcct gttcagcatc ctctcgaact acgccaccga gtccgtggtg   1800
accatgaaaa ccgccattcc cgtcagccgc ctgtcgaagg gcagcaacgg ccgcgagatc   1860
gcggaaaaga tcgtcctcgc ctcccgctac gcgtcgctgg acccgtatcg cgcggtcacc   1920
cacaacaagg gcattatgaa cggcatcgag gccgtcgtgc tggccaccgg caatgacacg   1980
cgcgccgtgt cggccagctg ccatgccttc gccgtgaagg aaggccggta ccaaggcctg   2040
accagctgga cgctggacgg cgaacagctg atcggcgaaa tcagcgtgcc cctggccctg   2100
gcgaccgtgg gcggcgcgac caaggtcctg cccaagagcc aggccgcggc cgatctgctg   2160
gccgtgaccg atgccaagga gctgtcccgc gtggtcgccg cggtgggtct ggcgcagaat   2220
ctggccgccc tgcgggcgct ggtcagcgag ggcatccaaa agggccacat ggcgctgcag   2280
gcccgcagcc tggcgatgac ggtgggcgcc accggtaagg aagtggaagc cgtcgcgcag   2340
cagctcaagc gtcaaaagac gatgaaccaa gaccgcgcca tggccatcct gaacgatctg   2400
cgcaagcagt ga                                                       2412
```

<210> SEQ ID NO 24
<211> LENGTH: 1152
<212> TYPE: DNA
<213> ORGANISM: Enterococcus faecalis

<400> SEQUENCE: 24
atgaccatcg gcattgacaa gatttccttt ttcgtcccgc cgtactacat cgacatgacg 60
gccctcgccg aggcgcgcaa cgtggacccc ggcaagttcc acatcggcat cggccaggat 120
cagatggccg tcaacccgat ctcgcaggat atcgtgacct ttgccgccaa cgcggccgag 180
gccatcctga ccaaggagga caaagaagcc atcgacatgg tcatcgtggg caccgagtcg 240
tcgatcgatg agagcaaggc cgcggccgtc gtgctgcacc ggctgatggg catccaaccc 300
ttcgcccgct ccttcgagat taaggaagcc tgctacggtg cgaccgcggg cctccagctg 360
gcgaagaacc acgtggccct gcacccggat aagaaggtcc tggtggtggc cgcggacatc 420
gcgaagtacg gcctgaatag cggtggcgag ccgacgcagg gcgcgggcgc ggtggccatg 480
ctggtcgcct cggagccgcg catcctggcc ctcaaggaag ataacgtgat gctgacgcag 540
gacatctacg acttctggcg ccccaccggc catccgtatc cgatggtgga cggtcccctg 600
tccaatgaaa cctacatcca gtcgttcgcg caagtctggg acgaacacaa gaagcgcacg 660
ggcctcgact tcgccgacta tgacgcgctg gccttccaca tcccgtacac caagatgggc 720
aagaaggccc tgctcgccaa gatcagcgac cagaccgagg ccgaacagga acgcatcctc 780
gcgcgctatg aagagtcgat cgtctactcg cgtcgggtgg gcaacctgta caccggctcg 840
ctgtacctgg gcctgatcag cctgctggag aacgcgacga ccctgacggc gggcaaccag 900
atcggcctgt tctcgtacgg tagcggcgcc gtggccgagt tcttcaccgg cgagctggtc 960
gcgggctacc agaatcatct gcaaaaggaa acccatctgg cgctgctgga caaccgcacc 1020
gaactgagca tcgccgagta cgaagccatg ttcgccgaaa ccctggacac cgacatcgac 1080
cagaccctgg aagatgagct gaagtatagc atctccgcga tcaacaatac ggtgcgcagc 1140
tatcgcaact ga 1152

<210> SEQ ID NO 25
<211> LENGTH: 879
<212> TYPE: DNA
<213> ORGANISM: Streptococcus pneumoniae

<400> SEQUENCE: 25
atgaccaaga aggtcggcgt gggccaggcc cacagcaaga tcattctgat cggcgagcac 60
gccgtggtgt atggctaccc ggccatcagc ctgccgctgc tggaagtcga agtgacgtgc 120
aaggtggtgc cggccgaatc cccgtggcgt ctgtatgaag aggacacgct gtcgatggcc 180
gtgtatgcca gcctggagta cctgaacatc accgaggcct gcatccgctg cgagatcgac 240
tccgcgatcc cggagaagcg cggcatgggc agctcggccg ccatctccat cgccgcgatc 300
cgcgccgtgt tcgactacta ccaagcggat ctgccgcatg acgtgctgga gatcctggtg 360
aaccgggccg aaatgatcgc ccacatgaat ccgagcggtc tggatgccaa gacgtgcctg 420
tccgaccagc cgatccgttt catcaagaac gtgggtttca ccgagctgga gatggatctg 480
agcgcgtacc tggtgatcgc ggacaccggc gtgtacggcc acacccgcga ggccatccag 540
gtcgtgcaaa ataagggtaa ggacgccctg cccctttctgc acgccctggg cgaactcacc 600
cagcaggccg aagtcgcgat ttcccagaag gacgccgagg gcctgggtca aatcctgagc 660
caggcgcatc tgcacctgaa ggagatcggc gtgagcagcc cggaagcgga cttcctggtc 720
gaaaccaccc tgtcgcacgg tgccctgggc gcgaagatgt cgggcggcgg cctgggcggc 780
tgcatcatcg cgctggtcac caacctgacc catgcgcaag agctggccga gcgcctggaa 840

-continued gaaaagggcg ccgtccagac gtggatcgaa tcgctctga 879

<210> SEQ ID NO 26
<211> LENGTH: 1008
<212> TYPE: DNA
<213> ORGANISM: Streptococcus pneumoniae

<400> SEQUENCE: 26
atgatcgccg tcaagacgtg cggcaagctg tactgggcgg gcgagtatgc catcctcgaa 60
cccggccagc tggccctgat caaggacatc ccgatctata tgcgtgccga aatcgcgttc 120
agcgattcgt accgcatcta ttcggatatg ttcgacttcg ccgtcgatct gcgccccaat 180
cccgactact cgctgatcca agaaaccatc gcgctcatgg gcgacttcct cgccgtccgc 240
ggtcagaatc tgcgcccgtt cagcctggag atttgcggca agatggagcg cgagggtaag 300
aagttcggcc tgggctcctc gggctccgtg gtggtcctgg tcgtgaaggc gctgctggcg 360
ctgtacgatg tctcggtgga ccaagagctg ctgttcaagc tgacctcggc cgtgctcctg 420
aagcgcggcg acaacggctc catgggcgac ctcgcgtgca tcgtggccga ggacctggtc 480
ctgtaccagt cgtttgaccg ccagaaggtg gcggcgtggc tggaagaaga gaacctggcc 540
acggtgctgg agcgtgactg gggcttctcc atctcccagg tgaagccgac cctggaatgc 600
gacttcctcg tgggctggac caaggaagtg gcggtgtcca gccacatggt gcaacagatc 660
aagcagaaca ttaaccagaa ttttctgacc tcgtcgaagg aaaccgtcac gagcctggtg 720
gaagccctgg agcagggcaa gtcggagaag atcatcgacc aggtcgaggt cgcctccaag 780
ctgctggaag gcctgtccac ggatatctac acccccctgc tgcgccaact gaaggaagcc 840
tcgcaggacc tccagaccgt ggccaagagc agcggcgccg gcggcggcga ctgcggcatc 900
gccctgtcct tcgacgcgca gtccaccaag accctgaaga accggtgggc ggacctgggc 960
atcgagctcc tgtaccaaga gcggatcggc cacgacgaca agtcgtga 1008

<210> SEQ ID NO 27
<211> LENGTH: 954
<212> TYPE: DNA
<213> ORGANISM: Streptococcus pneumoniae

<400> SEQUENCE: 27
atggaccgcg aaccggtcac cgtgcgctcg tacgcgaaca tcgccatcat caagtattgg 60
ggcaagaaga aggaaaagga aatggtcccg gccacctcca gcatctcgct gacgctggag 120
aatatgtaca ccgaaacgac cctgtcgccc ctgcccgcga acgtcaccgc ggacgagttc 180
tatatcaacg gccagctgca gaacgaagtg gagcatgcga agatgagcaa gattatcgat 240
cggtaccgcc cggccggcga gggctttgtg cgcatcgaca cgcagaataa catgccgacg 300
gccgcgggcc tgagcagcag ctcgtcgggc ctctccgccc tggtcaaggc ctgcaacgcc 360
tacttcaagc tgggcctgga ccgctcgcag ctcgcgcaag aagccaagtt tgccagcggc 420
tcgtcctccc gcagctttta cggcccgctg ggcgcgtggg acaaggactc gggcgaaatc 480
tacccggtgg aaacggacct caagctggcc atgatcatgc tggtcctgga agataagaag 540
aagccgatct ccagccgcga cggcatgaag ctgtgcgtcg aaaccagcac cacgttcgat 600
gactgggtgc ggcagagcga aaaggactac caagacatgc tgatttacct gaaggaaaac 660
gacttcgcga agatcggcga actgaccgag aagaatgcgc tggcgatgca cgcgacgacc 720
aagaccgcct cgcccgcctt ctcgtacctg accgacgcca gctacgaagc catggccttc 780
gtgcgccaac tccgcgaaaa gggcgaggcg tgctacttca cgatggacgc cggcccgaac 840
gtcaaggtgt tctgccagga aaaggatctg gaacatctgt ccgaaatctt cggccaccgc 900
taccgcctga tcgtgagcaa gaccaaggat ctgtcgcaag acgactgctg ctga 954

<210> SEQ ID NO 28
<211> LENGTH: 1011
<212> TYPE: DNA
<213> ORGANISM: Streptococcus pneumoniae

<400> SEQUENCE: 28
atgacgacca accgcaagga tgagcacatc ctctacgccc tggagcagaa gtcgtcgtac 60
aactcgttcg acgaagtgga actgatccac tcgtcgctgc cgctgtataa cctggacgaa 120
atcgacctgt ccaccgagtt cgccggccgc aagtgggatt tcccgttcta catcaatgcc 180
atgaccggcg gtagcaacaa gggccgcgaa atcaatcaga agctggccca ggtcgccgag 240
tcgtgcggca tcctgttcgt caccggcagc tactccgccg cgctgaagaa cccgaccgac 300
gactcgttct cggtcaagag cagccacccg aatctgctgc tgggcacgaa catcggcctc 360
gacaagcccg tcgaactggg cctgcagacc gtggaagaaa tgaaccccgt gctgctccag 420
gtgcatgtga acgtgatgca agagctgctg atgccggagg gcgaacgcaa gttccgcagc 480
tggcagtcgc acctggccga ctactcgaag cagatccccg tgccgatcgt gctgaaagaa 540
gtgggcttcg gcatggacgc caagaccatc gagcgtgcct acgagttcgg cgtgcgcacc 600
gtggacctct cgggccgcgg tggcacgagc ttcgcgtaca tcgaaaaccg gcgcagcggc 660
cagcgcgact acctgaacca gtggggccaa tcgaccatgc aggccctgct gaacgcgcaa 720
gaatggaagg acaaggtcga gctgctggtg tcgggcggcg tgcgtaaccc gctcgacatg 780
atcaagtgcc tggtgttcgg cgccaaggcc gtgggcctgt cccgcaccgt gctggagctg 840
gtcgaaacct acaccgtcga agaagtcatc ggcattgtcc agggctggaa ggccgacctc 900
cgcctcatca tgtgctccct gaactgcgcc acgatcgcgg acctccagaa ggtggactat 960
ctcctctacg gcaagctcaa agaagccaag gaccagatga agaaggcgtg a 1011

<210> SEQ ID NO 29
<211> LENGTH: 1683
<212> TYPE: DNA
<213> ORGANISM: Populus alba

<400> SEQUENCE: 29
atgcggtgct ccgtcagcac cgagaacgtg tcgttcaccg aaaccgaaac ggaagcccgc 60
cgctcggcga actacgagcc gaacagctgg gactacgact atctgctgtc gagcgatacc 120
gacgagagca tcgaagtgta caaggataag gccaagaagc tggaagccga ggtgcgccgc 180
gagatcaata acgaaaaggc cgagttcctg accctgctgg aactgattga caacgtgcaa 240
cgcctgggcc tgggctaccg cttcgaaagc gatatccggg gcgccctgga ccgtttcgtg 300
agctccggcg gtttcgacgc ggtgaccaag acctccctgc acggcaccgc gctgtcgttc 360
cgtctgctgc ggcagcacgg cttcgaggtg tcgcaagaag ccttcagcgg cttcaaggac 420
cagaacggca acttcctgga gaacctcaag gaggacatca aggccatcct gagcctgtac 480
gaagcctcct tcctggccct ggaaggcgag aacatcctgg acgaagccaa ggtctttgcc 540
atttcgcacc tgaaggaact gtcggaagag aagatcggca aggaactcgc cgaacaggtc 600
aaccatgcgc tggagctccc gctgcaccgc cggacgcagc gcctggaagc cgtgtggagc 660
atcgaggcgt accgcaagaa ggaagatgcg aaccaagtgc tgctggagct ggccatcctg 720

-continued

```
gactataaca tgatccagag cgtctaccag cgtgatctgc gcgaaacgtc ccgttggtgg    780
cgccgcgtcg gtctggccac gaagctgcac ttcgcccgcg accgcctgat cgagtcgttc    840
tactgggccg tcggcgtcgc gtttgagccg cagtactcgg actgccgcaa cagcgtcgcc    900
aagatgttct cgttcgtgac catcatcgac gacatctacg acgtgtacgg cacgctggac    960
gaactggagc tgttcacgga cgccgtggag cgctgggacg tgaacgcgat caatgatctg   1020
ccggactaca tgaagctctg cttcctcgcc ctgtacaata ccatcaacga aatcgcctat   1080
gacaatctga aggacaaggg cgagaatatc ctgccctacc tgaccaaggc ctgggcggat   1140
ctctgcaacg cgtttctgca agaagcgaag tggctgtaca acaagtccac cccgacgttc   1200
gacgactatt tcggcaacgc gtggaagtcg agctcgggtc cgctgcagct ggtgttcgcg   1260
tacttcgcgg tcgtccagaa catcaagaaa gaagagatcg agaacctcca gaagtatcat   1320
gacaccatct cccgcccgag ccacattttc cgcctctgca acgacctggc cagcgcgtcg   1380
gcggagatcg cccgcggcga aaccgcgaac tcggtgtcct gctacatgcg caccaagggc   1440
atcagcgagg aactggccac ggagtcggtg atgaacctga ttgacgaaac ctggaagaag   1500
atgaacaagg aaaagctggg cggcagcctc tttgccaagc ccttcgtgga aacggcgatc   1560
aatctcgccc ggcagtcgca ttgcacctac cacaacggcg acgcgcacac cagccccgat   1620
gagctgaccc gcaagcgcgt cctgtcggtc atcacggagc cgatcctgcc cttcgagcgc   1680
tga                                                                 1683
```

<210> SEQ ID NO 30
<211> LENGTH: 1683
<212> TYPE: DNA
<213> ORGANISM: Salix sp.

<400> SEQUENCE: 30

```
atgcgctgct ccgtcagcac cgagaacgtg agctttacgg aaaccgaaac ggaaacgcgc     60
cgcagcgcca attacgagcc gaactcctgg gactacgact acctcctgtc ctccgacacc    120
gacgagtcga tcgaagtcta caaggacaag gccaagaagc tggaagcgga agtgcgccgg    180
gagatcaaca acgaaaaggc cgagttcctg accctgctgg agctcatcga caatgtgcag    240
cgcctgggcc tgggttaccg tttcgagagc gacatccgtc gcgccctgga tcgcttcgtg    300
tcgtcgggcg gcttcgatgc cgtcaccaag accagcctgc acgccacggc cctgtcgttc    360
cggttcctgc gtcagcacgg cttcgaggtg agccaagaag ccttcggcgg cttcaaggac    420
cagaacggca acttcctgga gaacctgaag gaagatatca aggccatcct ctccctgtac    480
gaagcctcct tcctcgccct ggaaggcgag aacatcctgg atgaagcgaa ggtgttcgcc    540
atctcgcatc tgaaggaact gagcgaggaa aagatcggca aggacctggc cgaacaggtg    600
aatcacgccc tggagctccc gctgcatcgc cgcacccagc gcctggaagc ggtctggtcc    660
atcgaagcct atcgcaagaa ggaggacgcc aaccaagtgc tgctggaact ggcgatcctg    720
gactacaaca tgatccagtc ggtgtaccag cgcgacctcc gcgaaacgtc ccggtggtgg    780
cggcgcgtgg gcctggcgac caagctgcac ttcgcgcgcg accgcctgat tgagtcgttc    840
tactgggcgg tgggcgtcgc cttcgagccg cagtattcgg actgccgcaa cagcgtggcg    900
aagatgttca gcttcgtcac catcattgac gatatctacg acgtctatgg caccctggat    960
gagctggagc tgttcacgga cgccgtggag cggtgggacg tgaacgcgat caacgacctc   1020
cccgactaca tgaagctgtg cttcctggcc ctgtacaaca ccatcaacga aatcgcctat   1080
gataacctca aggaaaaggg cgaaaacatc ctgccgtacc tgaccaaggc gtgggcggat   1140
```

-continued

```
ctgtgcaacg cgttcctcca agaagcgaag tggctgtata acaagagcac gcccaccttc   1200

gacgactatt ttggcaacgc gtggaagtcg tcgtcgggtc ccctccagct cgtgttcgcg   1260

tactttgccg tcgtccagaa tatcaagaaa gaagagatcg agaatctgca gaagtatcac   1320

gacatcatca gccgtccgtc gcacatcttc cgcctgtgca acgacctggc ctcggcctcc   1380

gcggagattg cgcggggtga aaccgccaac tcggtgtcgt gctacatgcg cacgaagggc   1440

atcagcgagg aactcgccac cgagtcggtc atgaacctga tcgacgaaac gtggaagaag   1500

atgaacaagg aaaagctggg cggcagcctg ttcccgaagc cgtttgtgga aacggcgatc   1560

aatctggccc gccagagcca ctgcacctac cacaacggcg acgcgcatac ctcgccggac   1620

gagctgaccc gcaagcgcgt cctgtcggtg atcacggagc cgatcctgcc cttcgagcgc   1680

tga                                                                 1683
```

```
<210> SEQ ID NO 31
<211> LENGTH: 1191
<212> TYPE: DNA
<213> ORGANISM: Homo sapien

<400> SEQUENCE: 31

atgctgtcgg aggtgctgct ggtgagcgcc ccgggcaagg tgattctgca cggcgaacat     60

gcagtggtgc atggcaaggt ggccctggcc gtgagcttga acctgcgcac cttcctgcgc    120

ctgcagccgc atagcaacgg caaggtggat ctgtcgctgc cgaatatcgg cattaagcgc    180

gcctgggacg tggcccgcct gcagtcgctg gacacctcgt ttctggaaca gggcgacgtg    240

accaccccga cctcggaaca agtggaaaag ttgaaggaag tggccggcct gccggacgac    300

tgcgccgtga ccgaacgcct ggccgtgttg gcctttctgt atctgtatct gagcatttgc    360

cgcaagcagc gtgccctgcc gtcactggat attgtggtgt ggtcggaact gccgccaggc    420

gccggcctgg gttcgtcggc cgcatattca gtttgcctgg cagcagccct gctgaccgtg    480

tgcgaagaaa tcccgaaccc gctgaaggac ggcgactgcg tgaaccgctg gaccaaggag    540

gacctggagc tgatcaacaa gtgggccttc cagggcgagc gcatgatcca tggcaacccg    600

tcaggcgttg acaatgccgt gtcgacctgg ggcggcgccc tgcgctatca tcagggcaag    660

atcagctcgt tgaagcgttc gccggccctg cagatcctgc tgaccaacac caaggtgccg    720

cgtaacaccc gcgccttggt ggccggcgtg cgtaatcgcc tgctgaagtt tccggaaatc    780

gtggccccgc tgctgacctc gatcgacgcc atcagcctgg aatgcgaacg cgtgctgggt    840

gaaatgggcg aagccccggc cccggaacag tacctggttc tggaggagct gatcgacatg    900

aaccagcacc acctgaacgc cttgggtgtg ggccacgcaa gcctggacca gctgtgtcag    960

gtgactcgcg ccagaggctt gcattcgaag ctgaccggcg caggcggtgg tggttgtggt   1020

atcaccttgc tgaagccggg cctggaacag ccggaagtgg aagccactaa gcaggccctg   1080

acctcgtgcg gcttcgattg cttggaaacc agcatcggcg caccgggcgt ttcgatccat   1140

tcggccacct cgctggattc gcgcgtgcag caggccctgg acggcctgtg a            1191
```

```
<210> SEQ ID NO 32
<211> LENGTH: 906
<212> TYPE: DNA
<213> ORGANISM: Methanosarcina mazei

<400> SEQUENCE: 32

atggtgtcgt gctcggcccc gggcaagatt tacttgttcg gcgaacatgc cgtggtgtac     60
```

-continued

```
ggcgaaaccg ccatcgcctg cgccgtggaa ctgcgtaccc gcgtgcgtgc cgagctgaat    120

gattcgatca ccatccagtc gcaaatcggc cgcaccggcc tggacttcga gaagcacccg    180

tacgtgtcgg ccgtgatcga gaagatgcgc aagtcgatcc cgatcaacgg cgtgttcctg    240

accgtggatt cggacatccc ggtgggttcg ggcctgggct cgtcagccgc agtgaccatt    300

gcctcaatcg gcgccctgaa cgagctgttc ggcttcggtc tgtcgctgca ggagatcgcc    360

aagctgggcc acgagatcga aatcaaggtg cagggcgcgg caagcccgac cgacacctat    420

gtgtcaacct tcggcggcgt ggtgaccatc ccagaacgcc gcaagctgaa aaccccggat    480

tgcggcatcg tgatcggcga caccggcgtg ttcagcagca ccaaggagtt ggtggccaac    540

gtgcgccagt tgcgcgagtc gtacccggac ctgatcgagc cgctgatgac ctcgatcggc    600

aagatcagcc gcatcggcga gcagctggtg ttgtcgggcg actatgccag catcggccgt    660

ctgatgaacg tgaaccaggg cctgctggac gccctgggcg tgaacatcct ggaactgtcg    720

cagctgattt attcggcccg cgcggccggc gcattcggcg caaaaattac cggtgccggc    780

ggtggtggct gtatggttgc cttgaccgcc ccagagaagt gtaatcaggt ggcagaagcc    840

atcgcgggcg ccggcggcaa ggtgaccatc accaagccga ccgagcaggg cctgaaggtg    900

gactga                                                               906
```

<210> SEQ ID NO 33
<211> LENGTH: 1332
<212> TYPE: DNA
<213> ORGANISM: Saccharomyces cerevisiae

<400> SEQUENCE: 33

```
atgtcgctgc cgttcttgac cagcgccccg ggcaaggtga tcatctttgg cgagcactcg     60

gccgtttaca acaagccagc cgtggccgca tcagtgtcgg ccctgcgcac ttacctgctg    120

atctcggaat cgtcggcccc ggacaccatc gagctggact ttccggacat cagcttcaac    180

cacaagtggt cgatcaacga cttcaacgcc atcaccgagg accaggtgaa ctcacagaag    240

ctggccaagg cccagcaggc caccgacggc ctgtcacagg aactggtgag cctgctggac    300

ccactgttgg cccagctgag cgagtcgttc cattaccatg ccgccttctg cttcctgtat    360

atgttcgtgt gcctgtgccc gcacgccaag aacatcaagt tctcgctgaa gtcgactctg    420

ccaatcggcg ccggtctggg tagctcggcc tcaatctcag tgagcttggc cctggccatg    480

gcctacttgg gcggcctgat cggcagcaac gatctggaga agctgtcgga gaacgacaag    540

cacatcgtga accagtgggc cttcatcggc gagaagtgca tccacggcac cccgtcgggc    600

atcgacaacg ccgtggccac ctatggcaac gccctgctgt tcgaaaagga ctcgcacaac    660

ggcaccatca acaccaacaa cttcaagttc ctggacgatt tcccggccat cccgatgatc    720

ctgacctaca cccgcatccc gcgcagcacc aaggatcttg tggcccgcgt gcgcgtgctg    780

gtgaccgaaa agttcccgga agtgatgaag ccgatcctgg atgccatggg cgagtgcgcg    840

ctgcagggcc tggagatcat gaccaagctg tcgaagtgca agggcaccga cgacgaggcc    900

gtggaaacca acaacgagct gtacgagcag ctgctggagc tgatccgcat caaccacggc    960

ctgctggtgt cgatcggcgt gtcgcatccg ggcctggaac tgatcaagaa tctgtcggac   1020

gatctgcgta tcggctcgac caagctgacc ggcgcaggag gtggcggctg ctcgctgacc   1080

ctgctgcgcc gcgatattac tcaggagcag atcgactcgt tcaagaagaa gctgcaggac   1140

gacttctcgt acgaaacctt cgagactgac ctgggcggca ccggctgctg cctgctgtcg   1200

gccaagaacc tgaacaagga cctgaagatc aagtcgctgg tgttccagct gttcgagaac   1260
```

aagaccacca ccaagcagca gatcgacgac ctgctgctgc cgggcaacac caacctgccg 1320
tggacctcgt ga 1332

<210> SEQ ID NO 34
<211> LENGTH: 1356
<212> TYPE: DNA
<213> ORGANISM: Saccharomyces cerevisiae

<400> SEQUENCE: 34
atgtcggaac tgcgcgcctt ctcggccccg ggtaaagcct tgctggccgg tggctacctg 60
gttctggaca ccaagtatga agccttcgtg gtgggcttgt cggcccgcat gcatgccgtg 120
gcccatccgt acggctcact gcagggctcg gacaagtttg aggtgcgcgt gaagtcgaag 180
cagttcaagg acggcgagtg gctgtaccac atctcgccga agtcgggctt catcccggtg 240
tcgatcggcg gcagcaagaa cccgttcatc gagaaggtga tcgccaacgt gttctcgtac 300
ttcaagccga acatggacga ctactgcaac cgcaacctgt tcgtgatcga catcttctcg 360
gacgacgcct accactcgca ggaggacagc gtgaccgagc accgcggcaa tcgccgcctg 420
tcgttccaca gccatagaat cgaagaggtt ccaaagaccg gcctgggctc gtcggcaggc 480
ctggttaccg tgctgaccac cgccctggcc tcgtttttcg tgtcggacct ggagaacaac 540
gtggacaagt accgcgaggt gattcacaac ctggcccaag ttgcccattg ccaggcccag 600
ggtaagatcg gctcgggttt cgacgtggcc gccgccgcct atggttcaat cagataccgc 660
cgctttccgc cggccctgat ctcgaatttg ccggacattg gctcggccac ctacggctcg 720
aagctggccc atctggtgga cgaggaggac tggaacatca ccatcaagtc gaaccacctc 780
ccgtcgggcc tgaccctgtg gatgggcgac atcaagaacg gctcggaaac cgtgaagctg 840
gtgcagaagg tgaagaactg gtacgactcg cacatgccgg agagcctgaa aatctacacc 900
gagctggacc acgccaactc gcgcttcatg gacggcctga gcaagctgga ccgcctgcac 960
gaaacccacg acgactacag cgaccaaatc ttcgagtcgc tggagcgcaa cgactgcacg 1020
tgccagaagt acccggagat caccgaagtg cgcgacgccg tggccaccat ccgtcgctcg 1080
tttcgcaaga tcaccaagga atcgggcgcc gatatcgaac cgccggtgca gacttcgctg 1140
ctggatgact gccagacctt gaagggtgtg ttgacctgcc tgatcccagg cgccggcggc 1200
tatgatgcca tcgccgtgat caccaagcag gacgtggatc tgcgcgccca gaccgccaac 1260
gataagcgct tctcgaaggt gcagtggctg gacgttaccc aggcagactg gggcgtgcgc 1320
aaggagaagg acccggaaac ctacctggac aagtga 1356

<210> SEQ ID NO 35
<211> LENGTH: 1191
<212> TYPE: DNA
<213> ORGANISM: Saccharomyces cerevisiae

<400> SEQUENCE: 35
atgaccgtgt acaccgccag cgtgaccgcc ccggtgaaca tcgccaccct gaagtactgg 60
ggcaagcgcg ataccaagct gaatctgccg accaactcgt cgatctcggt gaccctgtca 120
caggacgatc tgcgcaccct gacctcggca gccaccgccc cggagttcga acgtgatacc 180
ctgtggttga acggcgaacc gcactcgatt gacaacgagc gcacccagaa ctgcctgcgc 240
gacctgcgcc agttgcgcaa ggaaatggag agcaaggacg cctcgctgcc gaccctgagc 300
cagtggaagc tgcatatcgt gtcggagaac aattttccga ccgccgcagg cctggcctca 360

-continued

```
tcggcagcag gcttcgccgc cctggtttcg gccatcgcca agctgtatca gttgccgcag    420

tcgacctcgg aaatttcgag gatcgcccgt aagggctcag gtagcgcctg ccgctcgctg    480

tttggcggct atgtggcatg ggaaatgggc aaggcagagg acggccacga ctcgatggca    540

gtgcagatcg ccgactcgtc ggactggccg cagatgaagg cctgcgtgtt ggtggtgtcg    600

gacatcaaga aggacgtgtc gtcgacccag ggcatgcagc tgaccgtggc cacctcggag    660

ctgttcaagg agcgcattga gcacgtggtg ccgaagcgct tcgaggtgat gcgcaaggcc    720

atcgtggaga aggacttcgc caccttcgcc aaggagacta tgatggactc gaactcgttc    780

cacgccacgt gcctggacag cttcccgccg atcttctaca tgaacgacac cagcaagcgc    840

atcatcagct ggtgccacac catcaaccag ttctacggcg aaaccatcgt ggcctacacc    900

ttcgacgccg gcccgaacgc cgtgctgtac tacctggccg agaacgagtc gaagctgttc    960

gccttcatct acaagctgtt cggctcggtg ccgggctggg acaagaagtt caccaccgag   1020

cagctggagg ccttcaacca ccagttcgaa tcgtcgaact tcaccgcccg cgagctggac   1080

ctggaactgc agaaggatgt ggcccgcgtg attctgaccc aggtgggctc gggcccgcag   1140

gaaaccaacg aatcgctgat cgacgccaag accggcctgc cgaaggagtg a            1191
```

<210> SEQ ID NO 36
<211> LENGTH: 933
<212> TYPE: DNA
<213> ORGANISM: Lactococcus lactis

<400> SEQUENCE: 36

```
atgaccatca acaagatggg caccggcatc gcccactcga agctgatcct gatcggcgaa     60

cactcggtgg tgtacggcca gccggccatc gccctgccgg tgaccatcct gaaaaccacc    120

gtgaccatca cctcgtcgaa gtacggccag tacatcgaga acaacgagtt ccgccgccgc    180

ctggacctga tgggcgacga gttcgagggc atccgccagc tgatcatgcg cctgctgtcg    240

aagttccaca gcagcaagat gccgttctcg ctggagatcg actcgaatat cccacaaggc    300

cgcggtctgg gcgcctcggc ctcgctggcc accgccatta tccgcgcctt ctatgatttc    360

ttcgacgccg aactgccgca gaaggacctg ctgttctacg ccaacttctc ggagaacatc    420

acccacggca agtcgtcggg catcgacgtg gccaccgtga actcggagca cccgctgtgg    480

ttcatcaagg actcgaccat cgagccgttc gagctgaacc tgcacggctt catcgtgatc    540

ggcgacaccg gcgtgcatgg cttcacctcg caggccatca acatcgtgcg cgagaagctg    600

gtggaggaga aggaaaagac ccaggacagc atcaaccacc tgggccagct ggccaccgac    660

agcaaggact tcctgatgac cgacaagctg aaggagttcg gccacgtgat gaacaaggcc    720

cacgagcgcc tgtcggacct gggcgtgtcg catccgcgct tggataacct ggtggaaacc    780

gcccgcaaga atggcgcctt gggcgccaaa ttgactggct caggcctggg cggcgtgatg    840

gtggccctgg cagaaaacga aaaggacgcc atccgcatct cgcagcgcct gctgaagaac    900

ggcgccaaga acacctggat ctactcgttc tga                                 933
```

<210> SEQ ID NO 37
<211> LENGTH: 990
<212> TYPE: DNA
<213> ORGANISM: Lactococcus lactis

<400> SEQUENCE: 37

```
atgaacatct cggagaagaa gatgagcatc aaggtgccgg gcaagctgtt cttcgccggc     60

gagtacagcg tgaccaagga gggcaacctg gccctgatca ccaccatcga aaccaacttc    120
```

gaggtgcgca tctcggccac caccggcaag agcatcttca agaccaacgt gggcctgagc 180
gacttcgagt tctcgctgtc gaagatcgag ttcaccaagg agaacccgtg gaacttcgcg 240
ctgaccgccc tgaagaacac cctgtcggcc gccgactcgt tcgagaagaa gtcggtgagc 300
aagatcctgt cgtcgtcgcc ggaaatcagc ctggagatcg tgtcggactt gggcttcggc 360
gagaacaaga agggctacgg ctcgtcggcc tcggtggtgt gcggcctggt gaacgccgtg 420
aaccagttct tcgacttcca gctgtcgctg gagaagcgct tcgagatcgc ggccaagacc 480
cacttcgaag tgcagggctc gggctcgatg ggcgatatcg ccgccatcat gtacggcggc 540
tcggtgttct accagaacca taagcgcgtg atcccgctgg aaatcccgtg ggccacctac 600
gtggtgcaga ccggcaaggc cgccaagacc agcgagaaga tcaagatcaa gctgtcggac 660
gagttctacc aggccagcaa cgagctggtg atcgagctgg ccaccgccat cgacatccag 720
gacttcgccc tgttcaagga gaagctgtcg gagaaccagc tgctgctgct ggagaacatc 780
ccggagggct acatgaccaa ggagctggcc atcgccctga acctgctgaa ctcgtacccg 840
gagttcgccg ccaagatcag tggcgccggc ttcggcgaaa acatcatcct gttcgcccag 900
aacacccagg ccatcgccga ggtgcagaac aagctgagcg agtacggcat caacctggag 960
aagttcaagg tggcccagaa gaacaactga 990

<210> SEQ ID NO 38
<211> LENGTH: 957
<212> TYPE: DNA
<213> ORGANISM: Lactococcus lactis

<400> SEQUENCE: 38
atgaagaaca tcgtgaccgc ccgcgcccac accaacatcg ccctgatcaa gtactggggc 60
aaggccgaca tcgccctgaa catcccgacc acctcgtcgc tgagcatgac cctggagccg 120
ttctacacca ccaccagcgt ggagttcacc gacaacgagt cggactcgct gatcctgaac 180
tcggaggtgg ccgacagctc gcgcgtgtcg cagttcctgg agatgatgcg cggccagtac 240
ggcaacttcc cgaaggtgat gatccagtcg gaaaaccacg tgccgaccgc cgccggtctg 300
gcctcgtcag catcgtcgtt cgcagccctg actgccgcaa tgttcggcct gctggacctg 360
gaaaaggacg attcggaaat gtcgcgcatc gcccgccgcg gttcgggctc ggcatcgcgt 420
tcgatcttcg gcaacttctc ggtgtggaac aagggcgagg accatcagag ctcgttcgcc 480
gagagcttct acaacgagga catcggcctg tcgatgatcg tggccgagat cagcgccgag 540
aagaagaaga tgtcgtcgac caagggcatg cagctggccc agaccgcccc gacctacagc 600
gcctgggtgg agaagtcggc catccagctg gaggagatga agcaggcaat cctgaacgcc 660
gacatcgaga aggtgggcct ggtggcccag gacaacgccc tgggcatgca cgagcagaac 720
cgcctgagca accagccgtt cgactacttc acccacgaaa cccgccacgt gatcgacttc 780
gtgaaccagg cctaccagtc gggcctgctg gccttcgtga ccatcgacgc cggcccgaac 840
gtgaagatca tcaccgacca tgccaccgaa aaggtgctgc tggccaagct gcaggccgag 900
ttcccggaac tgacctttga catcgcgcgc gccggcggcg cctacgagta cctgtga 957

<210> SEQ ID NO 39
<211> LENGTH: 969
<212> TYPE: DNA
<213> ORGANISM: Listeria monocytogenes

<400> SEQUENCE: 39

-continued atggccaccg gcatcggcac cgccaagatg atcttgtgcg gcgaacacgc cgtggtgtac 60
ggcgaaccgg ccatctcggt gccgttcact caagccgtgg tgaccaccaa cgtggaaacc 120
agcatcaaga ccaagttctc gtcggccttc ttctcgggcg acctggacga catgccggac 180
ttcctggccg gcatcaaggc cctggtggtg gacgtgctga acgagatcgg taatggcgaa 240
tgcgtgtcga ttcatgtggt gagcggcgtg ccaatcggcc gcggcctggg ttcaagcgcc 300
gccgtggcca cttcaatcgc ccgcggtctg tacaagtact tcaaccagga gctggactcg 360
aagaagctgc tggccatcgt gaacgcagcc gaaaagatcg cccacggcaa cgcctcgggc 420
gtggacgcca tcaccgtggt gtcggaaaag ccggtgtggt atgagcgcga ccgcaagctg 480
gagatcatgc acttcccgaa gaagatcacc ttcgtggtgg ccgacaccgg cgtgccgtcg 540
gaaacccgcg acgccgtgaa ggacgtgcag gtcctgtaca aggagaacca ggtggagatc 600
ggcaagatca tccaccagct gggcgacatc agccgcgaga tcaagaccca cctggagggc 660
gacgcggaca ccgtgaagat cggcgcggcc atgaacaagg cccagtcgta cctggaaacc 720
ctgaccgtga gcgactcgtc gttggagaag ctgattaagg ttgcccgctc aaacggcgcc 780
gatggcgcaa agctgactgg cggcggtcgc ggcggctgca ttatcgccgt ggccaagaac 840
caagaaatcg ccgaacagat caccaaggcc ctgcataacg ccggcgccgc ccaggaatgg 900
atcttcacca tcggcgaggg cagctacgag tcggactcgc accgcaccca tgaatgtggc 960
gccaactga 969

<210> SEQ ID NO 40
<211> LENGTH: 1080
<212> TYPE: DNA
<213> ORGANISM: Listeria monocytogenes

<400> SEQUENCE: 40
atgtaccaga tgaagaacaa gctgcaagtg aagatcccgg gcaagctgta cgtggccggc 60
gaatacgccg tggtggaatc gggccatacc gccatcctga ccgccgtgaa ccgctacatc 120
accctgaccc tggaagattc ggagcgcaac gagctgtgga ttccgcacta cgagaacccg 180
gtgtcgtggc cggtgggcgg cgaattgaag ccggacggcg aacattggac cttcaccgcc 240
gaggccatca acatcgccac caccttcctg aagtcggagg gcatcgaact gaccccggtg 300
aagatgatca tcgagactga gctgatcgac cagtcgggcg caaagtacgg cctgggctcg 360
tcggcagccg ccaccgtggc cgtgatcaac gccctgatga ccaagttcta cccggagatc 420
agcatgctga agaagttcaa gctggccgcc ctgtcgcatc tggtggtgca gggcaacggc 480
tcgtgcggcg acatcgcctc gtgcatgtat ggcggctgga tcgcctatac caccttcgat 540
caggagtggg tgaagcaccg cctggcctac aagtcgctgg agtggttcat gaaggagccg 600
tggccgatgc tgcagatcga aaccctggag gaaccggtgc cgaccttctc ggtgggttgg 660
accggcaccc cagtgtcgac tggtaagctg gtgtcgcaga tccacgcctt caagcaggag 720
gactcgaaga actaccagca cttcctgacc cgcaacaacg agatcatgaa gcagatcatc 780
caggccttcc acaccaagga cgaggagctg ctgtactcgg ccatcaagga gaaccgccgc 840
attctgcagg agctgggcac caaggccggt gtgaacatcg aaacctcgct gctgaaggaa 900
ctggcggata gcgccgaaaa catgggcggc gcaggcaagt cgtcgggttc gggcggcggt 960
gactgcggta tcgcattcag caagaccaag gaactggccg agaagctggt gaacgagtgg 1020
gagaagctgg gcatcaagca cctcccgttc cacaccggcc gcgtgcagat caccgagtga 1080

-continued

<210> SEQ ID NO 41
<211> LENGTH: 972
<212> TYPE: DNA
<213> ORGANISM: Listeria monocytogenes

<400> SEQUENCE: 41
atgaaggcca ccgccatcgc ccacaccaac gtggccctga tcaagtactg ggcaagcgc 60 gacgagcacc tgatcctgcc ggccaactcg tcgctgtcgt tcaccgtgga caagttctac 120
accaagacca ccgtggagtg ggacgagaag ctgacccagg acaccttcat cctgaacaac 180
gagcaaaaga ccgacgccaa ggtggcccgc ttcatcgaca agatgcgcga ggagttcggc 240
atcagcgcca aggcgaagat cacctcggaa aatcatgtgc caaccgccgc cggcctggcc 300
tcatcggcat cggcattcgc agcattggcc ttggccggct cgaatgcagc cggccgcaag 360
gacaccaagg aatatatctc gcgtctggcc cgcttcggct caggctcggc aagccgcagc 420
gtgtttggcg acttcgtgat ttgggaaaag ggcgagctgg ccgatggctc ggactcgttc 480
gccgtgccgt tcaccaacaa gctgtgcgac aagatgtcgc tggtggtggc cgtggtgagc 540
gacaaggaga agaaggtgag cagccgcgac ggcatgcgcc tgaccgtgga aacctcgccg 600
ttcttcgaga actgggtgtc ggccgccgag atcgacctgg aggagatgaa gcaggccatc 660
ctggacgagg acttcatcaa ggtgggcgag atcaccgagc gcaacggcat gaagatgcac 720
gccaccaccc tgggcgccga accgccgttt acctacttcc agccgcagtc gctggaaatc 780
atggacgccg tgcgcgagct gcgcgaaaat ggcatcccgg cctacttcac catggacgcc 840
ggcccgaacg tgaaggtgat ctgcgagcgc gccaacgaga acatcgtggc cgagaagctg 900
tcgggcctgg ccaagaacgt gctgatctgc cacgccggca aggaagcctc ggtggtgtcg 960
gacgagaagt ga 972

<210> SEQ ID NO 42
<211> LENGTH: 945
<212> TYPE: DNA
<213> ORGANISM: Enterococcus faecalis

<400> SEQUENCE: 42
atgaatatca agaagcaagg tctgggccag gcgaccggca agatcatcct gatgggcgag 60
cacgccgtgg tgtacggcga gccggccatc gcgttcccgt tccaagcgac ggaaatcacc 120
gccgtgttca ccctcgccaa gacgatgcag atcgactgcg cctacttcac gggcctgctg 180
gaagatgtgc cgcaggaact ggccaacatc aaggaagtcg tccagcaaac cctgcacttc 240
ctcaaggagg acacgttcaa gggcaccctg accctgacga gcaccatccc cgccgagcgc 300
ggcatgggct cctcggccgc gacggccgtg gcgatcgtcc gctccctgtt cgactacttc 360
gactatgcgt acacctacca ggaactgttc gaactggtgt ccctgtccga gaagatcgcg 420
cacggcaacc cctcgggcat cgacgccgcc gccacctcgg gcgccgaccc cctcttcttc 480
acgcgcggct tcccgcccac ccatttcagc atgaacctgt cgaacgcgta cctggtggtg 540
gccgacaccg gcatcaaggg ccagacccgc gaagcggtca aggacatcgc ccagctggcg 600
cagaacaacc cgacggcgat tgccgaaacg atgaagcaac tgggcagctt caccaaggaa 660
gccaagcaag ccatcctcca agatgacaag cagaagctgg gccagctgat gaccctggcc 720
caagagcagc tgcagcagct gagcgtgagc aacgatatgc tggatcgcct ggtggcgctg 780
tcgctggagc acggcgccct gggcgcgaag ctcaccggcg gtggtcgggg cggttgcatg 840
atcgcgctga ccgacaacaa aaagacggcg cagacgatcg cgcagaccct ggaagagaac 900

-continued ggcgccgtgg ccacgtggat tcagtcgctg gaagtgaaga agtga 945

<210> SEQ ID NO 43
<211> LENGTH: 1107
<212> TYPE: DNA
<213> ORGANISM: Enterococcus faecalis

<400> SEQUENCE: 43
atgatcgaag tgaccacccc cggcaagctg tttatcgccg gcgagtacgc cgtggtcgag 60
ccgggccacc cggcgatcat cgtggccgtg gaccaattcg tgaccgtgac ggtcgaagaa 120
accaccgatg aaggctccat ccagtcggcc cagtattcct cgctgccgat ccgctggacc 180
cgtcgcaacg gtgagctggt gctggatatc cgggagaatc ccttccacta cgtgctggcg 240
gccatccatc tgaccgaaaa gtatgcccag gaacagaaca aggaactgtc gttctaccac 300
ctgaaggtca cctcggagct cgactcgtcc aacggccgta agtatggcct gggctcgtcg 360
ggcgccgtga cggtgggtac cgtgaaggcc ctcaacatct tctacgacct gggcctggag 420
aacgaagaga ttttcaagct gtccgccctg gcccatctgg cggtccaggg caacggctcg 480
tgcggtgaca tcgccgcctc gtgctacggc ggctggatcg ccttttccac cttcgaccac 540
gactgggtga atcaaaaggt cgccaccgaa accctgacgg atctgctggc catggactgg 600
ccggagctga tgatcttccc cctgaaggtc ccgaagcaac tgcgcctgct gatcggctgg 660
acgggcagcc ccgcgagcac gagcgacctc gtcgatcgcg tccaccagag caaggaagag 720
aagcaagccg cctacgagca gttcctcatg aagtcgcggc tgtgcgtgga aaccatgatc 780
aacggcttca atacgggcaa gatcagcgtg atccagaagc aaatcaccaa gaaccgccag 840
ctgctggcgg agctgtccag cctgacgggc gtggtgatcg aaacggaagc cctgaagaac 900
ctgtgcgacc tggccgagtc ctacaccggc gccgccaagt cctcgggcgc gggcggcggc 960
gactgcggca tcgtgatctt ccgccagaag tcgggcatcc tccccctgat gacggcgtgg 1020
gaaaaggacg gtatcacgcc gctgcccctg cacgtctaca cgtatggtca aaaggaatgc 1080
aaggaaaagc acgagagcaa gcggtga 1107

<210> SEQ ID NO 44
<211> LENGTH: 996
<212> TYPE: DNA
<213> ORGANISM: Enterococcus faecalis

<400> SEQUENCE: 44
atgctctccg gcaaggcgcg ggcccatacc aacattgcgc tgatcaagta ttggggcaag 60
gccaatgaag agtacatcct gccgatgaac tccagcctga gcctgaccct ggacgcgttc 120
tatacggaaa cgaccgtcat cttcgacgcc cattactcgg aagatgtgtt catcctcgat 180
ggcatcctgc agaatgagaa gcagacgaag aaggtgaagg aatttctgaa tctggtgcgg 240
cagcaggccg actgcacctg gttcgcgaag gtcgagtcgc agaacttcgt gccgacggcg 300
gcgggcctgg cctccagcgc gagcggcctg gccgcgctgg cgggcgcgtg caacgtggcg 360
ctgggcctga acctgagcgc gaaggacctg tcccgcctcg cgcgccgcgg ctcgggctcg 420
gcgtgccgca gcatcttcgg cggtttcgcc cagtggaata agggccactc ggatgaaacc 480
tccttcgcgg aaaacatccc cgccaacaac tgggagaacg aactcgcgat gctgttcatc 540
ctgatcaacg acggcgagaa ggacgtgtcg agccgcgatg gcatgaagcg caccgtcgaa 600
accagctcgt tctaccaggg ctggctggac aacgtggaaa aggacctcag ccaggtccat 660
gaagcgatca agaccaagga ctttccgcgc ctgggcgaga tcatcgaggc caatggcctg 720

```
cgcatgcacg gcacgaccct gggcgccgtc ccgccgttta cgtactggtc gccgggctcg    780
ctgcaggcca tggcgctggt gcgccaggcg cgcgccaagg gcatcccgtg ctacttcacc    840
atggacgccg gccccaacgt gaaggtcctg gtcgaaaaga agaacctgga agccctcaag    900
accttcctct cggagcactt tagcaaggaa cagctggtcc cggcgttcgc cggcccgggt    960
attgaactct tcgaaaccaa gggcatggac aagtga                              996
```

<210> SEQ ID NO 45
<211> LENGTH: 12893
<212> TYPE: DNA
<213> ORGANISM: artificial sequence
<220> FEATURE:
<223> OTHER INFORMATION: Synthetic

<400> SEQUENCE: 45

```
acaatcgttc ccgacagcga aagcccagaa agcgaagaaa ggcgcctctt ctacgtcgcc     60
gtcacgcgcg ccagggattg cctgtttatc tcaacggcga agaagaaccc gacctcgcgc    120
ttcgtccttg aggctggcct aagccttact tcctgaggcg cgcattcttt gtgcgttata    180
tggcactttc gtagaattgc tcgcctttta ctttaacaac gacccgtaag taccggggga    240
acagctcgat ctctcgggta caacaggcac aaagttaact tgcgtatacg tctaagggcc    300
gctaaccttc acggcaacgc aaccgcggac gtcatttttg ccgaaaacgg ttgcacgatc    360
caccggcggt tccggtgaac agcttaaagg tttttgaacc gaatggatat caagctagcc    420
caccccagca agacgacgcc tgaggatttg aagcagttgg caaatctctc cgcggtgatg    480
ctgcagaaaa ttcgggatga gatgctggag ccatttcctc ggaaggaagc cccgctgatc    540
ccgtctggcc gcctacaaga attgtgtggc atcgacaaaa cgcggatgaa ccggtccctc    600
aaaaaggggg atctccctca gggccagcaa tcgcgacccg gtgcagtgcg ctatttcagc    660
ctcagcgagg caatgcaatg gattcgagcg gaacttaagc ctgtcccgcg aaggggacca    720
ggtaaagtca ttgcagttgc gaacttcaag ggcggtgtca cgaagaccac tatgtccacc    780
ctcctctgcc agggcttgag tctgcggcga ggtcggaagg tgtgccacgt tgatctggac    840
ccgcagggaa gcgcaaccac gctgtatggc atcaatccac atgccgaggt gtcgtccgaa    900
aacaccatta tgccgctcat cgaggcgtat ttggcgggcg agtccttcga tatgcgaggg    960
cttcctcagg agacttactg gcctaacctg gatttgattc cttcgtctac tgagcttttc   1020
aacgcggagt ttatgcttcc ggctcgggcg acggcagagg aaggccatat tccgttcgag   1080
cgcgtgttaa gtaacggcct cgattcgttg aaagacgaat atgactacat catcctcgac   1140
acggctccta ccctcagcta cctgaccatc aacgcgattt tcgctgccga tggcgtcatc   1200
gtaccggtgg tcccggacac cttggctttc gcgtctatgg tccagttctg gcaactcttc   1260
tcggacctag taacaggcat ggaagagcag agcgagggat ctaaaaagga gttcgacttt   1320
ctcgatgttc tcatgacacg catggagaaa aagaacgctc ctcgcctggt ggcagactgg   1380
attcgcggcg tctatgggtc gcgcgtgctg ccgattgaga tccctgagac ggacctcgcc   1440
cgtaacagca gcattcaatt tcgcacggtc tatgacctct cctctagcga ggcgaacacc   1500
gagacgatgc gacgcattcg ccaaccctgc gatgagtttg tcgactatgt ggacgacaag   1560
gtcagcgcgc tttggcaagg aattgaagaa tgagtttgag agaaaagctt gccgcaaagg   1620
ctgggaacat caaggtcacg gcggaagact tggagaaagc cgctgcgcgc ggtccgcaag   1680
cgccgcgaac tgcgcccggt cagttaatgc acatgcaagg gaaggttgag cgacaggcta   1740
```

-continued acgagatcgc gcaactaaga gcagaacttg agtcggcccg cgtcagcggc ggcgcagtgg 1800
atgtgcctat cgaccaactg catgaggtcc caggccgcag acgcttcatg cctcccgaga 1860
agtatgtcga attgagggaa aacctcaggc acaacaagct cgttcatcct gtgattgtat 1920
gccctcggcc tgcgggaggc ttcgagattg tctccgggca tcaccggaca gacgcgtacc 1980
gcgagcttgg gcgcgatcac atacgctgcg tgctcggcga acttagttca gacgaggctg 2040
acacgggcgc gttctacgcg aaccttatgc agtcagattt aacggatttc gagaagtttc 2100
ggaagttcga cgaactgctg cttcgcagcc cagacaagac tcaagccgca atagctgaac 2160
aggctggtgt acctgtctcg actctctcag agattttgtc gttccggaac ttgcctcccg 2220
aggtcctaag ccttctcgat agccgcccag acctgctcgg gtcgaatgct ggcgccgagt 2280
tggcaagggc gaccaaagac ggtcgcgggg atcgggtcgt cgaagcggtt aagttgttgg 2340
ccgagaagaa gatcgatcaa cagcaggccg tacggatgac taaggccgag caggttaaga 2400
ccaggcctgc cgcatctacc ggcttcaaaa tcaaggcggg aaaggcgact tggtgcgatg 2460
ttcgtatcgc aaagaaagtc atgcgcattg agttccgcag cgaggaagaa gcggaagcgg 2520
cccaatcggc cattcgcgaa catctggaag ggttagctaa agctgcgtcg gaagacgcaa 2580
aaagctaagt gcttgttttt taaggacttc gtactacgaa tcgaggtttt aagccatgtc 2640
tagactgtaa tcctacaaaa acaaaagccc acggcggcaa ccgtgggctt ttgagaactt 2700
caagctgacc agtttcccgg ccgctacaca ccgaagccac tcgacatgga ttcgttagtc 2760
ggagtgtagc ggaacgcgaa cctgagtcaa gcgacttcaa ccatttttta cgaatgggaa 2820
ggtattatga ctttcgcgca acgctccgtt gctggcgagg atgttgctcg cccacaaaaa 2880
caccttaacc agacagacgc tctgattgct ccggcgccca agcgcctcaa acgcaagact 2940
atcgaagcag tcgagcgcgc aactcgaatc gtcgggatcg ggcgtagcgc ccgatcagct 3000
cttgccgccc tcgcccgcac ggcgaataac gatgacccca ccggtaagat ctttaagcac 3060
cgggaaacgc tttgtgccga aaccggaatg tcgccggcta cttggtaccg tgctcaacga 3120
gaactgctcg acttgggcct aattaccgtc gacgttcaag ttcggaagcg atttggccga 3180
ttcgcaggag cctacattta cctgacggaa aaagcgacgg agatgctcgg cttaagctcg 3240
cgaaaagaag aagaaaccac gggtacgggc gaggacgaca cagcgcagct cggcgagccg 3300
gccgttccac caccctcttc tatggcgcaa ccgtctctca aaacgagagt cctgtttaca 3360
gaagatcgtg tcccatactc ctttcaaaaa agacagcagg atcggctccc ccaggacctg 3420
acacgtctgc gcggcctggg tcttgatgta aatttaattt tttggttgat gcgaaaggct 3480
aaagagcaag gccactttct ctcagatgtc gtaagcgcga catgggagag tcttgcgaaa 3540
gcacgcgtgc caaaagcgta tctgcttgcc ctactcaccg cccgcaccga tttcagtgct 3600
gtctgcaaag caaaggcact caaagaagac aaagcccgaa tccaagtgca ggaccgcgat 3660
ttcgtgcgtt cgatactcgc aggggcagcg cggcagtgtt tcgtggacga aaaaggcaac 3720
catttcgaag tcgaaagcga cggaagctca gtgcttgtca ccgaggtcca aagtgcggtc 3780
acttcccgct tggtaggaac ttccctcgcc gaatttgcaa ggcgactaca cgctggtgcg 3840
taccagaaag ctgaggtcta cgctgctccc cagagagcaa gcggccggct cgagaaacgg 3900
ggaaaggagg cggcttcgac gttatcggcg ttgcgagcga tgctgcgcga ccgcaggtca 3960
gccaacgcgg caaacacgac gaacaatgct catgccatgg cctagggtgt gttttgcgct 4020
gcgccagaga ggccgagcgc ggccgtgagg cttggacgct agggcagggc atgaaaaagc 4080
ccgtagcggg ctgctacggg cgtctgacgc ggtggaaagg gggaggggat gttgtctaca 4140

-continued tggctctgct gtagtgagtg ggttgcgctc cggcagcggt cctgatcaat cgtcaccctt 4200
tctcggtcct tcaacgttcc tgacaacgag cctccttttc gccaatccat cgacaatcac 4260
cgcgagtccc tgctcgaacg ctgcgtccgg accggcttcg tcgaaggcgt ctatcgcggc 4320
ccgcaacagc ggcgagagcg gagcctgttc aacggtgccg ccgcgctcgc cggcatcgct 4380
gtcgccggcc tgctcctcaa gcacggcccc aacagtgaag tagctgattg tcatcagcgc 4440
attgacggcg tccccggccg aaaaacccgc ctcgcagagg aagcgaagct gcgcgtcggc 4500
cgtttccatc tgcggtgcgc ccggtcgcgt gccggcatgg atgcgcgcgc catcgcggta 4560
ggcgagcagc gcctgcctga agctgcgggc attcccgatc agaaatgagc gccagtcgtc 4620
gtcggctctc ggcaccgaat gcgtatgatt ctccgccagc atggcttcgg ccagtgcgtc 4680
gagcagcgcc cgcttgttcc tgaagtgcca gtaaagcgcc ggctgctgaa cccccaaccg 4740
ttccgccagt ttgcgtgtcg tcagaccgtc tacgccgacc tcgttcaaca ggtccagggc 4800
ggcacggatc actgtattcg gctgcaactt tgtcatgctt gacactttat cactgataaa 4860
cataatatgt ccaccaactt atcagtgata aagaatccgc gcgttcaatc ggaccagcgg 4920
aggctggtcc ggaggccaga cgtgaaaccc aacatacccc tgatcgtaat tctgagcact 4980
gtcgcgctcg acgctgtcgg catcggcctg attatgccgg tgctgccggg cctcctgcgc 5040
gatctggttc actcgaacga cgtcaccgcc cactatggca ttctgctggc gctgtatgcg 5100
ttggtgcaat ttgcctgcgc acctgtgctg ggcgcgctgt cggatcgttt cgggcggcgg 5160
ccaatcttgc tcgtctcgct ggccggcgcc actgtcgact acgccatcat ggcgacagcg 5220
cctttccttt gggttctcta tatcgggcgg atcgtggccg gcatcaccgg ggcgactggg 5280
gcggtagccg gcgcttatat tgccgatatc actgatggcg atgagcgcgc gcggcacttc 5340
ggcttcatga gcgcctgttt cgggttcggg atggtcgcgg gacctgtgct cggtgggctg 5400
atgggcggtt tctcccccca cgctccgttc ttcgccgcgg cagccttgaa cggcctcaat 5460
ttcctgacgg gctgtttcct tttgccggag tcgcacaaag gcgaacgccg gccgttacgc 5520
cgggaggctc tcaacccgct cgcttcgttc cggtgggccc ggggcatgac cgtcgtcgcc 5580
gccctgatgg cggtcttctt catcatgcaa cttgtcggac aggtgccggc cgcgctttgg 5640
gtcattttcg gcgaggatcg ctttcactgg gacgcgacca cgatcggcat ttcgcttgcc 5700
gcatttggca ttctgcattc actcgcccag gcaatgatca ccggccctgt agccgcccgg 5760
ctcggcgaaa ggcgggcact catgctcgga atgattgccg acggcacagg ctacatcctg 5820
cttgccttcg cgacacgggg atggatggcg ttcccgatca tggtcctgct tgcttcgggt 5880
ggcatcggaa tgccggcgct gcaagcaatg ttgtccaggc aggtggatga ggaacgtcag 5940
gggcagctgc aaggctcact ggcggcgctc accagcctga cctcgatcgt cggacccctc 6000
ctcttcacgg cgatctatgc ggcttctata acaacgtgga acgggtgggc atggattgca 6060
ggcgctgccc tctacttgct ctgcctgccg gcgctgcgtc gcgggctttg gagcggcgca 6120
gggcaacgag ccgatcgctg atcgtggaaa cgataggcct atgccatgcg ggtcaaggcg 6180
actccttttt gataatctca tgaccaaaat cccttaacgt gagttttcgt tccactgagc 6240
gtcagacccc gtagaaaaga tcaaaggatc ttcttgagat cctttttttc tgcgcgtaat 6300
ctgctgcttg caaacaaaaa aaccaccgct accagcggtg gtttgtttgc cggatcaaga 6360
gctaccaact ctttttccga aggtaactgg cttcagcaga gcgcagatac caaatactgt 6420
tcttctagtg tagccgtagt taggccacca cttcaagaac tctgtagcac cgcctacata 6480

-continued

```
cctcgctctg ctaatcctgt taccagtggc tgctgccagt ggcgataagt cgtgtcttac   6540
cgggttggac tcaagacgat agttaccgga taaggcgcag cggtcgggct gaacgggggg   6600
ttcgtgcaca cagcccagct tggagcgaac gacctacacc gaactgagat acctacagcg   6660
tgagctatga gaaagcgcca cgcttcccga agggagaaag gcggacaggt atccggtaag   6720
cggcagggtc ggaacaggag agcgcacgag ggagcttcca gggggaaacg cctggtatct   6780
ttatagtcct gtcgggtttc gccacctctg acttgagcgt cgatttttgt gatgctcgtc   6840
aggggggcgg agcctatgga aaaacgccag caacgcggcc tttttacggt tcctggcctt   6900
ttgctggcct tttgctcaca tgttctttcc tgcgttatcc cctgattctg tggataaccg   6960
tattaccgcc tttgagtgag ctgataccgc tcgccgcagc cgaacgaccg agcgcagcga   7020
gtcagtgagc gaggaagcgg aagagcgccc aatacgcaat tgtcgcacag gtgccggaaa   7080
aagaaaaacg ggacgtatcg gaggatacgt cccgtttttt tatggcctct ggccagccgg   7140
cggaattcag acaagctgtg accgtctccg ggagctgcat gtgtcagagg ttttcaccgt   7200
catcaccgaa acgcgcgagg cagcagatca attcgcgcgc gaaggcgaag cggcatgcat   7260
aatgtgcctg tcaaatggac gaagcaggga ttctgcaaac cctatgctac tccgtcaagc   7320
cgtcaattgt ctgattcgtt accaattatg acaacttgac ggctacatca ttcacttttt   7380
cttcacaacc ggcacggaac tcgctcgggc tggccccggt gcatttttta aatacccgcg   7440
agaaatagag ttgatcgtca aaaccaacat tgcgaccgac ggtggcgata ggcatccggg   7500
tggtgctcaa aagcagcttc gcctggctga tacgttggtc ctcgcgccag cttaagacgc   7560
taatccctaa ctgctggcgg aaaagatgtg acagacgcga cggcgacaag caaacatgct   7620
gtgcgacgct ggcgatatca aaattgctgt ctgccaggtg atcgctgatg tactgacaag   7680
cctcgcgtac ccgattatcc atcggtggat ggagcgactc gttaatcgct tccatgcgcc   7740
gcagtaacaa ttgctcaagc agatttatcg ccagcagctc cgaatagcgc ccttcccctt   7800
gcccggcgtt aatgatttgc ccaaacaggt cgctgaaatg cggctggtgc gcttcatccg   7860
ggcgaaagaa ccccgtattg gcaaatattg acggccagtt aagccattca tgccagtagg   7920
cgcgcggacg aaagtaaacc cactggtgat accattcgcg agcctccgga tgacgaccgt   7980
agtgatgaat ctctcctggc gggaacagca aaatatcacc cggtcggcaa acaaattctc   8040
gtccctgatt tttcaccacc ccctgaccgc gaatggtgag attgagaata taacctttca   8100
ttcccagcgg tcggtcgata aaaaaatcga gataaccgtt ggcctcaatc ggcgttaaac   8160
ccgccaccag atgggcatta aacgagtatc ccggcagcag gggatcattt tgcgcttcag   8220
ccatactttt catactcccg ccattcagag aagaaaccaa ttgtccatat tgcatcagac   8280
attgccgtca ctgcgtcttt tactggctct tctcgctaac caaaccggta accccgctta   8340
ttaaaagcat tctgtaacaa agcgggacca aagccatgac aaaaacgcgt aacaaaagtg   8400
tctataatca cggcagaaaa gtccacattg attatttgca cggcgtcaca ctttgctatg   8460
ccatagcatt tttatccata agattagcgg atcctacctg acgcttttta tcgcaactct   8520
ctactgtttc tccatagacg tcggcgcgcc ttgtttaact ttaagaagga gatatacata   8580
tgaccaagaa ggtcggcgtg ggccaggccc acagcaagat cattctgatc ggcgagcacg   8640
ccgtggtgta tggctacccg gccatcagcc tgccgctgct ggaagtcgaa gtgacgtgca   8700
aggtggtgcc ggccgaatcc ccgtggcgtc tgtatgaaga ggacacgctg tcgatggccg   8760
tgtatgccag cctggagtac ctgaacatca ccgaggcctg catccgctgc gagatcgact   8820
ccgcgatccc ggagaagcgc ggcatgggca gctcggccgc catctccatc gccgcgatcc   8880
```

-continued

```
gcgccgtgtt cgactactac caagcggatc tgccgcatga cgtgctggag atcctggtga   8940
accgggccga aatgatcgcc cacatgaatc cgagcggtct ggatgccaag acgtgcctgt   9000
ccgaccagcc gatccgtttc atcaagaacg tgggtttcac cgagctggag atggatctga   9060
gcgcgtacct ggtgatcgcg gacaccggcg tgtacggcca cacccgcgag gccatccagg   9120
tcgtgcaaaa taagggtaag gacgccctgc cctttctgca cgccctgggc gaactcaccc   9180
agcaggccga agtcgcgatt tcccagaagg acgccgaggg cctgggtcaa atcctgagcc   9240
aggcgcatct gcacctgaag gagatcggcg tgagcagccc ggaagcggac ttcctggtcg   9300
aaaccaccct gtcgcacggt gccctgggcg cgaagatgtc gggcggcggc ctgggcggct   9360
gcatcatcgc gctggtcacc aacctgaccc atgcgcaaga gctggccgag cgcctggaag   9420
aaaagggcgc cgtccagacg tggatcgaat cgctctgagg attacacacc cacattacat   9480
gtaagtacga agaagaagcc aaggagatat acatatgatc gccgtcaaga cgtgcggcaa   9540
gctgtactgg gcgggcgagt atgccatcct cgaacccggc cagctggccc tgatcaagga   9600
catcccgatc tatatgcgtg ccgaaatcgc gttcagcgat tcgtaccgca tctattcgga   9660
tatgttcgac ttcgccgtcg atctgcgccc caatcccgac tactcgctga tccaagaaac   9720
catcgcgctc atgggcgact tcctcgccgt ccgcggtcag aatctgcgcc cgttcagcct   9780
ggagatttgc ggcaagatgg agcgcgaggg taagaagttc ggcctgggct cctcgggctc   9840
cgtggtggtc ctggtcgtga aggcgctgct ggcgctgtac gatgtctcgg tggaccaaga   9900
gctgctgttc aagctgacct cggccgtgct cctgaagcgc ggcgacaacg gctccatggg   9960
cgacctcgcg tgcatcgtgg ccgaggacct ggtcctgtac cagtcgtttg accgccagaa  10020
ggtggcggcg tggctggaag aagagaacct ggccacggtg ctggagcgtg actggggctt  10080
ctccatctcc caggtgaagc cgaccctgga atgcgacttc ctcgtgggct ggaccaagga  10140
agtggcggtg tccagccaca tggtgcaaca gatcaagcag aacattaacc agaattttct  10200
gacctcgtcg aaggaaaccg tcacgagcct ggtggaagcc ctggagcagg gcaagtcgga  10260
gaagatcatc gaccaggtcg aggtcgcctc caagctgctg gaaggcctgt ccacggatat  10320
ctacaccccc ctgctgcgcc aactgaagga agcctcgcag gacctccaga ccgtggccaa  10380
gagcagcggc gccggcggcg gcgactgcgg catcgccctg tccttcgacg cgcagtccac  10440
caagaccctg aagaaccggt gggcggacct gggcatcgag ctcctgtacc aagagcggat  10500
cggccacgac gacaagtcgt gaggctaggg taggacacca gctagccatt cggcgcaaag  10560
ggatggcaag gagatataca tatggaccgc gaaccggtca ccgtgcgctc gtacgcgaac  10620
atcgccatca tcaagtattg gggcaagaag aaggaaaagg aaatggtccc ggccacctcc  10680
agcatctcgc tgacgctgga gaatatgtac accgaaacga ccctgtcgcc cctgcccgcg  10740
aacgtcaccg cggacgagtt ctatatcaac ggccagctgc agaacgaagt ggagcatgcg  10800
aagatgagca agattatcga tcggtaccgc ccggccggcg agggctttgt gcgcatcgac  10860
acgcagaata acatgccgac ggccgcgggc ctgagcagca gctcgtcggg cctctccgcc  10920
ctggtcaagg cctgcaacgc ctacttcaag ctgggcctgg accgctcgca gctcgcgcaa  10980
gaagccaagt ttgccagcgg ctcgtcctcc cgcagctttt acggcccgct gggcgcgtgg  11040
gacaaggact cgggcgaaat ctacccggtg gaaacggacc tcaagctggc catgatcatg  11100
ctggtcctgg aagataagaa gaagccgatc tccagccgcg acggcatgaa gctgtgcgtc  11160
gaaaccagca ccacgttcga tgactgggtg cggcagagcg aaaaggacta ccaagacatg  11220
```

```
ctgatttacc tgaaggaaaa cgacttcgcg aagatcggcg aactgaccga gaagaatgcg  11280

ctggcgatgc acgcgacgac caagaccgcc tcgcccgcct tctcgtacct gaccgacgcc  11340

agctacgaag ccatggcctt cgtgcgccaa ctccgcgaaa agggcgaggc gtgctacttc  11400

acgatggacg ccggcccgaa cgtcaaggtg ttctgccagg aaaaggatct ggaacatctg  11460

tccgaaatct tcggccaccg ctaccgcctg atcgtgagca agaccaagga tctgtcgcaa  11520

gacgactgct gctgagtgca cgtatattag ttaagtataa gaaggagata taatcatgac  11580

gaccaaccgc aaggatgagc acatcctcta cgccctggag cagaagtcgt cgtacaactc  11640

gttcgacgaa gtggaactga tccactcgtc gctgccgctg tataacctgg acgaaatcga  11700

cctgtccacc gagttcgccg gccgcaagtg ggatttcccg ttctacatca atgccatgac  11760

cggcggtagc aacaagggcc gcgaaatcaa tcagaagctg gcccaggtcg ccgagtcgtg  11820

cggcatcctg ttcgtcaccg gcagctactc cgccgcgctg aagaacccga ccgacgactc  11880

gttctcggtc aagagcagcc acccgaatct gctgctgggc acgaacatcg gcctcgacaa  11940

gcccgtcgaa ctgggcctgc agaccgtgga agaaatgaac cccgtgctgc tccaggtgca  12000

tgtgaacgtg atgcaagagc tgctgatgcc ggagggcgaa cgcaagttcc gcagctggca  12060

gtcgcacctg gccgactact cgaagcagat ccccgtgccg atcgtgctga aagaagtggg  12120

cttcggcatg gacgccaaga ccatcgagcg tgcctacgag ttcggcgtgc gcaccgtgga  12180

cctctcgggc cgcggtggca cgagcttcgc gtacatcgaa aaccggcgca gcggccagcg  12240

cgactacctg aaccagtggg gccaatcgac catgcaggcc ctgctgaacg cgcaagaatg  12300

gaaggacaag gtcgagctgc tggtgtcggg cggcgtgcgt aacccgctcg acatgatcaa  12360

gtgcctggtg ttcggcgcca aggccgtggg cctgtcccgc accgtgctgg agctggtcga  12420

aacctacacc gtcgaagaag tcatcggcat tgtccagggc tggaaggccg acctccgcct  12480

catcatgtgc tccctgaact gcgccacgat cgcggacctc cagaaggtgg actatctcct  12540

ctacggcaag ctcaaagaag ccaaggacca gatgaagaag gcgtgaacta gtccaggcat  12600

caaataaaac gaaaggctca gtcgaaagac tgggcctttc gttttatctg ttgtttgtcg  12660

gtgaacgctc tcctgagtag gacaaatccg ccgggagcgg atttgaacgt tgcgaagcaa  12720

cggcccggag ggtggcgggc aggacgcccg ccataaactg ccaggcatca aattaagcag  12780

aaggccatcc tgacggatgg cctttttgcg tttctacaaa ctcttcctag gttaattaag  12840

cggccgcaaa aggacgggag tgggacagcg tagccatagt ccgagccgaa gag         12893
```

<210> SEQ ID NO 46
<211> LENGTH: 8139
<212> TYPE: DNA
<213> ORGANISM: artificial sequence
<220> FEATURE:
<223> OTHER INFORMATION: Synthetic

<400> SEQUENCE: 46

```
ctcgatgccc cgttgcagcc ctagatcggc cacagcggcc gcaaacgtgg tctggtcgcg     60

ggtcatctgc gctttgttgc cgatgaactc cttggccgac agcctgccgt cctgcgtcag    120

cggcaccacg aacgcggtca tgtgcgggct ggtttcgtca cggtggatgc tggccgtcac    180

gatgcgatcc gccccgtact tgtccgccag ccacttgtgc gccttctcga agaacgccgc    240

ctgctgttct tggctggccg acttccacca ttccgggctg gccgtcatga cgtactcgac    300

cgccaacaca gcgtccttgc gccgcttctc tggcagcaac tcgcgcagtc ggcccatcgc    360

ttcatcggtg ctgctggccg cccagtgctc gttctctggc gtcctgctgg cgtcagcgtt    420
```

-continued

```
gggcgtctcg cgctcgcggt aggcgtgctt gagactggcc gccacgttgc ccattttcgc    480
cagcttcttg catcgcatga tcgcgtatgc cgccatgcct gcccctccct tttggtgtcc    540
aaccggctcg acgggggcag cgcaaggcgg tgcctccggc gggccactca atgcttgagt    600
atactcacta gactttgctt cgcaaagtcg tgaccgccta cggcggctgc ggcgccctac    660
gggcttgctc tccgggcttc gccctgcgcg gtcgctgcgc tcccttgcca gcccgtggat    720
atgtggacga tggccgcgag cggccaccgg ctggctcgct tcgctcggcc cgtggacaac    780
cctgctggac aagctgatgg acaggctgcg cctgcccacg agcttgacca cagggattgc    840
ccaccggcta cccagccttc gaccacatac ccaccggctc caactgcgcg gcctgcggcc    900
ttgccccatc aatttttta attttctctg gggaaaagcc tccggcctgc ggcctgcgcg    960
cttcgcttgc cggttggaca ccaagtggaa ggcgggtcaa ggctcgcgca gcgaccgcgc   1020
agcggcttgg ccttgacgcg cctggaacga cccaagccta tgcgagtggg ggcagtcgaa   1080
ggcgaagccc gcccgcctgc cccccgagcc tcacggcggc gagtgcgggg gttccaaggg   1140
ggcagcgcca ccttgggcaa ggccgaaggc cgcgcagtcg atcaacaagc cccggagggg   1200
ccactttttg ccggaggggg agccgcgccg aaggcgtggg ggaaccccgc aggggtgccc   1260
ttctttgggc accaaagaac tagatatagg gcgaaatgcg aaagacttaa aaatcaacaa   1320
cttaaaaaag gggggtacgc aacagctcat tgcggcaccc cccgcaatag ctcattgcgt   1380
aggttaaaga aaatctgtaa ttgactgcca cttttacgca acgcataatt gttgtcgcgc   1440
tgccgaaaag ttgcagctga ttgcgcatgg tgccgcaacc gtgcggcacc ctaccgcatg   1500
gagataagca tggccacgca gtccagagaa atcggcattc aagccaagaa caagcccggt   1560
cactgggtgc aaacggaacg caaagcgcat gaggcgtggg ccgggcttat tgcgaggaaa   1620
cccacggcgg caatgctgct gcatcacctc gtggcgcaga tgggccacca gaacgccgtg   1680
gtggtcagcc agaagacact ttccaagctc atcggacgtt ctttgcggac ggtccaatac   1740
gcagtcaagg acttggtggc cgagcgctgg atctccgtcg tgaagctcaa cggccccggc   1800
accgtgtcgg cctacgtggt caatgaccgc gtggcgtggg gccagccccg cgaccagttg   1860
cgcctgtcgg tgttcagtgc cgccgtggtg gttgatcacg acgaccagga cgaatcgctg   1920
ttggggcatg gcgacctgcg ccgcatcccg accctgtatc cgggcgagca gcaactaccg   1980
accggccccg gcgaggagcc gcccagccag cccggcattc cgggcatgga accagacctg   2040
ccagccttga ccgaaacgga ggaatgggaa cggcgcgggc agcagcgcct gccgatgccc   2100
gatgagccgt gttttctgga cgatggcgag ccgttggagc cgccgacacg ggtcacgctg   2160
ccgcgccggt agcacttggg ttgcgcagca acccgtaagt gcgctgttcc agactatcgg   2220
ctgtagccgc ctctagatta attaacctcc agcgcgggga tctcatgctg gagttcttcg   2280
cccaccccca gacaagctgt gaccgtctcc gggagctgca tgtgtcagag gttttcaccg   2340
tcatcaccga aacgcgcgag gcagcagatc aattcgcgcg cgaaggcgaa gcggcatgca   2400
taatgtgcct gtcaaatgga cgaagcaggg attctgcaaa ccctatgcta ctccgtcaag   2460
ccgtcaattg tctgattcgt taccaattat gacaacttga cggctacatc attcactttt   2520
tcttcacaac cggcacggaa ctcgctcggg ctggccccgg tgcatttttt aaatacccgc   2580
gagaaataga gttgatcgtc aaaaccaaca ttgcgaccga cggtggcgat aggcatccgg   2640
gtggtgctca aaagcagctt cgcctggctg atacgttggt cctcgcgcca gcttaagacg   2700
ctaatcccta actgctggcg gaaaagatgt gacagacgcg acggcgacaa gcaaacatgc   2760
```

-continued tgtgcgacgc tggcgatatc aaaattgctg tctgccaggt gatcgctgat gtactgacaa 2820
gcctcgcgta cccgattatc catcggtgga tggagcgact cgttaatcgc ttccatgcgc 2880
cgcagtaaca attgctcaag cagatttatc gccagcagct ccgaatagcg cccttcccct 2940
tgcccggcgt taatgatttg cccaaacagg tcgctgaaat gcggctggtg cgcttcatcc 3000
gggcgaaaga accccgtatt ggcaaatatt gacggccagt taagccattc atgccagtag 3060
gcgcgcggac gaaagtaaac ccactggtga taccattcgc gagcctccgg atgacgaccg 3120
tagtgatgaa tctctcctgg cgggaacagc aaaatatcac ccggtcggca aacaaattct 3180
cgtccctgat ttttcaccac cccctgaccg cgaatggtga gattgagaat ataacctttc 3240
attcccagcg gtcggtcgat aaaaaaatcg agataaccgt tggcctcaat cggcgttaaa 3300
cccgccacca gatgggcatt aaacgagtat cccggcagca ggggatcatt ttgcgcttca 3360
gccatacttt tcatactccc gccattcaga gaagaaacca attgtccata ttgcatcaga 3420
cattgccgtc actgcgtctt ttactggctc ttctcgctaa ccaaaccggt aaccccgctt 3480
attaaaagca ttctgtaaca aagcgggacc aaagccatga caaaaacgcg taacaaaagt 3540
gtctataatc acggcagaaa agtccacatt gattatttgc acggcgtcac actttgctat 3600
gccatagcat ttttatccat aagattagcg gatcctacct gacgcttttt atcgcaactc 3660
tctactgttt ctccataccc gtttttttggg ctagaaataa ttttgagctc gccaaggaga 3720
tataatggtc acgcgcgcgg agcgcaagcg ccagcacatc aaccacgcgc tctccatcgg 3780
ccagaagcgc gaaaccggcc tggacgacat cacgtttgtg catgtctcgc tgccggacct 3840
ggccctcgaa caggtcgaca tctcgacgaa gattggcgag ctgagctcct cgtcgccgat 3900
cttcatcaac gcgatgaccg gcggtggtgg caagctgacc tacgagatca acaagtccct 3960
ggcgcgcgcg gccagccagg ccggcatccc gctggcggtc ggcagccaga tgtcggccct 4020
gaaggacccc agcgagcgcc tgtcgtacga gattgtccgc aaggaaaacc cgaacggcct 4080
gatcttcgcc aatctgggct cggaagccac cgcggcgcag gccaaagaag cggtggagat 4140
gatcggcgcc aacgccctgc agatccacct gaacgtgatc caagagatcg tgatgcccga 4200
gggcgaccgt tccttctccg gcgccctcaa gcgcatcgag caaatctgca gccgcgtgtc 4260
ggtgcccgtc atcgtcaagg aagtgggctt cggcatgtcg aaggccagcg ccggcaagct 4320
gtacgaagcc ggcgcggccg ccgtggacat cggcggctac ggcggcacga acttcagcaa 4380
gattgagaat ctgcgccgcc agcggcagat cagcttcttc aactcgtggg gcatcagcac 4440
ggccgcgtcg ctggcggaga tccggtccga gttcccggcc tcgaccatga tcgcgtccgg 4500
tggcctccaa gacgccctgg acgtcgccaa ggccatcgcc ctgggcgcga gctgcaccgg 4560
catggccggt cacttcctga aggccctgac cgatagcggc gaggaaggcc tgctggaaga 4620
gatccagctg atcctggaag aactgaagct gatcatgacg gtgctgggcg cccgtaccat 4680
cgcggatctg caaaaggcgc cgctcgtgat caagggcgaa acccatcact ggctcaccga 4740
gcggggcgtg aacaccagct cgtattcggt gcgctgactt taaggaagga gcgaagcatg 4800
cgttgtagcg ttagcaccga aaatgtgtcg tttacggaaa cggaaaccga agctcgccgc 4860
agcgcaaact atgaaccgaa ctcgtgggat tacgattacc tccttagcag cgatacggat 4920
gaaagcattg aagtgtataa agacaaagcc aagaaactgg aggccgaagt ccgtcgcgaa 4980
atcaacaatg agaaagcgga gtttcttacg ttactggaat tgatcgataa cgtgcaacgg 5040
ttaggcctcg gctaccgctt tgagagcgat atccgtggtg cactggaccg cttcgtatcg 5100
tctggtggtt ttgacgccgt tacgaaaacg agcctgcatg gtacagcatt gtcttttcgg 5160

```
ctgttgcgcc agcatggatt tgaagtgtca caggaggcat tttcaggctt caaagaccag   5220
aacgggaatt ttttggagaa tttgaaagaa gatatcaaag cgatcttatc tctgtatgag   5280
gcgtcatttc tcgctctgga aggggaaaat attctggacg aagcgaaagt gttcgcaatt   5340
tcccatctga aagaactttc cgaagaaaag attgggaaag aattggccga acaggtgaac   5400
catgcgctgg aactgccact gcaccgtcgc acccaacgcc tcgaagcggt atggtcgatt   5460
gaagcgtatc gcaaaaaaga ggatgcaaat caggttctgc tggaactggc cattctcgac   5520
tataacatga ttcagtccgt ctatcaacgt gatctgcgcg aaactagtcg ttggtggcgc   5580
cgtgtaggac ttgccactaa actgcatttt gcacgtgatc gtctgattga gtcgttctat   5640
tgggcggttg gtgtagcgtt tgagccgcag tattctgatt gccgcaatag tgtggcgaaa   5700
atgttctcct ttgtgaccat cattgacgat atttacgacg tgtatggcac cctggatgaa   5760
ctggaattat tcaccgatgc agtagaacgc tgggacgtca acgcgatcaa tgatttgccg   5820
gattacatga aactgtgttt tctggccctg tataacacca ttaacgaaat tgcctatgac   5880
aacctcaaag acaagggtga aaatatcctg ccctatctga ctaaagcttg ggctgatctg   5940
tgtaacgcgt tcttacagga agccaaatgg ctctacaaca agagtacgcc tactttcgat   6000
gactactttg gcaacgcttg gaaaagctct agcggccctt tacaactggt gttcgcgtat   6060
ttcgccgttg ttcagaatat caagaaagaa gagattgaga acctccaaaa gtaccacgat   6120
acgatttcgc gtccgtcaca catctttcgc ctttgcaatg atttggccag tgcatctgca   6180
gagattgcgc gcggtgaaac tgccaactcc gtcagttgct acatgcgtac caaaggcatc   6240
agcgaggaac tggctaccga gtcggtgatg aacttaatcg atgaaacctg gaagaagatg   6300
aacaaagaga aacttggtgg cagtctgttt gctaaaccgt tcgttgagac agcgattaat   6360
ctggcgcgtc aaagccactg cacctaccac aatggcgatg cccacacatc cccagacgaa   6420
ttaacccgga aacgtgtcct gagtgtcatc accgaaccca ttctgccgtt cgaacgctga   6480
tcgctgcgcg agccttgacc cgccttccac ttgtgaatgt cagctactgg gctatctgga   6540
caagggaaaa cgcaagcgca aagagaaagc aggtagcttg cagtgggctt acatggcgat   6600
agctagactg ggcggtttta tggacagcaa gcgaaccgga attgccagct ggggcgccct   6660
ctggtaaggt tgggaagccc tgcaaagtaa actggatggc tttcttgccg ccaaggatct   6720
gatggcgcag gggatcaaga tctgatcaag agacaggatg aggatcgttt cgcatgattg   6780
aacaagatgg attgcacgca ggttctccgg ccgcttgggt ggagaggcta ttcggctatg   6840
actgggcaca acagacaatc ggctgctctg atgccgccgt gttccggctg tcagcgcagg   6900
ggcgcccggt tctttttgtc aagaccgacc tgtccggtgc cctgaatgaa ctgcaggacg   6960
aggcagcgcg gctatcgtgg ctggccacga cgggcgttcc ttgcgcagct gtgctcgacg   7020
ttgtcactga agcgggaagg gactggctgc tattgggcga agtgccgggg caggatctcc   7080
tgtcatctca ccttgctcct gccgagaaag tatccatcat ggctgatgca atgcggcggc   7140
tgcatacgct tgatccggct acctgcccat tcgaccacca agcgaaacat cgcatcgagc   7200
gagcacgtac tcggatggaa gccggtcttg tcgatcagga tgatctggac gaagagcatc   7260
aggggctcgc gccagccgaa ctgttcgcca ggctcaaggc gcgcatgccc gacggcgagg   7320
atctcgtcgt gacccatggc gatgcctgct tgccgaatat catggtggaa aatggccgct   7380
tttctggatt catcgactgt ggccggctgg gtgtggcgga ccgctatcag gacatagcgt   7440
tggctacccg tgatattgct gaagagcttg gcggcgaatg ggctgaccgc ttcctcgtgc   7500
```

-continued

```
tttacggtat cgccgctccc gattcgcagc gcatcgcctt ctatcgcctt cttgacgagt   7560
tcttctgagc gggactctgg gggaattctt gaagacgaaa gggcctcgtg atacgcctat   7620
ttttataggt taatgtcatg ataataatgg tttcttagac gtcaggtggc acttttcggg   7680
gaaatgtgcg cgcccgcgtt cctgctggcg ctgggcctgt ttctggcgct ggacttcccg   7740
ctgttccgtc agcagctttt cgcccacggc cttgatgatc gcggcggcct tggcctgcat   7800
atcccgattc aacggcccca gggcgtccag aacgggcttc aggcgctccc gaaggtctcg   7860
ggccgtctct tgggcttgat cggccttctt gcgcatctca cgcgctcctg cggcggcctg   7920
tagggcaggc tcatacccct gccgaaccgc ttttgtcagc cggtcggcca cggcttccgg   7980
cgtctcaacg cgctttgaga ttcccagctt ttcggccaat ccctgcggtg cataggcgcg   8040
tggctcgacc gcttgcgggc tgatggtgac gtggcccact ggtggccgct ccagggcctc   8100
gtagaacgcc tgaatgcgcg tgtgacgtgc cttgctgcc                          8139
```

<210> SEQ ID NO 47
<211> LENGTH: 6924
<212> TYPE: DNA
<213> ORGANISM: artificial sequence
<220> FEATURE:
<223> OTHER INFORMATION: Synthetic

<400> SEQUENCE: 47

```
aacgacggcc agtgagcgcg cgtaatacga ctcactatag ggcgaattgg agctccaccg     60
cggtggcggc cgcgaagaca atggccctgc attctagacc tgcaggtcac actggctcac    120
cttcgggtgg gcctttctgc gtttatatac tagagagaga atataaaaag ccagattatt    180
aatccggctt ttttattatt tttatgacaa cttgacggct acatcattca ctttttcttc    240
acaaccggca cggaactcgc tcgggctggc cccggtgcat tttttaaata cccgcgagaa    300
atagagttga tcgtcaaaac caacattgcg accgacggtg gcgataggca tccgggtggt    360
gctcaaaagc agcttcgcct ggctgatacg ttggtcctcg cgccagctta agacgctaat    420
ccctaactgc tggcggaaaa gatgtgacag acgcgacggc gacaagcaaa catgctgtgc    480
gacgctggcg atatcaaaat tgctgtctgc caggtgatcg ctgatgtact gacaagcctc    540
gcgtacccga ttatccatcg gtggatggag cgactcgtta atcgcttcca tgcgccgcag    600
taacaattgc tcaagcagat ttatcgccag cagctccgaa tagcgccctt ccccttgccc    660
ggcgttaatg atttgcccaa acaggtcgct gaaatgcggc tggtgcgctt catccgggcg    720
aaagaacccc gtattggcaa atattgacgg ccagttaagc cattcatgcc agtaggcgcg    780
cggacgaaag taaacccact ggtgatacca ttcgcgagcc tccggatgac gaccgtagtg    840
atgaatctct cctggcggga acagcaaaat atcacccggt cggcaaacaa attctcgtcc    900
ctgatttttc accacccccct gaccgcgaat ggtgagattg agaatataac ctttcattcc    960
cagcggtcgg tcgataaaaa aatcgagata accgttggcc tcaatcggcg ttaaacccgc   1020
caccagatgg gcattaaacg agtatcccgg cagcagggga tcattttgcg cttcagccat   1080
acttttcata ctcccgccat tcagagaaga aaccaattgt ccatattgca tcagacattg   1140
ccgtcactgc gtcttttact ggctcttctc gctaaccaaa ccggtaaccc cgcttattaa   1200
aagcattctg taacaaagcg ggaccaaagc catgacaaaa acgcgtaaca aaagtgtcta   1260
taatcacggc agaaaagtcc acattgatta tttgcacggc gtcacacttt gctatgccat   1320
agcattttta tccataagat tagcggatcc tacctgacgc tttttatcgc aactctctac   1380
tgtttctcca tagacgtcgg cgcgccctga attgtgatta aaaaggcaac tttatgccca   1440
```

-continued

```
tgcaacagaa actataaaaa atacagagaa tgaaaagaaa cagatagatt ttttagttct   1500
ttaggcccgt agtctgcaaa tccttttatg attttctatc aaacaaaaga ggaaaataga   1560
ccagttgcaa tccaaacgag agtctaatag aatgaggtcg aaaagtaaat cgcgcgggtt   1620
tgttactgat aaagcaggca agacctaaaa tgtgtaaagg gcaaagtgta tactttggcg   1680
tcacccctta catattttag gtcttttttt attgtgcgta actaacttgc catcttcaaa   1740
caggagggct ggaagaagca gaccgctaac acagtacata aaaaaggaga catgaacgat   1800
gaacatcaaa aagtttgcaa aacaagcaac agtattaacc tttactaccg cactgctggc   1860
aggaggcgca actcaagcgt ttgcgaaaga aacgaaccaa aagccatata aggaaacata   1920
cggcatttcc catattacac gccatgatat gctgcaaatc cctgaacagc aaaaaaatga   1980
aaaatatcaa gtttctgaat ttgattcgtc cacaattaaa aatatctctt ctgcaaaagg   2040
cctggacgtt tgggacagct ggccattaca aaacgctgac ggcactgtcg caaactatca   2100
cggctaccac atcgtctttg cattagccgg agatcctaaa aatgcggatg acacatcgat   2160
ttacatgttc tatcaaaaag tcggcgaaac ttctattgac agctggaaaa acgctggccg   2220
cgtctttaaa gacagcgaca aattcgatgc aaatgattct atcctaaaag accaaacaca   2280
agaatggtca ggttcagcca catttacatc tgacggaaaa atccgtttat tctacactga   2340
tttctccggt aaacattacg gcaaacaaac actgacaact gcacaagtta acgtatcagc   2400
atcagacagc tctttgaaca tcaacggtgt agaggattat aaatcaatct ttgacggtga   2460
cggaaaaacg tatcaaaatg tacagcagtt catcgatgaa ggcaactaca gctcaggcga   2520
caaccatacg ctgagagatc ctcactacgt agaagataaa ggccacaaat acttagtatt   2580
tgaagcaaac actggaactg aagatggcta ccaaggcgaa gaatctttat ttaacaaagc   2640
atactatggc aaaagcacat cattcttccg tcaagaaagt caaaaacttc tgcaaagcga   2700
taaaaaacgc acggctgagt tagcaaacgg cgctctcggt atgattgagc taaacgatga   2760
ttacacactg aaaaaagtga tgaaaccgct gattgcatct aacacagtaa cagatgaaat   2820
tgaacgcgcg aacgtcttta aaatgaacgg caaatggtac ctgttcactg actcccgcgg   2880
atcaaaaatg acgattgacg gcattacgtc taacgatatt tacatgcttg gttatgtttc   2940
taattcttta actggcccat acaagccgct gaacaaaact ggccttgtgt taaaaatgga   3000
tcttgatcct aacgatgtaa cctttactta ctcacacttc gctgtacctc aagcgaaagg   3060
aaacaatgtc gtgattacaa gctatatgac aaacagagga ttctacgcag acaaacaatc   3120
aacgtttgcg ccgagcttcc tgctgaacat caaaggcaag aaaacatctg ttgtcaaaga   3180
cagcatcctt gaacaaggac aattaacagt taacaaataa aaacgcaaaa gaaaatgccg   3240
atactagtcc aggcatcaaa taaaacgaaa ggctcagtcg aaagactggg cctttcgttt   3300
tatctgttgt ttgtcggtga acgctctcat cgttgtcttc gaattcgata tcaagcttat   3360
cgataccgtc gacctcgagg gggggcccgg tacccagctt ttgttccctt tagtgagggt   3420
taattgcgcg cttggcgtaa tcatggtcat agctgtttcc tgtgtgaaat tgttatccgc   3480
tcacaattcc acacaacata cgagccggaa gcataaagtg taaagcctgg ggtgcctaat   3540
gagtgagcta actcacatta attgcgttgc gctcactgcc cgctttccag tcgggaaacc   3600
tgtcgtgcca gctgcattaa tgaatcggcc aacgcgcggg gagaggcggt ttgcgtattg   3660
ggcgcatgca taaaaactgt tgtaattcat taagcattct gccgacatgg aagccatcac   3720
aaacggcatg atgaacctga atcgccagcg gcatcagcac cttgtcgcct tgcgtataat   3780
```

-continued

```
atttgcccat gggggtgggc gaagaactcc agcatgagat ccccgcgctg gaggatcatc   3840
cagccggcgt cccggaaaac gattccgaag cccaaccttt catagaaggc ggcggtggaa   3900
tcgaaatctc gtgatggcag gttgggcgtc gcttggtcgg tcatttcgaa ccccagagtc   3960
ccgctcagaa gaactcgtca agaaggcgat agaaggcgat gcgctgcgaa tcgggagcgg   4020
cgataccgta aagcacgagg aagcggtcag cccattcgcc gccaagctct tcagcaatat   4080
cacgggtagc caacgctatg tcctgatagc ggtccgccac acccagccgg ccacagtcga   4140
tgaatccaga aaagcggcca ttttccacca tgatattcgg caagcaggca tcgccatggg   4200
tcacgacgag atcctcgccg tcgggcatgc gcgccttgag cctggcgaac agttcggctg   4260
gcgcgagccc ctgatgctct tcgtccagat catcctgatc gacaagaccg gcttccatcc   4320
gagtacgtgc tcgctcgatg cgatgtttcg cttggtggtc gaatgggcag gtagccggat   4380
caagcgtatg cagccgccgc attgcatcag ccatgatgga tactttctcg gcaggagcaa   4440
ggtgagatga caggagatcc tgccccggca cttcgcccaa tagcagccag tcccttcccg   4500
cttcagtgac aacgtcgagc acagctgcgc aaggaacgcc cgtcgtggcc agccacgata   4560
gccgcgctgc ctcgtcctgc agttcattca gggcaccgga caggtcggtc ttgacaaaaa   4620
gaaccgggcg cccctgcgct gacagccgga acacggcggc atcagagcag ccgattgtct   4680
gttgtgccca gtcatagccg aatagcctct ccacccaagc ggccggagaa cctgcgtgca   4740
atccatcttg ttcaatcatg cgaaacgatc ctcatcctgt ctcttgatca gatcttgatc   4800
ccctgcgcca tcagatcctt ggcggcaaga aagccatcca gtttactttg cagggcttcc   4860
caaccttacc agagggcgcc ccagctggca attccggttc gcttgctgtc cataaaaccg   4920
cccagtctag ctatcgccat gtaagcccac tgcaagctac ctgctttctc tttgcgcttg   4980
cgttttccct tgtccagata gcccagtagc tgacattcac aagtggaagg cgggtcaagg   5040
ctcgcgcagc gaccgcgcag cggcttggcc ttgacgcgcc tggaacgacc caagcctatg   5100
cgagtggggg cagtcgaagg gcgaagcccg cccgcctgcc ccccgagcct cacggcggcg   5160
agtgcggggg ttccaagggg gcagcgccac cttgggcaag gccgaaggcc gcgcagtcga   5220
tcaacaagcc ccggaggggc cactttttgc cggaggggga gccgcgccga aggcgtgggg   5280
gaaccccgca ggggtgccct tctttgggca ccaaagaact agatataggg cgaaatgcga   5340
aagacttaaa aatcaacaac ttaaaaaagg ggggtacgca acagctcatt gcggcacccc   5400
ccgcaatagc tcattgcgta ggttaaagaa aatctgtaat tgactgccac ttttacgcaa   5460
cgcataattg ttgtcgcgct gccgaaaagt tgcagctgat tgcgcatggt gccgcaaccg   5520
tgcggcaccc ctaccgcatg gagataagca tggccacgca gtccagagaa atcggcattc   5580
aagccaagaa caagcccggt cactgggtgc aaacggaacg caaagcgcat gaggcgtggg   5640
ccgggcttat tgcgaggaaa cccacggcgg caatgctgct gcatcacctc gtggcgcaga   5700
tgggccacca gaacgccgtg gtggtcagcc aaaagacact ttccaagctc atcggacgtt   5760
ctttgcggac ggtccaatac gcagtcaagg acttggtggc cgagcgctgg atctccgtcg   5820
tgaagctcaa cggccccggc accgtgtcgg cctacgtggt caatgaccgc gtggcgtggg   5880
gccagccccg cgaccagttg cgcctgtcgg tgttcagtgc cgccgtggtg gttgatcacg   5940
acgaccagga cgaatcgctg ttggggcatg gcgacctgcg ccgcatcccg accctgtatc   6000
cgggcgagca gcaactaccg accggccccg gcgaggagcc gcccagccag cccggcattc   6060
cgggcatgga accagacctg ccagccttga ccgaaacgga ggaatgggaa cggcgcgggc   6120
agcagcgcct gccgatgccc gatgagccgt gttttctgga cgatggcgag ccgttggagc   6180
```

cgccgacacg ggtcacgctg ccgcgccggt agcacttggg ttgcgcagca acccgtaagt 6240
gcgctgttcc agactatcgg ctgtagccgc ctcgccgccc tataccttgt ctgcctcccc 6300
gcgttgcgtc gcggtgcatg gagccgggcc acctcgacct gaatggaagc cggcggcacc 6360
tcgctaacgg attcaccgtt tttatcaggc tctgggaggc agaataaatg atcatatcgt 6420
caattattac ctccacgggg agagcctgag caaactggcc tcaggcattt gagaagcaca 6480
cggtcacact gcttccggta gtcaataaac cggtaaacca gcaatagaca taagcggcta 6540
tttaacgacc ctgccctgaa ccgacgaccg ggtcgaattt gctttcgaat ttctgccatt 6600
catccgctta ttatcactta ttcaggcgta gcaaccaggc gtttaagggc accaataact 6660
gccttaaaaa aattacgccc cgccctgcca ctcatcgcag tacggcctat tggttaaaaa 6720
atgagctgat ttaacaaaaa tttaacgcga attttaacaa aatattaacg cttacaattt 6780
ccattcgcca ttcaggctgc gcaactgttg ggaagggcga tcggtgcggg cctcttcgct 6840
attacgccag ctggcgaaag ggggatgtgc tgcaaggcga ttaagttggg taacgccagg 6900
gttttcccag tcacgacgtt gtaa 6924

<210> SEQ ID NO 48
<211> LENGTH: 4894
<212> TYPE: DNA
<213> ORGANISM: artificial sequence
<220> FEATURE:
<223> OTHER INFORMATION: Synthetic

<400> SEQUENCE: 48
ttatgacaac ttgacggcta catcattcac tttttcttca caaccggcac ggaactcgct 60
cgggctggcc ccggtgcatt ttttaaatac ccgcgagaaa tagagttgat cgtcaaaacc 120
aacattgcga ccgacggtgg cgataggcat ccgggtggtg ctcaaaagca gcttcgcctg 180
gctgatacgt tggtcctcgc gccagcttaa gacgctaatc cctaactgct ggcggaaaag 240
atgtgacaga cgcgacggcg acaagcaaac atgctgtgcg acgctggcga tatcaaaatt 300
gctgtctgcc aggtgatcgc tgatgtactg acaagcctcg cgtacccgat tatccatcgg 360
tggatggagc gactcgttaa tcgcttccat gcgccgcagt aacaattgct caagcagatt 420
tatcgccagc agctccgaat agcgcccttc cccttgcccg gcgttaatga tttgcccaaa 480
caggtcgctg aaatgcggct ggtgcgcttc atccgggcga aagaaccccg tattggcaaa 540
tattgacggc cagttaagcc attcatgcca gtaggcgcgc ggacgaaagt aaacccactg 600
gtgataccat tcgcgagcct ccggatgacg accgtagtga tgaatctctc ctggcgggaa 660
cagcaaaata tcacccggtc ggcaaacaaa ttctcgtccc tgatttttca ccaccccctg 720
accgcgaatg gtgagattga gaatataacc tttcattccc agcggtcggt cgataaaaaa 780
atcgagataa ccgttggcct caatcggcgt taaacccgcc accagatggg cattaaacga 840
gtatcccggc agcaggggat cattttgcgc ttcagccata cttttcatac tcccgccatt 900
cagagaagaa accaattgtc catattgcat cagacattgc cgtcactgcg tcttttactg 960
gctcttctcg ctaaccaaac cggtaacccc gcttattaaa agcattctgt aacaaagcgg 1020
gaccaaagcc atgacaaaaa cgcgtaacaa aagtgtctat aatcacggca gaaaagtcca 1080
cattgattat ttgcacggcg tcacactttg ctatgccata gcatttttat ccataagatt 1140
agcggatcct acctgacgct ttttatcgca actctctact gtttctccat agacgtcggc 1200
gcgccttgtt taactttaag aaggagatat acatatggtg tcgtgctcgg ccccgggcaa 1260

-continued

```
gatttacttg ttcggcgaac atgccgtggt gtacggcgaa accgccatcg cctgcgccgt   1320
ggaactgcgt acccgcgtgc gtgccgagct gaatgattcg atcaccatcc agtcgcaaat   1380
cggccgcacc ggcctggact tcgagaagca cccgtacgtg tcggccgtga tcgagaagat   1440
gcgcaagtcg atcccgatca acggcgtgtt cctgaccgtg gattcggaca tcccggtggg   1500
ttcgggcctg ggctcgtcag ccgcagtgac cattgcctca atcggcgccc tgaacgagct   1560
gttcggcttc ggtctgtcgc tgcaggagat cgccaagctg ggccacgaga tcgaaatcaa   1620
ggtgcagggc gcggcaagcc cgaccgacac ctatgtgtca accttcggcg gcgtggtgac   1680
catcccagaa cgccgcaagc tgaaaacccc ggattgcggc atcgtgatcg gcgacaccgg   1740
cgtgttcagc agcaccaagg agttggtggc caacgtgcgc cagttgcgcg agtcgtaccc   1800
ggacctgatc gagccgctga tgacctcgat cggcaagatc agccgcatcg gcgagcagct   1860
ggtgttgtcg ggcgactatg ccagcatcgg ccgtctgatg aacgtgaacc agggcctgct   1920
ggacgccctg ggcgtgaaca tcctggaact gtcgcagctg atttattcgg cccgcgcggc   1980
cggcgcattc ggcgcaaaaa ttaccggtgc cggcggtggt ggctgtatgg ttgccttgac   2040
cgccccagag aagtgtaatc aggtggcaga agccatcgcg ggcgccggcg gcaaggtgac   2100
catcaccaag ccgaccgagc agggcctgaa ggtggactga ggattacaca cccacattac   2160
atgtaagtac gaagaagaag ccaaggagat atacatatgt cggaactgcg cgccttctcg   2220
gccccgggta aagccttgct ggccggtggc tacctggttc tggacaccaa gtatgaagcc   2280
ttcgtggtgg gcttgtcggc ccgcatgcat gccgtggccc atccgtacgg ctcactgcag   2340
ggctcggaca agtttgaggt gcgcgtgaag tcgaagcagt tcaaggacgg cgagtggctg   2400
taccacatct cgccgaagtc gggcttcatc ccggtgtcga tcggcggcag caagaacccg   2460
ttcatcgaga aggtgatcgc caacgtgttc tcgtacttca agccgaacat ggacgactac   2520
tgcaaccgca acctgttcgt gatcgacatc ttctcggacg acgcctacca ctcgcaggag   2580
gacagcgtga ccgagcaccg cggcaatcgc cgcctgtcgt tccacagcca tagaatcgaa   2640
gaggttccaa agaccggcct gggctcgtcg gcaggcctgg ttaccgtgct gaccaccgcc   2700
ctggcctcgt tttcgtgtc ggacctggag aacaacgtgg acaagtaccg cgaggtgatt   2760
cacaacctgg cccaagttgc ccattgccag gcccagggta agatcggctc gggtttcgac   2820
gtggccgccg ccgcctatgg ttcaatcaga taccgccgct ttccgccggc cctgatctcg   2880
aatttgccgg acattggctc ggccacctac ggctcgaagc tggcccatct ggtggacgag   2940
gaggactgga acatcaccat caagtcgaac cacctcccgt cgggcctgac cctgtggatg   3000
ggcgacatca agaacggctc ggaaaccgtg aagctggtgc agaaggtgaa gaactggtac   3060
gactcgcaca tgccggagag cctgaaaatc tacaccgagc tggaccacgc caactcgcgc   3120
ttcatggacg gcctgagcaa gctggaccgc ctgcacgaaa cccacgacga ctacagcgac   3180
caaatcttcg agtcgctgga gcgcaacgac tgcacgtgcc agaagtaccc ggagatcacc   3240
gaagtgcgcg acgccgtggc caccatccgt cgctcgtttc gcaagatcac caaggaatcg   3300
ggcgccgata tcgaaccgcc ggtgcagact tcgctgctgg atgactgcca gaccttgaag   3360
ggtgtgttga cctgcctgat cccaggcgcc ggcggctatg atgccatcgc cgtgatcacc   3420
aagcaggacg tggatctgcg cgcccagacc gccaacgata agcgcttctc gaaggtgcag   3480
tggctggacg ttacccaggc agactggggc gtgcgcaagg agaaggaccc ggaaacctac   3540
ctggacaagt gaggctaggg taggacacca gctagccatt cggcgcaaag ggatggcaag   3600
gagatataca tatgaccgtg tacaccgcca gcgtgaccgc cccggtgaac atcgccaccc   3660
```

tgaagtactg gggcaagcgc gataccaagc tgaatctgcc gaccaactcg tcgatctcgg 3720
tgaccctgtc acaggacgat ctgcgcaccc tgacctcggc agccaccgcc ccggagttcg 3780
aacgtgatac cctgtggttg aacggcgaac cgcactcgat tgacaacgag cgcacccaga 3840
actgcctgcg cgacctgcgc cagttgcgca aggaaatgga gagcaaggac gcctcgctgc 3900
cgaccctgag ccagtggaag ctgcatatcg tgtcggagaa caattttccg accgccgcag 3960
gcctggcctc atcggcagca ggcttcgccg ccctggtttc ggccatcgcc aagctgtatc 4020
agttgccgca gtcgacctcg gaaatttcga ggatcgcccg taagggctca ggtagcgcct 4080
gccgctcgct gtttggcggc tatgtggcat gggaaatggg caaggcagag gacggccacg 4140
actcgatggc agtgcagatc gccgactcgt cggactggcc gcagatgaag gcctgcgtgt 4200
tggtggtgtc ggacatcaag aaggacgtgt cgtcgaccca gggcatgcag ctgaccgtgg 4260
ccacctcgga gctgttcaag gagcgcattg agcacgtggt gccgaagcgc ttcgaggtga 4320
tgcgcaaggc catcgtggag aaggacttcg ccaccttcgc caaggagact atgatggact 4380
cgaactcgtt ccacgccacg tgcctggaca gcttcccgcc gatcttctac atgaacgaca 4440
ccagcaagcg catcatcagc tggtgccaca ccatcaacca gttctacggc gaaaccatcg 4500
tggcctacac cttcgacgcc ggcccgaacg ccgtgctgta ctacctggcc gagaacgagt 4560
cgaagctgtt cgccttcatc tacaagctgt tcggctcggt gccgggctgg gacaagaagt 4620
tcaccaccga gcagctggag gccttcaacc accagttcga atcgtcgaac ttcaccgccc 4680
gcgagctgga cctggaactg cagaaggatg tggcccgcgt gattctgacc caggtgggct 4740
cgggcccgca ggaaaccaac gaatcgctga tcgacgccaa gaccggcctg ccgaaggagt 4800
gagtgcacac tagtccaggc atcaaataaa acgaaaggct cagtcgaaag actgggcctt 4860
tcgttttatc tgttgtttgt cggtgaacgc tctc 4894

<210> SEQ ID NO 49
<211> LENGTH: 4282
<212> TYPE: DNA
<213> ORGANISM: artificial sequence
<220> FEATURE:
<223> OTHER INFORMATION: Synthetic

<400> SEQUENCE: 49
ttatgacaac ttgacggcta catcattcac tttttcttca caaccggcac ggaactcgct 60
cgggctggcc ccggtgcatt ttttaaatac ccgcgagaaa tagagttgat cgtcaaaacc 120
aacattgcga ccgacggtgg cgataggcat ccgggtggtg ctcaaaagca gcttcgcctg 180
gctgatacgt tggtcctcgc gccagcttaa gacgctaatc cctaactgct ggcggaaaag 240
atgtgacaga cgcgacggcg acaagcaaac atgctgtgcg acgctggcga tatcaaaatt 300
gctgtctgcc aggtgatcgc tgatgtactg acaagcctcg cgtacccgat tatccatcgg 360
tggatggagc gactcgttaa tcgcttccat gcgccgcagt aacaattgct caagcagatt 420
tatcgccagc agctccgaat agcgcccttc cccttgcccg gcgttaatga tttgcccaaa 480
caggtcgctg aaatgcggct ggtgcgcttc atccgggcga aagaaccccg tattggcaaa 540
tattgacggc cagttaagcc attcatgcca gtaggcgcgc ggacgaaagt aaacccactg 600
gtgataccat tcgcgagcct ccggatgacg accgtagtga tgaatctctc ctggcgggaa 660
cagcaaaata tcacccggtc ggcaaacaaa ttctcgtccc tgatttttca ccaccccctg 720
accgcgaatg gtgagattga gaatataacc tttcattccc agcggtcggt cgataaaaaa 780

-continued

```
atcgagataa ccgttggcct caatcggcgt taaacccgcc accagatggg cattaaacga    840
gtatcccggc agcaggggat cattttgcgc ttcagccata cttttcatac tcccgccatt    900
cagagaagaa accaattgtc catattgcat cagacattgc cgtcactgcg tcttttactg    960
gctcttctcg ctaaccaaac cggtaacccc gcttattaaa agcattctgt aacaaagcgg   1020
gaccaaagcc atgacaaaaa cgcgtaacaa aagtgtctat aatcacggca gaaaagtcca   1080
cattgattat ttgcacggcg tcacactttg ctatgccata gcatttttat ccataagatt   1140
agcggatcct acctgacgct ttttatcgca actctctact gtttctccat agacgtcggc   1200
gcgccttgtt taactttaag aaggagatat acatatgacc aagaaggtcg gcgtgggcca   1260
ggcccacagc aagatcattc tgatcggcga gcacgccgtg gtgtatggct acccggccat   1320
cagcctgccg ctgctggaag tcgaagtgac gtgcaaggtg gtgccggccg aatccccgtg   1380
gcgtctgtat gaagaggaca cgctgtcgat ggccgtgtat gccagcctgg agtacctgaa   1440
catcaccgag gcctgcatcc gctgcgagat cgactccgcg atcccggaga agcgcggcat   1500
gggcagctcg gccgccatct ccatcgccgc gatccgcgcc gtgttcgact actaccaagc   1560
ggatctgccg catgacgtgc tggagatcct ggtgaaccgg gccgaaatga tcgcccacat   1620
gaatccgagc ggtctggatg ccaagacgtg cctgtccgac cagccgatcc gtttcatcaa   1680
gaacgtgggt ttcaccgagc tggagatgga tctgagcgcg tacctggtga tcgcggacac   1740
cggcgtgtac ggccacaccc gcgaggccat ccaggtcgtg caaaataagg gtaaggacgc   1800
cctgcccttt ctgcacgccc tgggcgaact cacccagcag gccgaagtcg cgatttccca   1860
gaaggacgcc gagggcctgg gtcaaatcct gagccaggcg catctgcacc tgaaggagat   1920
cggcgtgagc agcccggaag cggacttcct ggtcgaaacc accctgtcgc acggtgccct   1980
gggcgcgaag atgtcgggcg gcggcctggg cggctgcatc atcgcgctgg tcaccaacct   2040
gacccatgcg caagagctgg ccgagcgcct ggaagaaaag ggcgccgtcc agacgtggat   2100
cgaatcgctc tgaggattac acacccacat tacatgtaag tacgaagaag aagccaagga   2160
gatatacata tgatcgccgt caagacgtgc ggcaagctgt actgggcggg cgagtatgcc   2220
atcctcgaac ccggccagct ggccctgatc aaggacatcc cgatctatat gcgtgccgaa   2280
atcgcgttca gcgattcgta ccgcatctat tcggatatgt tcgacttcgc cgtcgatctg   2340
cgccccaatc ccgactactc gctgatccaa gaaaccatcg cgctcatggg cgacttcctc   2400
gccgtccgcg gtcagaatct gcgcccgttc agcctggaga tttgcggcaa gatggagcgc   2460
gagggtaaga agttcggcct gggctcctcg ggctccgtgg tggtcctggt cgtgaaggcg   2520
ctgctggcgc tgtacgatgt ctcggtggac caagagctgc tgttcaagct gacctcggcc   2580
gtgctcctga agcgcggcga caacggctcc atgggcgacc tcgcgtgcat cgtggccgag   2640
gacctggtcc tgtaccagtc gtttgaccgc cagaaggtgg cggcgtggct ggaagaagag   2700
aacctggcca cggtgctgga gcgtgactgg ggcttctcca tctcccaggt gaagccgacc   2760
ctggaatgcg acttcctcgt gggctggacc aaggaagtgg cggtgtccag ccacatggtg   2820
caacagatca agcagaacat taaccagaat tttctgacct cgtcgaagga aaccgtcacg   2880
agcctggtgg aagccctgga gcagggcaag tcggagaaga tcatcgacca ggtcgaggtc   2940
gcctccaagc tgctggaagg cctgtccacg gatatctaca ccccccctgct gcgccaactg   3000
aaggaagcct cgcaggacct ccagaccgtg gccaagagca gcggcgccgg cggcggcgac   3060
tgcggcatcg ccctgtcctt cgacgcgcag tccaccaaga ccctgaagaa ccggtgggcg   3120
gacctgggca tcgagctcct gtaccaagag cggatcggcc acgacgacaa gtcgtgaggc   3180
```

```
tagggtagga caccagctag ccattcggcg caaagggatg gcaaggagat atacatatgg   3240

accgcgaacc ggtcaccgtg cgctcgtacg cgaacatcgc catcatcaag tattggggca   3300

agaagaagga aaaggaaatg gtcccggcca cctccagcat ctcgctgacg ctggagaata   3360

tgtacaccga aacgaccctg tcgcccctgc ccgcgaacgt caccgcggac gagttctata   3420

tcaacggcca gctgcagaac gaagtggagc atgcgaagat gagcaagatt atcgatcggt   3480

accgcccggc cggcgagggc tttgtgcgca tcgacacgca gaataacatg ccgacggccg   3540

cgggcctgag cagcagctcg tcgggcctct ccgccctggt caaggcctgc aacgcctact   3600

tcaagctggg cctggaccgc tcgcagctcg cgcaagaagc caagtttgcc agcggctcgt   3660

cctcccgcag cttttacggc ccgctgggcg cgtgggacaa ggactcgggc gaaatctacc   3720

cggtggaaac ggacctcaag ctggccatga tcatgctggt cctggaagat aagaagaagc   3780

cgatctccag ccgcgacggc atgaagctgt gcgtcgaaac cagcaccacg ttcgatgact   3840

gggtgcggca gagcgaaaag gactaccaag acatgctgat ttacctgaag gaaaacgact   3900

tcgcgaagat cggcgaactg accgagaaga atgcgctggc gatgcacgcg acgaccaaga   3960

ccgcctcgcc cgccttctcg tacctgaccg acgccagcta cgaagccatg gccttcgtgc   4020

gccaactccg cgaaaagggc gaggcgtgct acttcacgat ggacgccggc ccgaacgtca   4080

aggtgttctg ccaggaaaag gatctggaac atctgtccga aatcttcggc caccgctacc   4140

gcctgatcgt gagcaagacc aaggatctgt cgcaagacga ctgctgctga gtgcacacta   4200

gtccaggcat caaataaaac gaaaggctca gtcgaaagac tgggcctttc gttttatctg   4260

ttgtttgtcg gtgaacgctc tc                                              4282
```

<210> SEQ ID NO 50
<211> LENGTH: 4264
<212> TYPE: DNA
<213> ORGANISM: artificial sequence
<220> FEATURE:
<223> OTHER INFORMATION: Synthetic

<400> SEQUENCE: 50

```
ttatgacaac ttgacggcta catcattcac tttttcttca caaccggcac ggaactcgct     60

cgggctggcc ccggtgcatt ttttaaatac ccgcgagaaa tagagttgat cgtcaaaacc    120

aacattgcga ccgacggtgg cgataggcat ccgggtggtg ctcaaaagca gcttcgcctg    180

gctgatacgt tggtcctcgc gccagcttaa gacgctaatc cctaactgct ggcggaaaag    240

atgtgacaga cgcgacggcg acaagcaaac atgctgtgcg acgctggcga tatcaaaatt    300

gctgtctgcc aggtgatcgc tgatgtactg acaagcctcg cgtacccgat tatccatcgg    360

tggatggagc gactcgttaa tcgcttccat gcgccgcagt aacaattgct caagcagatt    420

tatcgccagc agctccgaat agcgcccttc cccttgcccg gcgttaatga tttgcccaaa    480

caggtcgctg aaatgcggct ggtgcgcttc atccgggcga aagaaccccg tattggcaaa    540

tattgacggc cagttaagcc attcatgcca gtaggcgcgc ggacgaaagt aaacccactg    600

gtgataccat tcgcgagcct ccggatgacg accgtagtga tgaatctctc ctggcgggaa    660

cagcaaaata tcacccggtc ggcaaacaaa ttctcgtccc tgatttttca ccaccccctg    720

accgcgaatg gtgagattga gaatataacc tttcattccc agcggtcggt cgataaaaaa    780

atcgagataa ccgttggcct caatcggcgt taaacccgcc accagatggg cattaaacga    840

gtatcccggc agcaggggat cattttgcgc ttcagccata cttttcatac tcccgccatt    900
```

-continued

```
cagagaagaa accaattgtc catattgcat cagacattgc cgtcactgcg tcttttactg    960

gctcttctcg ctaaccaaac cggtaacccc gcttattaaa agcattctgt aacaaagcgg   1020

gaccaaagcc atgacaaaaa cgcgtaacaa aagtgtctat aatcacggca gaaaagtcca   1080

cattgattat ttgcacggcg tcacactttg ctatgccata gcatttttat ccataagatt   1140

agcggatcct acctgacgct ttttatcgca actctctact gtttctccat agacgtcggc   1200

gcgccttgtt taactttaag aaggagatat acatatgacc aagaaggtcg gcgtgggcca   1260

ggcccacagc aagatcattc tgatcggcga gcacgccgtg gtgtatggct acccggccat   1320

cagcctgccg ctgctggaag tcgaagtgac gtgcaaggtg gtgccggccg aatccccgtg   1380

gcgtctgtat gaagaggaca cgctgtcgat ggccgtgtat gccagcctgg agtacctgaa   1440

catcaccgag gcctgcatcc gctgcgagat cgactccgcg atcccggaga agcgcggcat   1500

gggcagctcg gccgccatct ccatcgccgc gatccgcgcc gtgttcgact actaccaagc   1560

ggatctgccg catgacgtgc tggagatcct ggtgaaccgg gccgaaatga tcgcccacat   1620

gaatccgagc ggtctggatg ccaagacgtg cctgtccgac cagccgatcc gtttcatcaa   1680

gaacgtgggt ttcaccgagc tggagatgga tctgagcgcg tacctggtga tcgcggacac   1740

cggcgtgtac ggccacaccc gcgaggccat ccaggtcgtg caaaataagg gtaaggacgc   1800

cctgcccttt ctgcacgccc tgggcgaact cacccagcag gccgaagtcg cgatttccca   1860

gaaggacgcc gagggcctgg gtcaaatcct gagccaggcg catctgcacc tgaaggagat   1920

cggcgtgagc agcccggaag cggacttcct ggtcgaaacc accctgtcgc acggtgccct   1980

gggcgcgaag atgtcgggcg gcggcctggg cggctgcatc atcgcgctgg tcaccaacct   2040

gacccatgcg caagagctgg ccgagcgcct ggaagaaaag ggcgccgtcc agacgtggat   2100

cgaatcgctc tgaggattac acacccacat tacatgtaag tacgaagaag aagccaagga   2160

gatatacata tgaacatctc ggagaagaag atgagcatca aggtgccggg caagctgttc   2220

ttcgccggcg agtacagcgt gaccaaggag ggcaacctgg ccctgatcac caccatcgaa   2280

accaacttcg aggtgcgcat ctcggccacc accggcaaga gcatcttcaa gaccaacgtg   2340

ggcctgagcg acttcgagtt ctcgctgtcg aagatcgagt tcaccaagga gaacccgtgg   2400

aacttcgcgc tgaccgccct gaagaacacc ctgtcggccg ccgactcgtt cgagaagaag   2460

tcggtgagca agatcctgtc gtcgtcgccg gaaatcagcc tggagatcgt gtcggacttg   2520

ggcttcggcg agaacaagaa gggctacggc tcgtcggcct cggtggtgtg cggcctggtg   2580

aacgccgtga accagttctt cgacttccag ctgtcgctgg agaagcgctt cgagatcgcg   2640

gccaagaccc acttcgaagt gcagggctcg ggctcgatgg gcgatatcgc cgccatcatg   2700

tacggcggct cggtgttcta ccagaaccat aagcgcgtga tcccgctgga aatcccgtgg   2760

gccacctacg tggtgcagac cggcaaggcc gccaagacca gcgagaagat caagatcaag   2820

ctgtcggacg agttctacca ggccagcaac gagctggtga tcgagctggc caccgccatc   2880

gacatccagg acttcgccct gttcaaggag aagctgtcgg agaaccagct gctgctgctg   2940

gagaacatcc cggagggcta catgaccaag gagctggcca tcgccctgaa cctgctgaac   3000

tcgtacccgg agttcgccgc caagatcagt ggcgccggct tcggcgaaaa catcatcctg   3060

ttcgcccaga acacccaggc catcgccgag gtgcagaaca agctgagcga gtacggcatc   3120

aacctggaga agttcaaggt ggcccagaag aacaactgag gctagggtag gacaccagct   3180

agccattcgg cgcaaaggga tggcaaggag atatacatat ggaccgcgaa ccggtcaccg   3240

tgcgctcgta cgcgaacatc gccatcatca agtattgggg caagaagaag gaaaaggaaa   3300
```

tggtcccggc cacctccagc atctcgctga cgctggagaa tatgtacacc gaaacgaccc 3360
tgtcgcccct gcccgcgaac gtcaccgcgg acgagttcta tatcaacggc cagctgcaga 3420
acgaagtgga gcatgcgaag atgagcaaga ttatcgatcg gtaccgcccg gccggcgagg 3480
gctttgtgcg catcgacacg cagaataaca tgccgacggc cgcgggcctg agcagcagct 3540
cgtcgggcct ctccgccctg gtcaaggcct gcaacgccta cttcaagctg ggcctggacc 3600
gctcgcagct cgcgcaagaa gccaagtttg ccagcggctc gtcctcccgc agcttttacg 3660
gcccgctggg cgcgtgggac aaggactcgg gcgaaatcta cccggtggaa acggacctca 3720
agctggccat gatcatgctg gtcctggaag ataagaagaa gccgatctcc agccgcgacg 3780
gcatgaagct gtgcgtcgaa accagcacca cgttcgatga ctgggtgcgg cagagcgaaa 3840
aggactacca agacatgctg atttacctga aggaaaacga cttcgcgaag atcggcgaac 3900
tgaccgagaa gaatgcgctg gcgatgcacg cgacgaccaa gaccgcctcg cccgccttct 3960
cgtacctgac cgacgccagc tacgaagcca tggccttcgt gcgccaactc cgcgaaaagg 4020
gcgaggcgtg ctacttcacg atggacgccg gcccgaacgt caaggtgttc tgccaggaaa 4080
aggatctgga acatctgtcc gaaatcttcg gccaccgcta ccgcctgatc gtgagcaaga 4140
ccaaggatct gtcgcaagac gactgctgct gagtgcacac tagtccaggc atcaaataaa 4200
acgaaaggct cagtcgaaag actgggcctt tcgttttatc tgttgtttgt cggtgaacgc 4260
tctc 4264

<210> SEQ ID NO 51
<211> LENGTH: 20
<212> TYPE: DNA
<213> ORGANISM: artificial sequence
<220> FEATURE:
<223> OTHER INFORMATION: Synthetic

<400> SEQUENCE: 51
gagagccggc tgacatagac 20

<210> SEQ ID NO 52
<211> LENGTH: 20
<212> TYPE: DNA
<213> ORGANISM: artificial sequence
<220> FEATURE:
<223> OTHER INFORMATION: Synthetic

<400> SEQUENCE: 52
cggcgaccta tgagatcact 20

<210> SEQ ID NO 53
<211> LENGTH: 20
<212> TYPE: DNA
<213> ORGANISM: artificial sequence
<220> FEATURE:
<223> OTHER INFORMATION: Synthetic

<400> SEQUENCE: 53
agaaggctgg gacgaagtct 20

<210> SEQ ID NO 54
<211> LENGTH: 23
<212> TYPE: DNA
<213> ORGANISM: artificial sequence
<220> FEATURE:
<223> OTHER INFORMATION: Synthetic

<400> SEQUENCE: 54
caaatttccg accgctggta ttc 23

<210> SEQ ID NO 55
<211> LENGTH: 1182
<212> TYPE: DNA
<213> ORGANISM: Cupriavidus necator

<400> SEQUENCE: 55
atgactgacg ttgtcatcgt atccgccgcc cgcaccgcgg tcggcaagtt tggcggctcg 60
ctggccaaga tcccggcacc ggaactgggt gccgtggtca tcaaggccgc gctggagcgc 120
gccggcgtca agccggagca ggtgagcgaa gtcatcatgg gccaggtgct gaccgccggt 180
tcgggccaga accccgcacg ccaggccgcg atcaaggccg gcctgccggc gatggtgccg 240
gccatgacca tcaacaaggt gtgcggctcg ggcctgaagg ccgtgatgct ggccgccaac 300
gcgatcatgg cgggcgacgc cgagatcgtg gtggccggcg gccaggaaaa catgagcgcc 360
gccccgcacg tgctgccggg ctcgcgcgat ggtttccgca tgggcgatgc caagctggtc 420
gacaccatga tcgtcgacgg cctgtgggac gtgtacaacc agtaccacat gggcatcacc 480
gccgagaacg tggccaagga atacggcatc acacgcgagg cgcaggatga gttcgccgtc 540
ggctcgcaga acaaggccga agccgcgcag aaggccggca agtttgacga agagatcgtc 600
ccggtgctga tcccgcagcg caagggcgac ccggtggcct tcaagaccga cgagttcgtg 660
cgccagggcg ccacgctgga cagcatgtcc ggcctcaagc ccgccttcga caaggccggc 720
acggtgaccg cggccaacgc ctcgggcctg aacgacggcg ccgccgcggt ggtggtgatg 780
tcggcggcca aggccaagga actgggcctg accccgctgg ccacgatcaa gagctatgcc 840
aacgccggtg tcgatcccaa ggtgatgggc atgggcccgg tgccggcctc caagcgcgcc 900
ctgtcgcgcg ccgagtggac cccgcaagac ctggacctga tggagatcaa cgaggccttt 960
gccgcgcagg cgctggcggt gcaccagcag atgggctggg acacctccaa ggtcaatgtg 1020
aacggcggcg ccatcgccat cggccacccg atcggcgcgt cgggctgccg tatcctggtg 1080
acgctgctgc acgagatgaa gcgccgtgac gcgaagaagg gcctggcctc gctgtgcatc 1140
ggcggcggca tgggcgtggc gctggcagtc gagcgcaaat ga 1182

<210> SEQ ID NO 56
<211> LENGTH: 393
<212> TYPE: PRT
<213> ORGANISM: Cupriavidus necator

<400> SEQUENCE: 56

Met Thr Asp Val Val Ile Val Ser Ala Ala Arg Thr Ala Val Gly Lys
1 5 10 15

Phe Gly Gly Ser Leu Ala Lys Ile Pro Ala Pro Glu Leu Gly Ala Val
20 25 30

Val Ile Lys Ala Ala Leu Glu Arg Ala Gly Val Lys Pro Glu Gln Val
35 40 45

Ser Glu Val Ile Met Gly Gln Val Leu Thr Ala Gly Ser Gly Gln Asn
50 55 60

Pro Ala Arg Gln Ala Ala Ile Lys Ala Gly Leu Pro Ala Met Val Pro
65 70 75 80

Ala Met Thr Ile Asn Lys Val Cys Gly Ser Gly Leu Lys Ala Val Met
85 90 95

Leu Ala Ala Asn Ala Ile Met Ala Gly Asp Ala Glu Ile Val Val Ala

-continued

```
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
        195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390


<210> SEQ ID NO 57
<211> LENGTH: 1509
<212> TYPE: DNA
<213> ORGANISM: Saccharomyces cerevisiae

<400> SEQUENCE: 57

atggtgctga ccaacaagac cgtgatctcg ggctcgaagg tgaagtcgct gtcgtcggcc      60

cagtcgagct cgtcgggccc atcgtcgtcg tcagaagagg acgattcgcg cgacattgag     120

tcgctggaca agaagatccg cccgctggag gaactggaag ccctgctgag ctcgggcaac     180

accaagcagc tgaagaacaa ggaagtggcc gcactggtga tccacggcaa gctgccgctg     240

tacgccttgg aaaagaagtt gggtgacacc acccgcgccg tggcagttcg tcgcaaggcc     300

ttgtcgattc tggccgaagc accggtgctg gcctcggaca gactgccgta caagaactac     360

gactacgacc gcgtgttcgg cgcctgctgc gagaacgtga tcggctatat gccgctgccg     420

gtgggtgtta ttggcccgct ggtgatcgat ggcacctcgt accacattcc gatggccact     480
```

```
accgagggtt gcctggtggc aagcgccatg cgcggttgta aggcaatcaa tgccggtggc    540

ggcgccacca ctgttctgac caaggacggt atgacccgtg gtccggtggt gcgttttccg    600

accttgaagc gctcgggtgc ctgcaaaatc tggctggact cggaggaggg ccagaacgcc    660

atcaagaagg ccttcaattc gacctcgcgc tttgcccgcc tgcagcatat ccagacctgt    720

ttggccggcg acctgctgtt catgcgcttc cgcaccacca ccggcgatgc catgggtatg    780

aacatgatct cgaagggcgt ggagtactcg ctgaagcaga tggtggagga gtacggctgg    840

gaggacatgg aggtggtgag cgtgagcggc aactactgca ccgacaagaa accggcggcc    900

atcaactgga tcgaaggccg cggcaagtca gtggttgccg aagccaccat cccgggcgac    960

gtggtgcgta aggtgctgaa gtcggacgtt tcggccctgg tggaactgaa catcgccaag   1020

aacctggtgg gttcggccat ggcaggttca gtgggcggct tcaatgcaca tgccgcaaac   1080

ttggtgactg ccgtgttcct tgcactgggc caggacccgg cccagaacgt ggagtcgtcg   1140

aactgcatca ccctgatgaa ggaggtggac ggcgacttgc gcatctcggt gtcgatgccg   1200

tcgatcgaag tgggtaccat cggcggtggc accgtgctgg aaccacaggg tgccatgttg   1260

gacttgttgg gcgtgagagg cccacacgca accgcaccag gtaccaatgc acgtcaactt   1320

gcccgcatcg tggcctgcgc cgttttggcc ggtgagctgt cgttgtgtgc agccttggcc   1380

gcaggtcatc tggtgcagtc gcacatgacc cataaccgca aaccggccga gccgaccaag   1440

ccgaacaacc tggacgccac cgacatcaac cgcctgaagg acggctcggt gacctgcatc   1500

aagtcgtga                                                           1509
```

<210> SEQ ID NO 58
<211> LENGTH: 502
<212> TYPE: PRT
<213> ORGANISM: Saccharomyces cerevisiae

<400> SEQUENCE: 58

```
Met Val Leu Thr Asn Lys Thr Val Ile Ser Gly Ser Lys Val Lys Ser
1               5                   10                  15

Leu Ser Ser Ala Gln Ser Ser Ser Ser Gly Pro Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
```

```
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
            260                 265                 270

Gln Met Val Glu Glu Tyr Gly Trp Glu Asp Met Glu Val Val Ser Val
        275                 280                 285

Ser Gly Asn Tyr Cys Thr Asp Lys Lys Pro Ala Ala Ile Asn Trp Ile
    290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
            340                 345                 350

Gly Phe Asn Ala His Ala Ala Asn Leu Val Thr Ala Val Phe Leu Ala
        355                 360                 365

Leu Gly Gln Asp Pro Ala Gln Asn Val Glu Ser Ser Asn Cys Ile Thr
    370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
                405                 410                 415

Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
        435                 440                 445

Leu Ala Gly Glu Leu Ser Leu Cys Ala Ala Leu Ala Ala Gly His Leu
    450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
                485                 490                 495

Val Thr Cys Ile Lys Ser
            500
```

<210> SEQ ID NO 59
<211> LENGTH: 1281
<212> TYPE: DNA
<213> ORGANISM: Listeria monocytogenes

<400> SEQUENCE: 59

```
atgaacgcct tcgacaagtt ctacaaaaag accgtggagg aacgccatgc catcctggcc      60

gagtatgccg acttgaacga ggaagagcag gccttcttgg cctcgaccgg cgccctgtcg     120

ttcgacaagg ccaaccacat gatcgagaac accattggca tctactcgct gccgctgggc     180

ctgggcatga acatgctgct gaacgacaaa cgctacgtgg tgcctatggc aatggaagaa     240

ccgtcggtgg tggccgcaca gtcggccggc gcaaagctga tcgcccagaa tggtggcatt     300
```

-continued

```
accggctcag caaccaagcg caagatgatc ggccagatcg agctgatctc ggtgtcggac    360

atccaggcgg ccaaggagaa catcatcgcc aacgaagaac agctgatcgc catcgcgaac    420

caagcccatc cgtcgctgca gaagcgcggc ggtggcgccg ttaaaattca ggtgcgcacc    480

gcccagactg ccaatgacga aaccctgttc atcgtgcatc tgctggtgga cacccaggaa    540

gccatgggcg ccaacatggt gaacaccatg gtggaaaccc tggccccgga gctggagatg    600

ctgaccaacg gcaccgccaa catgcgcatt ctgagcaacc tggttgatga agccaccgca    660

accgccgtgt gccgcatcaa cccggaatcg ctggccacca aaactcagtc gggcgagtgg    720

gtgcgcgatc gcatcattgc cgcctatgaa tttgccgacg ccgacatcta ccgcgccgcc    780

acccacaaca agggcatcat gaacggcatt gacgccgtga tcatggcctt tggtaacgac    840

tggcgtgccg tggaagccgc ctcacatgcc tacgccgccc gcaccggctc atataagcca    900

atgtcgaagt ggtcgaagga cgccgatggc tacttggtgg gcgaactgac cctgccgatg    960

ccagtggcat tcgtgggcgg tagcatcgcc atccacccga tcgcaagtct gtcgaagaag   1020

atcgcacgcg tggagagcgc aaaggagttg gccatgctgg tgtgcgccgt gggcctgacc   1080

cagaacctgg cagcattgaa agccctggtg accgaaggta tccagcgtgg ccacatgagt   1140

ctgcaggcca agtcactggc aatgaccgcc ggcgccgagg ccgacgagat cgaaatcgtg   1200

gccacctttc tgcaggaatc gaagcagctg aacgtggtgg ccgccaagga gttcatcgcc   1260

aagctgcgct cggagaagtg a                                             1281
```

```
<210> SEQ ID NO 60
<211> LENGTH: 426
<212> TYPE: PRT
<213> ORGANISM: Listeria monocytogenes

<400> SEQUENCE: 60

Met Asn Ala Phe Asp Lys Phe Tyr Lys Lys Thr Val Glu Glu Arg His
1               5                   10                  15

Ala Ile Leu Ala Glu Tyr Ala Asp Leu Asn Glu Glu Glu Gln Ala Phe
            20                  25                  30

Leu Ala Ser Thr Gly Ala Leu Ser Phe Asp Lys Ala Asn His Met Ile
        35                  40                  45

Glu Asn Thr Ile Gly Ile Tyr Ser Leu Pro Leu Gly Leu Gly Met Asn
    50                  55                  60

Met Leu Leu Asn Asp Lys Arg Tyr Val Val Pro Met Ala Met Glu Glu
65                  70                  75                  80

Pro Ser Val Val Ala Ala Gln Ser Ala Gly Ala Lys Leu Ile Ala Gln
                85                  90                  95

Asn Gly Gly Ile Thr Gly Ser Ala Thr Lys Arg Lys Met Ile Gly Gln
            100                 105                 110

Ile Glu Leu Ile Ser Val Ser Asp Ile Gln Ala Ala Lys Glu Asn Ile
        115                 120                 125

Ile Ala Asn Glu Glu Gln Leu Ile Ala Ile Ala Asn Gln Ala His Pro
    130                 135                 140

Ser Leu Gln Lys Arg Gly Gly Gly Ala Val Lys Ile Gln Val Arg Thr
145                 150                 155                 160

Ala Gln Thr Ala Asn Asp Glu Thr Leu Phe Ile Val His Leu Leu Val
                165                 170                 175

Asp Thr Gln Glu Ala Met Gly Ala Asn Met Val Asn Thr Met Val Glu
            180                 185                 190
```

-continued

```
Thr Leu Ala Pro Glu Leu Glu Met Leu Thr Asn Gly Thr Ala Asn Met
        195                 200                 205

Arg Ile Leu Ser Asn Leu Val Asp Glu Ala Thr Ala Thr Ala Val Cys
    210                 215                 220

Arg Ile Asn Pro Glu Ser Leu Ala Thr Lys Thr Gln Ser Gly Glu Trp
225                 230                 235                 240

Val Arg Asp Arg Ile Ile Ala Ala Tyr Glu Phe Ala Asp Ala Asp Ile
                245                 250                 255

Tyr Arg Ala Ala Thr His Asn Lys Gly Ile Met Asn Gly Ile Asp Ala
            260                 265                 270

Val Ile Met Ala Phe Gly Asn Asp Trp Arg Ala Val Glu Ala Ala Ser
        275                 280                 285

His Ala Tyr Ala Ala Arg Thr Gly Ser Tyr Lys Pro Met Ser Lys Trp
    290                 295                 300

Ser Lys Asp Ala Asp Gly Tyr Leu Val Gly Glu Leu Thr Leu Pro Met
305                 310                 315                 320

Pro Val Ala Phe Val Gly Gly Ser Ile Ala Ile His Pro Ile Ala Ser
                325                 330                 335

Leu Ser Lys Lys Ile Ala Arg Val Glu Ser Ala Lys Glu Leu Ala Met
            340                 345                 350

Leu Val Cys Ala Val Gly Leu Thr Gln Asn Leu Ala Ala Leu Lys Ala
        355                 360                 365

Leu Val Thr Glu Gly Ile Gln Arg Gly His Met Ser Leu Gln Ala Lys
    370                 375                 380

Ser Leu Ala Met Thr Ala Gly Ala Glu Ala Asp Glu Ile Glu Ile Val
385                 390                 395                 400

Ala Thr Phe Leu Gln Glu Ser Lys Gln Leu Asn Val Val Ala Ala Lys
                405                 410                 415

Glu Phe Ile Ala Lys Leu Arg Ser Glu Lys
            420                 425
```

<210> SEQ ID NO 61
<211> LENGTH: 1275
<212> TYPE: DNA
<213> ORGANISM: Streptococcus pneumoniae

<400> SEQUENCE: 61

```
atgaagatca gctggaacgg cttctcgaag aagtcgtacc aggaacgcct ggagctgctg      60

aaggcccagg ccctgctgtc gccggaacgc caagcctcgc tggaaaagga tgagcagatg     120

tcggtgaccg tggccgatca gctgtcggaa aacgtggtgg gcaccttctc gctgccgtac     180

tcgctggtgc cggaggttct ggtgaacggc caggagtaca ccgtgcctta tgtgaccgaa     240

gaaccgtcgg tggtggccgc cgcctcatac gcctcaaaga tcatcaagcg cgccggcggt     300

tttaccgccc aggttcacca gcgtcagatg atcggccagg tggcgctgta ccaggtggcc     360

aacccgaagc tggcccagga aaagatcgcc agcaagaagg ccgaactgtt ggaattggcc     420

aaccaggcat acccgtcgat cgtgaagcgc ggcggcggcg cccgcgatct gcacgtggag     480

cagattaagg gcgaaccgga cttcttggtg gtgtatattc acgtggacac ccaggaggcc     540

atgggcgcca acatgctgaa caccatgctg gaggccctga agccggtgct ggaggagctg     600

agccagggtc agtcgctgat gggtatcctg tcgaattacg ccaccgacag cctggtgact     660

gcctcgtgcc gcatcgcctt ccgctatttg tcgcgccaga aggaccaggg ccgtgaaatc     720

gccgagaaga tcgcattggc ctcgcagttc gcccaggccg atccgtatcg cgccgccacc     780
```

-continued

```
cacaataagg gcatcttcaa cggcatcgac gccatcctga tcgcaaccgg caacgattgg    840

cgtgccatcg aggccggtgc ccatgccttc gcctcgcgtg acggtcgtta ccaaggcttg    900

tcgtgttgga ccctggacct ggaacgcgaa gagttggtgg gcgagatgac cctgccgatg    960

ccggttgcca ccaagggcgg ctcgatcggt ctgaatccgc gcgttgttct gtcgcatgac   1020

ctgctgggca atccgtcagc ccgcgaactg gcacagatca tcgtgagcat cggcctggcc   1080

caaaacttcg ccgccctgaa ggccttggtg agtaccggca tccaacaggg ccacatgaag   1140

ctgcaagcca agtcgctggc cttgctggcc ggcgcctcgg aatcagaagt ggccccgctg   1200

gtggagcgtc tgatctcgga caagaccttc aatctggaaa ccgcccagcg ctacctggag   1260

aacctgcgct cgtga                                                    1275
```

<210> SEQ ID NO 62
<211> LENGTH: 424
<212> TYPE: PRT
<213> ORGANISM: Streptococcus pneumoniae

<400> SEQUENCE: 62

```
Met Lys Ile Ser Trp Asn Gly Phe Ser Lys Lys Ser Tyr Gln Glu Arg
1               5                   10                  15

Leu Glu Leu Leu Lys Ala Gln Ala Leu Leu Ser Pro Glu Arg Gln Ala
            20                  25                  30

Ser Leu Glu Lys Asp Glu Gln Met Ser Val Thr Val Ala Asp Gln Leu
        35                  40                  45

Ser Glu Asn Val Val Gly Thr Phe Ser Leu Pro Tyr Ser Leu Val Pro
    50                  55                  60

Glu Val Leu Val Asn Gly Gln Glu Tyr Thr Val Pro Tyr Val Thr Glu
65                  70                  75                  80

Glu Pro Ser Val Val Ala Ala Ala Ser Tyr Ala Ser Lys Ile Ile Lys
                85                  90                  95

Arg Ala Gly Gly Phe Thr Ala Gln Val His Gln Arg Gln Met Ile Gly
            100                 105                 110

Gln Val Ala Leu Tyr Gln Val Ala Asn Pro Lys Leu Ala Gln Glu Lys
        115                 120                 125

Ile Ala Ser Lys Lys Ala Glu Leu Leu Glu Leu Ala Asn Gln Ala Tyr
    130                 135                 140

Pro Ser Ile Val Lys Arg Gly Gly Gly Ala Arg Asp Leu His Val Glu
145                 150                 155                 160

Gln Ile Lys Gly Glu Pro Asp Phe Leu Val Val Tyr Ile His Val Asp
                165                 170                 175

Thr Gln Glu Ala Met Gly Ala Asn Met Leu Asn Thr Met Leu Glu Ala
            180                 185                 190

Leu Lys Pro Val Leu Glu Glu Leu Ser Gln Gly Gln Ser Leu Met Gly
        195                 200                 205

Ile Leu Ser Asn Tyr Ala Thr Asp Ser Leu Val Thr Ala Ser Cys Arg
    210                 215                 220

Ile Ala Phe Arg Tyr Leu Ser Arg Gln Lys Asp Gln Gly Arg Glu Ile
225                 230                 235                 240

Ala Glu Lys Ile Ala Leu Ala Ser Gln Phe Ala Gln Ala Asp Pro Tyr
                245                 250                 255

Arg Ala Ala Thr His Asn Lys Gly Ile Phe Asn Gly Ile Asp Ala Ile
            260                 265                 270

Leu Ile Ala Thr Gly Asn Asp Trp Arg Ala Ile Glu Ala Gly Ala His
        275                 280                 285
```

```
Ala Phe Ala Ser Arg Asp Gly Arg Tyr Gln Gly Leu Ser Cys Trp Thr
    290                 295                 300

Leu Asp Leu Glu Arg Glu Glu Leu Val Gly Glu Met Thr Leu Pro Met
305                 310                 315                 320

Pro Val Ala Thr Lys Gly Gly Ser Ile Gly Leu Asn Pro Arg Val Val
                325                 330                 335

Leu Ser His Asp Leu Leu Gly Asn Pro Ser Ala Arg Glu Leu Ala Gln
            340                 345                 350

Ile Ile Val Ser Ile Gly Leu Ala Gln Asn Phe Ala Ala Leu Lys Ala
        355                 360                 365

Leu Val Ser Thr Gly Ile Gln Gln Gly His Met Lys Leu Gln Ala Lys
    370                 375                 380

Ser Leu Ala Leu Leu Ala Gly Ala Ser Glu Ser Glu Val Ala Pro Leu
385                 390                 395                 400

Val Glu Arg Leu Ile Ser Asp Lys Thr Phe Asn Leu Glu Thr Ala Gln
                405                 410                 415

Arg Tyr Leu Glu Asn Leu Arg Ser
            420


<210> SEQ ID NO 63
<211> LENGTH: 1233
<212> TYPE: DNA
<213> ORGANISM: Lactococcus lactis

<400> SEQUENCE: 63

atgcgcaaga agttctacca gatgtcgccg aaggagcgcc tggacagcct gaacctgtcg     60

gaggacaccc aggaggtgct gagcgagatg gccctggaca ccaacatcct gaacaacctg    120

atcgagaacc agatcagcga gttcgagctg ccgatgggcc tggcgcagaa cttcgtgatc    180

aacggcaagg agtacatcgt gccgatggtg accgaagaac cgagcgtgat cgcagccgcc    240

tcgaacggcg ccaagatcgc cgaatcgttc accgccaaaa tcgacgaacg cctgatgcgc    300

ggccagatcg tgttctacga cgtgaagaag ccggaggaga tcatcaagaa gatcagcgag    360

tgcaagaacg aaatcttcga gcaggccaag ctgtcgtacc cgtcgatcat caagcgtggc    420

ggcggcctgc gcgaaatcag ctcgcgcctg ttctcgtcgg agaagttcat ctcggtggac    480

ttcaaggtgg acgtgaagga cgcaatgggc gccaacatca tcaactcgat cctggagggc    540

gtggccgagc tgttccgcgg ctggttcagc gaggagaaga tcctgttcag catcctgtcg    600

aactacgcca ccgagtcgct ggtgaaggtg agctgcgaga tcagcgtgga cgccctgagc    660

aaaaagacca acggcctgga gatcgcccag aagatcgccg tggcctcgca gtacagcaag    720

atcgacccgt accgcgcctc gacccacaat aagggcatca tgaacggcat caacgccgtg    780

atcctggcaa ccggcaacga cacccgtgcc atttcggccg ccatccacgc ctatgccgca    840

aaggagggca cttaccaggg tttggccaag tgggaggtgc atgccgaaaa gttgttcggc    900

gagctggaaa tcccgctgcc agttgccacc gtgggtggcg gcgtgaaggt gttgccgaag    960

gcacaagccg ccatggaaat cctgggtatc actgatgccc gtgaactggc caaggtgatc   1020

gccgcggttg gtctggccca gaacctggcc gccttgaggg cactggtttc ggaaggcatt   1080

caacaaggcc acatgagctt gcaggcccgt tcgctggcac tgtcggtggg cgcaaaggcc   1140

gacgagatcg cagtgatcag ccagcagttg cgtcaggaga aggtgatgaa ccaggaagtg   1200

gcccgccgcc tgctgaactc gctgcgcaac tga                                1233
```

<210> SEQ ID NO 64
<211> LENGTH: 410
<212> TYPE: PRT
<213> ORGANISM: Lactococcus lactis

<400> SEQUENCE: 64

```
Met Arg Lys Lys Phe Tyr Gln Met Ser Pro Lys Glu Arg Leu Asp Ser
1               5                   10                  15

Leu Asn Leu Ser Glu Asp Thr Gln Glu Val Leu Ser Glu Met Ala Leu
            20                  25                  30

Asp Thr Asn Ile Leu Asn Asn Leu Ile Glu Asn Gln Ile Ser Glu Phe
        35                  40                  45

Glu Leu Pro Met Gly Leu Ala Gln Asn Phe Val Ile Asn Gly Lys Glu
    50                  55                  60

Tyr Ile Val Pro Met Val Thr Glu Glu Pro Ser Val Ile Ala Ala Ala
65                  70                  75                  80

Ser Asn Gly Ala Lys Ile Ala Glu Ser Phe Thr Ala Lys Ile Asp Glu
                85                  90                  95

Arg Leu Met Arg Gly Gln Ile Val Phe Tyr Asp Val Lys Lys Pro Glu
            100                 105                 110

Glu Ile Ile Lys Lys Ile Ser Glu Cys Lys Asn Glu Ile Phe Glu Gln
        115                 120                 125

Ala Lys Leu Ser Tyr Pro Ser Ile Ile Lys Arg Gly Gly Gly Leu Arg
    130                 135                 140

Glu Ile Ser Ser Arg Leu Phe Ser Ser Glu Lys Phe Ile Ser Val Asp
145                 150                 155                 160

Phe Lys Val Asp Val Lys Asp Ala Met Gly Ala Asn Ile Ile Asn Ser
                165                 170                 175

Ile Leu Glu Gly Val Ala Glu Leu Phe Arg Gly Trp Phe Ser Glu Glu
            180                 185                 190

Lys Ile Leu Phe Ser Ile Leu Ser Asn Tyr Ala Thr Glu Ser Leu Val
        195                 200                 205

Lys Val Ser Cys Glu Ile Ser Val Asp Ala Leu Ser Lys Lys Thr Asn
    210                 215                 220

Gly Leu Glu Ile Ala Gln Lys Ile Ala Val Ala Ser Gln Tyr Ser Lys
225                 230                 235                 240

Ile Asp Pro Tyr Arg Ala Ser Thr His Asn Lys Gly Ile Met Asn Gly
                245                 250                 255

Ile Asn Ala Val Ile Leu Ala Thr Gly Asn Asp Thr Arg Ala Ile Ser
            260                 265                 270

Ala Ala Ile His Ala Tyr Ala Ala Lys Glu Gly Thr Tyr Gln Gly Leu
        275                 280                 285

Ala Lys Trp Glu Val His Ala Glu Lys Leu Phe Gly Glu Leu Glu Ile
    290                 295                 300

Pro Leu Pro Val Ala Thr Val Gly Gly Gly Val Lys Val Leu Pro Lys
305                 310                 315                 320

Ala Gln Ala Ala Met Glu Ile Leu Gly Ile Thr Asp Ala Arg Glu Leu
                325                 330                 335

Ala Lys Val Ile Ala Ala Val Gly Leu Ala Gln Asn Leu Ala Ala Leu
            340                 345                 350

Arg Ala Leu Val Ser Glu Gly Ile Gln Gln Gly His Met Ser Leu Gln
        355                 360                 365

Ala Arg Ser Leu Ala Leu Ser Val Gly Ala Lys Ala Asp Glu Ile Ala
    370                 375                 380
```

Val Ile Ser Gln Gln Leu Arg Gln Glu Lys Val Met Asn Gln Glu Val
385 390 395 400

Ala Arg Arg Leu Leu Asn Ser Leu Arg Asn
405 410

<210> SEQ ID NO 65
<211> LENGTH: 1281
<212> TYPE: DNA
<213> ORGANISM: Staphylococcus aureus

<400> SEQUENCE: 65
atgcagtccc tggataagaa ctttcgccat ctgtcgcgcc agcagaagct gcagcaactg 60
gtcgacaagc agtggctgtc cgaggaacag ttcaacatcc tcctgaacca tccgctgatc 120
gacgaagagg tcgccaatag cctgatcgaa aacgtgatcg cgcagggcgc gctgccggtc 180
ggcctgctgc cgaatatcat cgtggacgat aaggcctacg tcgtgccgat gatggtcgaa 240
gaaccgagcg tggtcgccgc cgcgtcgtac ggtgcgaagc tcgtgaatca gaccggcggc 300
ttcaagaccg tgtcgtcgga gcgcatcatg atcggccaga tcgtctttga tggtgtcgac 360
gacaccgaaa agctgtcggc ggacatcaag gccctggaga agcaaatcca ccagatcgcc 420
gacgaagcct atcccagcat taaggcccgc ggtggcggct accagcgcat cgcgattgat 480
accttccccg agcaacagct gctgagcctc aaggtgttcg tggacaccaa ggacgccatg 540
ggcgcgaaca tgctgaacac catcctggaa gcgattaccg ccttcctcaa gaacgaattc 600
ccgcagtcgg acatcctgat gtcgatcctg tccaaccacg ccacggcgtc cgtggtcaag 660
gtccagggcg agatcgacgt gaaggacctg gcgcgtggcg agcgcaccgg cgaagaggtc 720
gccaagcgga tggaacgcgc ctcggtgctg gcccaggtcg acatccaccg tgcggccacg 780
cacaacaagg gtgtgatgaa cggcatccac gccgtggtgc tggccaccgg caacgacacc 840
cggggcgccg aggcgagcgc ccacgcgtat gcgagcaagg acggccagta ccgcggcatc 900
gccacgtggc gctacgatca ggaacgccag cggctgatcg gcaccatcga agtgcccatg 960
acgctggcca tcgtgggcgg cggcaccaag gtcctgccga tcgcgaaggc ctccctggaa 1020
ctgctgaacg tcgagtccgc ccaggaactg ggccacgtcg tcgccgcggt gggcctcgcc 1080
cagaacttcg cggcgtgccg cgcgctggtg tcggaaggca tccagcaagg ccacatgtcg 1140
ctgcagtaca agtccctcgc gatcgtggtg ggtgcgaagg gcgacgaaat cgcccaggtc 1200
gccgaggccc tgaagcaaga gccccgggcc aacacgcaag tggccgagcg tatcctgcaa 1260
gacctccgct cgcagcagtg a 1281

<210> SEQ ID NO 66
<211> LENGTH: 426
<212> TYPE: PRT
<213> ORGANISM: Staphylococcus aureus

<400> SEQUENCE: 66

Met Gln Ser Leu Asp Lys Asn Phe Arg His Leu Ser Arg Gln Gln Lys
1 5 10 15

Leu Gln Gln Leu Val Asp Lys Gln Trp Leu Ser Glu Glu Gln Phe Asn
20 25 30

Ile Leu Leu Asn His Pro Leu Ile Asp Glu Glu Val Ala Asn Ser Leu
35 40 45

Ile Glu Asn Val Ile Ala Gln Gly Ala Leu Pro Val Gly Leu Leu Pro
50 55 60

Asn Ile Ile Val Asp Asp Lys Ala Tyr Val Val Pro Met Met Val Glu

```
65                  70                  75                  80

Glu Pro Ser Val Val Ala Ala Ala Ser Tyr Gly Ala Lys Leu Val Asn
                85                  90                  95

Gln Thr Gly Gly Phe Lys Thr Val Ser Ser Glu Arg Ile Met Ile Gly
            100                 105                 110

Gln Ile Val Phe Asp Gly Val Asp Asp Thr Glu Lys Leu Ser Ala Asp
        115                 120                 125

Ile Lys Ala Leu Glu Lys Gln Ile His Gln Ile Ala Asp Glu Ala Tyr
    130                 135                 140

Pro Ser Ile Lys Ala Arg Gly Gly Gly Tyr Gln Arg Ile Ala Ile Asp
145                 150                 155                 160

Thr Phe Pro Glu Gln Gln Leu Leu Ser Leu Lys Val Phe Val Asp Thr
                165                 170                 175

Lys Asp Ala Met Gly Ala Asn Met Leu Asn Thr Ile Leu Glu Ala Ile
            180                 185                 190

Thr Ala Phe Leu Lys Asn Glu Phe Pro Gln Ser Asp Ile Leu Met Ser
        195                 200                 205

Ile Leu Ser Asn His Ala Thr Ala Ser Val Val Lys Val Gln Gly Glu
    210                 215                 220

Ile Asp Val Lys Asp Leu Ala Arg Gly Glu Arg Thr Gly Glu Glu Val
225                 230                 235                 240

Ala Lys Arg Met Glu Arg Ala Ser Val Leu Ala Gln Val Asp Ile His
                245                 250                 255

Arg Ala Ala Thr His Asn Lys Gly Val Met Asn Gly Ile His Ala Val
            260                 265                 270

Val Leu Ala Thr Gly Asn Asp Thr Arg Gly Ala Glu Ala Ser Ala His
        275                 280                 285

Ala Tyr Ala Ser Lys Asp Gly Gln Tyr Arg Gly Ile Ala Thr Trp Arg
    290                 295                 300

Tyr Asp Gln Glu Arg Gln Arg Leu Ile Gly Thr Ile Glu Val Pro Met
305                 310                 315                 320

Thr Leu Ala Ile Val Gly Gly Gly Thr Lys Val Leu Pro Ile Ala Lys
                325                 330                 335

Ala Ser Leu Glu Leu Leu Asn Val Glu Ser Ala Gln Glu Leu Gly His
            340                 345                 350

Val Val Ala Ala Val Gly Leu Ala Gln Asn Phe Ala Ala Cys Arg Ala
        355                 360                 365

Leu Val Ser Glu Gly Ile Gln Gln Gly His Met Ser Leu Gln Tyr Lys
    370                 375                 380

Ser Leu Ala Ile Val Val Gly Ala Lys Gly Asp Glu Ile Ala Gln Val
385                 390                 395                 400

Ala Glu Ala Leu Lys Gln Glu Pro Arg Ala Asn Thr Gln Val Ala Glu
                405                 410                 415

Arg Ile Leu Gln Asp Leu Arg Ser Gln Gln
            420                 425


<210> SEQ ID NO 67
<211> LENGTH: 1476
<212> TYPE: DNA
<213> ORGANISM: Saccharomyces cerevisiae

<400> SEQUENCE: 67

atgaagctga gcaccaagct gtgctggtgc ggcatcaagg gccgcctgcg cccgcagaag      60

cagcagcagc tgcacaacac caacctgcag atgaccgagc tgaagaagca aaagaccgcc     120
```

```
gagcagaaaa cccgcccgca gaacgtgggc atcaagggca tccagattta catcccgacc    180

cagtgcgtga accagagcga gctggagaag ttcgacggcg tgagccaggg caagtacacc    240

atcggcctgg gccagaccaa catgagcttc gtgaacgacc gcgaggacat ctactcgatg    300

agcctgaccg tgctgtcgaa gctgatcaag tcgtacaaca tcgacaccaa caagatcggc    360

cgcctggagg tgggcaccga aaccctgatc gacaagagca agtcggtgaa gagcgtgctg    420

atgcagctgt tcggcgagaa caccgacgtg gagggcatcg acaccctgaa cgcctgctac    480

ggcggcacca acgccctgtt caactcgctg aactggatcg agagcaacgc ctgggacggt    540

agggatgcaa tcgtggtttg cggcgacatc gccatctacg ataagggtgc cgcacgtccg    600

accggcggtg caggtactgt ggcaatgtgg atcggcccgg atgccccaat cgtgtttgat    660

tcggtgcgcg cctcgtatat ggagcacgcc tacgacttct acaagccgga cttcacctcg    720

gagtacccgt acgtggacgg ccacttctcg ctgacctgct acgtgaaggc cctggaccag    780

gtgtacaagt cgtactcgaa gaaggccatc tcgaagggcc tggtgtcgga cccagccggc    840

agcgacgccc tgaacgtgct gaagtacttc gactacaacg tgttccacgt gccgacctgc    900

aagctggtga ccaagagcta cggccgcctg ttgtacaacg acttccgcgc caatccgcag    960

ctgttcccgg aggtggatgc cgaactggcc acccgcgact acgatgagtc gttgaccgac   1020

aagaacatcg aaaagacctt cgtgaacgtg gccaagccgt tccacaagga gcgcgtggcc   1080

cagtcgctga tcgtgccgac caacaccggc aatatgtaca ccgcctcggt gtatgccgca   1140

tttgcctcgc tgctgaacta cgtgggctcg gacgatttgc agggcaagcg cgttggcctg   1200

ttctcgtacg gctcgggtct ggccgcctca ctgtactcgt gtaagatcgt gggcgacgtg   1260

cagcacatca tcaaggagct ggacatcacc aacaagctgg ccaagcgcat caccgaaacc   1320

ccgaaggact acgaggccgc catcgagctg cgcgagaacg cccacctgaa gaagaacttc   1380

aagccgcagg gcagcatcga gcatctgcag tcgggcgtgt actacctgac caacatcgac   1440

gacaagttcc gccgctcgta cgacgtgaag aagtga                             1476
```

<210> SEQ ID NO 68
<211> LENGTH: 491
<212> TYPE: PRT
<213> ORGANISM: Saccharomyces cerevisiae

<400> SEQUENCE: 68

```
Met Lys Leu Ser Thr Lys Leu Cys Trp Cys Gly Ile Lys Gly Arg Leu
1               5                   10                  15

Arg Pro Gln Lys Gln Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125
```

-continued

```
Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
    290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335

Ser Leu Thr Asp Lys Asn Ile Glu Lys Thr Phe Val Asn Val Ala Lys
            340                 345                 350

Pro Phe His Lys Glu Arg Val Ala Gln Ser Leu Ile Val Pro Thr Asn
        355                 360                 365

Thr Gly Asn Met Tyr Thr Ala Ser Val Tyr Ala Ala Phe Ala Ser Leu
    370                 375                 380

Leu Asn Tyr Val Gly Ser Asp Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
            420                 425                 430

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490
```

<210> SEQ ID NO 69
<211> LENGTH: 1167
<212> TYPE: DNA
<213> ORGANISM: Listeria monocytogenes

<400> SEQUENCE: 69
atgaagatcg gcatcgacaa gatcggcttc tacaccccgg ccttctacgt ggacatggtg     60

-continued

```
gagctggccg aggcccgcaa catcgacccg aacaagttca ccatcggcat cggccaggac    120

aagatggcct tcgccccgat cacccaggac tcggtgacca tgggcgccaa tgccgccctg    180

cagatcctgg acgaagagga tctgaagaag atcgacttgg tgatcctggc caccgaatcg    240

ggcatcgacg agagcaaggc cggtgccgtg tacattcatc gcctgctggg catccagccg    300

ttctcgcgcg ccatcgaaat caaggaggcc tgttacggcg ccaccgccgg tatcaacctg    360

gccaaggact acgtggccaa gcatccagac tcgaaggtgc tggtgattgg ctcggacatt    420

gcacgctatg gcctggccac tggcggcgaa gcaacccagg gtgcaggcgc cgttgccatg    480

gttatcgcag ccgatccacg ctgcattacc ttggaggacg acaacgtgtt ctacaccgag    540

gacatcatgg acttctggcg cccggtgtac tcggagtacg cctgcgtgga gggcaagtac    600

agcaccgagc agtacatcca cttcttccag accatctggg agaagtactc ggccaagttc    660

ggcaagaacc tggaggactt cgcggccatc tgcttccacc tcccgtacac caagatgggc    720

aagaaggccc tggacaccat catcgagact gccccgtcgg acgtgcagga gaagctgctg    780

gagaactacc gcctctcgac cctgtactcg cgcaacgtgg gcaacatcta caccggctcg    840

ctgtacctgt cgttcatctc gctgctggac aaccagccgg acttgcaggc cgaggacaag    900

atcggtttct tctcgtacgg ctcgggcgcc gtgggcgagt tcttccatgg cgtgctgcag    960

ccggactaca agaagtacat ccgcaaggac gagcatgccg aactgctggc caaccgcacc   1020

aagctggcca tcccggacta cgaaaccaag ttcaagcagc aactgccgaa ggacggctcg   1080

attttcgaag tggacccggc cagcgacccg gccgccatcg tgctgaccgg catccaggaa   1140

cacaagcgcc agtacatcaa gaagtga                                       1167
```

<210> SEQ ID NO 70
<211> LENGTH: 388
<212> TYPE: PRT
<213> ORGANISM: Listeria monocytogenes

<400> SEQUENCE: 70

```
Met Lys Ile Gly Ile Asp Lys Ile Gly Phe Tyr Thr Pro Ala Phe Tyr
1               5                   10                  15

Val Asp Met Val Glu Leu Ala Glu Ala Arg Asn Ile Asp Pro Asn Lys
            20                  25                  30

Phe Thr Ile Gly Ile Gly Gln Asp Lys Met Ala Phe Ala Pro Ile Thr
        35                  40                  45

Gln Asp Ser Val Thr Met Gly Ala Asn Ala Ala Leu Gln Ile Leu Asp
    50                  55                  60

Glu Glu Asp Leu Lys Lys Ile Asp Leu Val Ile Leu Ala Thr Glu Ser
65                  70                  75                  80

Gly Ile Asp Glu Ser Lys Ala Gly Ala Val Tyr Ile His Arg Leu Leu
                85                  90                  95

Gly Ile Gln Pro Phe Ser Arg Ala Ile Glu Ile Lys Glu Ala Cys Tyr
            100                 105                 110

Gly Ala Thr Ala Gly Ile Asn Leu Ala Lys Asp Tyr Val Ala Lys His
        115                 120                 125

Pro Asp Ser Lys Val Leu Val Ile Gly Ser Asp Ile Ala Arg Tyr Gly
    130                 135                 140

Leu Ala Thr Gly Gly Glu Ala Thr Gln Gly Ala Gly Ala Val Ala Met
145                 150                 155                 160

Val Ile Ala Ala Asp Pro Arg Cys Ile Thr Leu Glu Asp Asp Asn Val
                165                 170                 175
```

-continued

```
Phe Tyr Thr Glu Asp Ile Met Asp Phe Trp Arg Pro Val Tyr Ser Glu
            180                 185                 190

Tyr Ala Cys Val Glu Gly Lys Tyr Ser Thr Glu Gln Tyr Ile His Phe
        195                 200                 205

Phe Gln Thr Ile Trp Glu Lys Tyr Ser Ala Lys Phe Gly Lys Asn Leu
    210                 215                 220

Glu Asp Phe Ala Ala Ile Cys Phe His Leu Pro Tyr Thr Lys Met Gly
225                 230                 235                 240

Lys Lys Ala Leu Asp Thr Ile Ile Glu Thr Ala Pro Ser Asp Val Gln
                245                 250                 255

Glu Lys Leu Leu Glu Asn Tyr Arg Leu Ser Thr Leu Tyr Ser Arg Asn
            260                 265                 270

Val Gly Asn Ile Tyr Thr Gly Ser Leu Tyr Leu Ser Phe Ile Ser Leu
        275                 280                 285

Leu Asp Asn Gln Pro Asp Leu Gln Ala Glu Asp Lys Ile Gly Phe Phe
    290                 295                 300

Ser Tyr Gly Ser Gly Ala Val Gly Glu Phe Phe His Gly Val Leu Gln
305                 310                 315                 320

Pro Asp Tyr Lys Lys Tyr Ile Arg Lys Asp Glu His Ala Glu Leu Leu
                325                 330                 335

Ala Asn Arg Thr Lys Leu Ala Ile Pro Asp Tyr Glu Thr Lys Phe Lys
            340                 345                 350

Gln Gln Leu Pro Lys Asp Gly Ser Ile Phe Glu Val Asp Pro Ala Ser
        355                 360                 365

Asp Pro Ala Ala Ile Val Leu Thr Gly Ile Gln Glu His Lys Arg Gln
    370                 375                 380

Tyr Ile Lys Lys
385
```

<210> SEQ ID NO 71
<211> LENGTH: 1155
<212> TYPE: DNA
<213> ORGANISM: Lactococcus lactis

<400> SEQUENCE: 71

```
atgaaggtgg gcatcgacaa gctgggcttc ttcgtgccga acaccttcgt ggacatgcgc     60

gacttggcca acgcccgcaa cgtcgatccg gccaaattcc agatcggcat cggccaggac    120

gaaatggccg tgaacccggc cacccaggac atcatcacct tcgccgcgaa cgccgcagcc    180

tcgatcctga ccgaggaaga taagaaggcc atcgacatga tcatcgtggg caccgagtcg    240

tcgctggacg agtcgaaggc ctcggccgtg gtggtgcatg acttgctggg catccaaccg    300

ttcgcccgct cgatcgaaat gaaggaggcc tgctatgcca ctaccgccgg cctgaccctg    360

gcccgtgatc acgtgctgct gaacccggac accaaggtgc tggtgatcgc ctcagacatt    420

gccaagtacg gcctgaacac cggtggcgaa ccgacccaag gcgccggttc ggtggccatg    480

ctgattaccg ccgacccgaa gatcctggcc ctgaacaacg ataacgtggc cctgacccag    540

gacatctacg acttctggcg cccgttcggc caggcctacc cgtcggtgga cggcaagttc    600

tcgaacgaaa cctacatcga cgccttcgcc aagatttgga aggagtactc gcaccgcacc    660

aacctgaagt tcgaggactt cgccgccatc gccttccaca ccccgtacac caagatgggc    720

aagaaggccc tgctgccgat gctggagtcg gaaaagccgg ccaacgccga ggagctgatg    780

gagcagttcg agcatggcat cgtgtacaac cgccgcgtgg gcaatctgta caccggctcg    840

ctgtacctgt cgctgatctc gctgctggaa aactcggaca agctgtcggc cggccagcgt    900
```

atcggcctgt tcagctacgg ctcgggcacc gtggccgaat ttttctcggg cgagctggtg 960
gagggctacg aaaaccatct gctgaagatc gagcaccaga gcatgctgga cgcccgcacc 1020
cgcctgtcga tcccggagta cgagaatatg ttcaaccagt acctggacct gaaccacaac 1080
atctcgttca acgacgaaac cgactactcg gtgtcggagg tggtggacaa ccaccgcaag 1140
tacaagaagc gctga 1155

<210> SEQ ID NO 72
<211> LENGTH: 384
<212> TYPE: PRT
<213> ORGANISM: Lactococcus lactis

<400> SEQUENCE: 72

```
Met Lys Val Gly Ile Asp Lys Leu Gly Phe Phe Val Pro Asn Thr Phe
1               5                   10                  15

Val Asp Met Arg Asp Leu Ala Asn Ala Arg Asn Val Asp Pro Ala Lys
            20                  25                  30

Phe Gln Ile Gly Ile Gly Gln Asp Glu Met Ala Val Asn Pro Ala Thr
        35                  40                  45

Gln Asp Ile Ile Thr Phe Ala Ala Asn Ala Ala Ala Ser Ile Leu Thr
    50                  55                  60

Glu Glu Asp Lys Lys Ala Ile Asp Met Ile Ile Val Gly Thr Glu Ser
65                  70                  75                  80

Ser Leu Asp Glu Ser Lys Ala Ser Ala Val Val Val His Asp Leu Leu
                85                  90                  95

Gly Ile Gln Pro Phe Ala Arg Ser Ile Glu Met Lys Glu Ala Cys Tyr
            100                 105                 110

Ala Thr Thr Ala Gly Leu Thr Leu Ala Arg Asp His Val Leu Leu Asn
        115                 120                 125

Pro Asp Thr Lys Val Leu Val Ile Ala Ser Asp Ile Ala Lys Tyr Gly
    130                 135                 140

Leu Asn Thr Gly Gly Glu Pro Thr Gln Gly Ala Gly Ser Val Ala Met
145                 150                 155                 160

Leu Ile Thr Ala Asp Pro Lys Ile Leu Ala Leu Asn Asn Asp Asn Val
                165                 170                 175

Ala Leu Thr Gln Asp Ile Tyr Asp Phe Trp Arg Pro Phe Gly Gln Ala
            180                 185                 190

Tyr Pro Ser Val Asp Gly Lys Phe Ser Asn Glu Thr Tyr Ile Asp Ala
        195                 200                 205

Phe Ala Lys Ile Trp Lys Glu Tyr Ser His Arg Thr Asn Leu Lys Phe
    210                 215                 220

Glu Asp Phe Ala Ala Ile Ala Phe His Thr Pro Tyr Thr Lys Met Gly
225                 230                 235                 240

Lys Lys Ala Leu Leu Pro Met Leu Glu Ser Glu Lys Pro Ala Asn Ala
                245                 250                 255

Glu Glu Leu Met Glu Gln Phe Glu His Gly Ile Val Tyr Asn Arg Arg
            260                 265                 270

Val Gly Asn Leu Tyr Thr Gly Ser Leu Tyr Leu Ser Leu Ile Ser Leu
        275                 280                 285

Leu Glu Asn Ser Asp Lys Leu Ser Ala Gly Gln Arg Ile Gly Leu Phe
    290                 295                 300

Ser Tyr Gly Ser Gly Thr Val Ala Glu Phe Phe Ser Gly Glu Leu Val
305                 310                 315                 320
```

```
Glu Gly Tyr Glu Asn His Leu Leu Lys Ile Glu His Gln Ser Met Leu
                325                 330                 335

Asp Ala Arg Thr Arg Leu Ser Ile Pro Glu Tyr Glu Asn Met Phe Asn
            340                 345                 350

Gln Tyr Leu Asp Leu Asn His Asn Ile Ser Phe Asn Asp Glu Thr Asp
        355                 360                 365

Tyr Ser Val Ser Glu Val Val Asp Asn His Arg Lys Tyr Lys Lys Arg
    370                 375                 380


<210> SEQ ID NO 73
<211> LENGTH: 1152
<212> TYPE: DNA
<213> ORGANISM: Enterococcus faecalis

<400> SEQUENCE: 73

atgaccatcg gcatcgacaa gatcagcttc ttcgtgccgc cgtactatat tgacatgacc     60

gccctggccg aggcgcgcaa cgtcgacccg ggcaagttcc atatcggcat cggtcaggac    120

cagatggccg tgaaccccat cagccaagac attgtcacct tcgccgccaa cgccgcggaa    180

gccatcctga ccaaggagga caaagaagcg atcgacatgg tgatcgtggg caccgagtcg    240

agcatcgacg agagcaaggc cgccgccgtg gtcctgcatc gcctcatggg tattcagccc    300

ttcgcccgct ccttcgagat caaggagggc tgctacggcg cgaccgccgg cctgcagctc    360

gcgaagaacc acgtggcgct ccacccggac aagaaggtcc tggtcgtcgc cgccgatatc    420

gccaagtacg gcctgaactc gggcggcgag cccacccagg gcgcgggcgc ggtggcgatg    480

ctggtcgcct ccgagccgcg catcctggcc ctgaaggaag ataacgtgat gctgacgcaa    540

gacatctatg acttctggcg cccgacgggc cacccctacc cgatggtcga cggcccgctg    600

tcgaatgaaa cgtacatcca gtccttcgcc caggtgtggg acgagcacaa gaagcggacg    660

ggcctggatt ttgccgacta tgacgcgctg gccttccaca tcccgtacac gaagatgggt    720

aagaaggccc tgctggcgaa gatctcggac cagaccgaag ccgaacagga acgtatcctc    780

gcccggtacg aagagtccat cgtgtactcg cgccgcgtgg gcaacctgta caccggctcg    840

ctgtatctgg gcctgatcag cctgctggag aacgcgacca ccctgaccgc gggcaaccag    900

atcggcctgt tctcgtacgg cagcggcgcc gtcgccgagt tttcacgggc cgaactggtg    960

gccggctacc agaatcatct gcaaaaggaa acccacctgg ccctgctcga caaccgcacc   1020

gagctgagca tcgcggagta cgaagcgatg ttcgcggaaa ccctcgacac ggacatcgat   1080

cagacgctgg aagatgagct gaagtatagc atctcggcga tcaacaacac ggtgcgctcc   1140

taccgcaatt ga                                                       1152


<210> SEQ ID NO 74
<211> LENGTH: 383
<212> TYPE: PRT
<213> ORGANISM: Enterococcus faecalis

<400> SEQUENCE: 74

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60
```

-continued

```
Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Gly Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Val Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
    370                 375                 380
```